United States Patent [19]
Burnie et al.

[11] Patent Number: 5,861,157
[45] Date of Patent: Jan. 19, 1999

[54] DIAGNOSIS AND TREATMENT OF INFECTIONS DUE TO STREPTOCOCCI AND ENTEROCOCCI

[75] Inventors: James Peter Burnie; Ruth Christine Matthews, both of Alderley Edge, United Kingdom

[73] Assignee: NeuTec Pharma plc, United Kingdom

[21] Appl. No.: 687,956

[22] Filed: Jul. 29, 1996

Related U.S. Application Data

[63] Continuation of PCT/GB95/00186 Jan. 30, 1995.

[30] Foreign Application Priority Data

Jan. 28, 1994 [GB] United Kingdom ................... 9401689

[51] Int. Cl.⁶ .................. A61K 39/395; A61K 39/02; C12P 21/06; C07K 1/00
[52] U.S. Cl. ...................... 424/139.1; 424/190.1; 435/69.3; 530/300; 530/350; 536/23.7
[58] Field of Search ..................... 530/350, 300; 536/23.7; 424/139.1, 190.1; 435/23.7

[56] References Cited

U.S. PATENT DOCUMENTS 4,604,234  8/1986  Fujii et al. .
5,416,021  5/1995  Hook et al. .

FOREIGN PATENT DOCUMENTS

94/17411  8/1994  WIPO .

OTHER PUBLICATIONS

Burgess et al (J. of Cell Bio. vol. III pp. 2129–2138), Nov. 1990.
Lazar et al (Molecular & Cellular Bio. vol 8 pp. 1247–1252), Mar. 1988.
Demuth et al (J. of Bio. Chem. vol 265 No. 13 pp. 7120–7126), May 5, 1990.
Takahashi et al (FEBS Letters vol 249 No 2 pp 383–388), Jun. 1989.
Brooks et al (J. of Med. Micro. 37 (Suppl 1) Abstract p.281), 1992.
Clark et al (Serodiagnosis Immunother. Infect. Dis. vol 5 No 2 pp 85–92), 1993.

*Primary Examiner*—Anthony C. Caputa
*Assistant Examiner*—Mark Navarro
*Attorney, Agent, or Firm*—Cushman Darby & Cushman IP Group of Pillsbury Madison & Sutro LLP

[57] ABSTRACT

The present invention provides a purified bacterial protein expressed during infection due to streptococci or enterococci and isolated from human sera, together with immunogenic fragments, analogs, inhibitors, antibodies and antigenic fragments specific thereto. Also provided is a DNA sequence coding for a bacterial protein or an immunogenic fragment or an analogue thereof expressed during infection due to Streptococci or Enterococci, together with homologues thereof, together with vectors, probes and inhibitors therefor. Also provided is fibronectin or an immunogenic fragment thereof or an analogue thereof or an antibody thereto or an anigen binding fragment thereof when used in a method of treatment or diagnosis of the human or animal body for infection due to Streptococci or Enterococci. Also provided are antibodies specific to HSP 90 or immunogenic fragments or analogues thereof for use in a method of diagnosis or treatment of the human or animal body of infection due to steptococci or enterococci due to any one of the group of *S.oralis, S.gordonii, S.sanguis*.

13 Claims, 11 Drawing Sheets

Figure 8

S. oralis

Peptide 1 — Y E V E K P L E P A P V A P S Y E N E P T P P V K T P D Q P E P S K P E E P T Peptide 4 — E P A P V A P Peptide 2 — S Y E N E P T Peptide 3 — K T P D S. sobrinus Peptide 5 — Y E V E K E L V D L P V E P S V E K E P T P P S K T P D Q N I P D K P V E P T Peptide 6 — K T P D Q N I P D K P V E P T

Figure 10

Gap alignment of the *S. sobrinus* antigenic region with the human Fibronectin primary sequence

```
                      710                 730                 750
FN HUM      STSTPVTSNT VTGETIPFSP LVATSESVTE ITASSFVVSW VSASDTVSGF

ESA STRSO   .......... .......... .......... .......... .........Y
                      760                 770                 790
FN HUM      RVEYELSEEG DEPQYLDLPS TATSVNIPDL LPGRKYIVNV YQISEDGEQS

ESA STRSO   EVEKELVDLP VEPSYEKEPT PPS....... .......... ..........
                      810                 830                 850
FN HUM      LILSTSQTTA PDAPPDPTVD QVDDTSIVVR WSRPQATITG YRIVYSPSVE

ESA STRSO   ...KTPDQNI PDKPVEPT.. .......... .......... ..........
```

Key for Figure 10:

FN HUM    the human fibronectin primary sequence homologous to the ESA STRSO peptin region.

ESA STRSO    the proposed S.sobrinus endocarditis specific antigenic site.

The numbers correspond to the amino acids of the complete human fibronectin primary sequence.

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 605 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Streptococcus oralis ( x i ) SEQUENCE DESCRIPTION: SEQ ID NO:1:

```
Glu Phe Thr Phe Tyr Asp Glu Asn Asp Gln Pro Ile Asn Phe Asp Asn
 1               5                  10                  15

Ala Leu Leu Ser Val Ala Ser Leu Asn Arg Glu His Asn Ser Ile Glu
            20                  25                  30

Met Ala Lys Asp Tyr Ser Gly Thr Phe Ile Lys Ile Ser Gly Ser Ser
         35                  40                  45

Ile Gly Glu Lys Asn Gly Met Ile Tyr Ala Thr Glu Thr Leu Asn Phe
     50                  55                  60

Lys Gln Gly Gln Gly Gly Ala Arg Trp Thr Met Tyr Pro Asn Arg Gln
 65                  70                  75                  80

Pro Gly Ser Gly Trp Asp Ser Ser Asp Ala Pro Asn Ser Trp Tyr Gly
                 85                  90                  95

Ala Gly Ala Ile Ser Met Ser Gly Pro Thr Asn His Val Thr Val Gly
            100                 105                 110

Ala Thr Ser Ala Thr Asn Val Met Ser Val Ala Glu Met Pro Gln Val
         115                 120                 125

Pro Gly Arg Asp Asn Thr Glu Gly Lys Arg Pro Asn Ile Trp Tyr Ser
     130                 135                 140

Leu Asn Gly Lys Ile Arg Ala Val Asp Val Pro Lys Ile Thr Lys Glu
145                 150                 155                 160

Lys Pro Thr Pro Pro Val Ala Pro Thr Glu Pro Gln Ala Pro Thr Tyr
                 165                 170                 175

Glu Val Glu Lys Pro Leu Glu Pro Ala Pro Val Ala Pro Ser Tyr Glu
            180                 185                 190

Asn Glu Pro Thr Pro Pro Val Lys Thr Pro Asp Gln Pro Glu Pro Ser
         195                 200                 205

Lys Pro Glu Glu Pro Thr Tyr Glu Thr Glu Lys Pro Leu Glu Pro Ala
     210                 215                 220

Pro Val Ala Pro Asn Tyr Glu Asn Glu Pro Thr Pro Pro Val Lys Thr
225                 230                 235                 240

Pro Asp Gln Pro Asp Pro Ser Lys Pro Glu Glu Pro Asn Tyr Glu Thr
                 245                 250                 255

Glu Lys Pro Leu Glu Pro Ala Pro Val Ala Pro Ser Tyr Glu Asn Glu
            260                 265                 270

Pro Thr Pro Pro Val Lys Thr Pro Asp Gln Pro Glu Pro Ser Lys Pro
```

|   |   |   |   |   | 275 |   |   |   |   | 280 |   |   |   |   | 285 |   |   |   |
|---|---|---|---|---|---|---|---|---|---|---|---|---|---|---|---|---|---|---|

Glu Glu Pro Asn Tyr Asp Pro Leu Pro Thr Pro Pro Leu Ala Pro Thr
290                     295                 300

Pro Lys Gln Leu Pro Thr Pro Pro Ala Val Pro Thr Val His Phe His
305                 310                 315                 320

Tyr Asn Arg Leu Phe Ala Gln Pro Gln Ile Asn Lys Glu Ile Lys Asn
                325                 330                 335

Glu Asp Gly Val Asp Ile Asp Arg Thr Leu Val Ala Lys Gln Ser Val
            340                 345                 350

Val Lys Phe Glu Leu Lys Thr Glu Ala Leu Thr Ala Gly Arg Pro Lys
        355                 360                 365

Thr Thr Ser Phe Val Leu Val Asp Pro Leu Pro Thr Gly Tyr Gln Phe
    370                 375                 380

Asp Leu Glu Ala Thr Lys Ala Ala Ser Lys Gly Phe Glu Thr Ser Tyr
385                 390                 395                 400

Asp Lys Ala Ser His Thr Val Thr Phe Lys Ala Thr Glu Glu Thr Leu
                405                 410                 415

Ala Ala Phe Asn Ala Asp Leu Thr Lys Ser Phe Glu Thr Leu Tyr Pro
            420                 425                 430

Thr Val Val Gly Arg Val Leu Asn Asp Gly Ala Thr Tyr Thr Asn Asn
        435                 440                 445

Phe Thr Leu Thr Val Asn Asp Ala Thr Gly Val Lys Ser Asn Ile Val
    450                 455                 460

Arg Val Thr Thr Pro Gly Lys Pro Asn Asp Pro Asp Asn Pro Asn Asn
465                 470                 475                 480

Asn Tyr Ile Lys Pro Leu Lys Val Asn Lys Asn Lys Gln Gly Val Asn
                485                 490                 495

Ile Asp Gly Lys Glu Val Leu Ala Gly Ser Thr Asn Tyr Tyr Glu Leu
            500                 505                 510

Thr Trp Asp Leu Asp Gln Tyr Lys Gly Asp Lys Ser Ser Lys Glu Ala
        515                 520                 525

Ile Gln Asn Gly Phe Tyr Tyr Val Asp Asp Tyr Pro Glu Glu Ala Leu
    530                 535                 540

Thr Leu Gln Pro Glu Leu Val Lys Ile Arg Asp Leu Glu Gly Asn Leu
545                 550                 555                 560

Val Ser Gly Ile Ser Val Gln Gln Phe Asp Ser Leu Glu Arg Ala Pro
                565                 570                 575

Lys Lys Val Gln Asp Leu Leu Lys Lys Ala Asn Ile Thr Val Lys Gly
            580                 585                 590

Ala Phe Gln Leu Phe Ser Ala Asp Asn Pro Ala Glu Phe
        595                 600                 605

(2) INFORMATION FOR SEQ ID NO:2:

(i) SEQUENCE CHARACTERISTICS:
        (A) LENGTH: 1815 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus oralis ( x i ) SEQUENCE DESCRIPTION: SEQ ID NO:2:

```
GAATTCACCT TCTACGATGA AAATGACCAA CCAATTAATT TTGACAATGC TCTTCTTTCA      60
GTAGCCTCAC TTAACCGTGA GCATAACTCT ATTGAGATGG CTAAGGATTA TAGTGGTACT     120
TTTATTAAAA TCTCAGGTTC ATCCATCGGT GAAAAAAATG GCATGATTTA TGCCACAGAA     180
ACCCTGAACT TTAAACAAGG ACAGGGTGGA GCTCGCTGGA CAATGTATCC AAATCGTCAG     240
CCAGGTTCAG GTTGGGATTC ATCAGATGCA CCAAACTCTT GGTACGGTGC AGGGGCCATT     300
AGTATGTCCG GTCCTACGAA TCACGTTACA GTTGGTGCAA CATCTGCTAC CAATGTGATG     360
TCCGTAGCAG AAATGCCTCA AGTACCTGGA AGAGACAATA CTGAAGGTAA AAGACCAAAC     420
ATCTGGTACT CACTCAATGG TAAAATTCGT GCGGTTGACG TTCCGAAAAT TACAAAAGAA     480
AAACCAACTC CACCGGTAGC ACCAACTGAA CCACAAGCTC CTACCTATGA AGTGGAGAAA     540
CCACTGGAAC CGGCTCCAGT AGCACCAAGC TACGAAAATG AGCCAACTCC ACCAGTAAAA     600
ACTCCAGATC AACCGGAGCC ATCAAAACCA GAAGAGCCAA CATATGAGAC AGAGAAACCA     660
TTGGAACCAG CTCCAGTAGC ACCAAACTAC GAAAATGAGC CAACTCCACC AGTAAAAACT     720
CCAGATCAAC CAGACCCATC AAAACCGGAA GAGCCAAACT ATGAGACAGA GAACCATTG     780
GAACCAGCTC CAGTAGCACC AAGCTATGAA AATGAGCCAA CTCCACCGGT AAAAACTCCA     840
GATCAACCAG AGCCATCAAA ACCAGAAGAG CCAAATTATG ATCCATTGCC AACTCCGCCG     900
CTAGCACCAA CTCCTAAGCA GTTGCCAACA CCACCAGCGG TGCCAACAGT TCACTTCCAT     960
TACAATCGTC TATTTGCACA ACCTCAGATT AATAAGAAA TTAAAAACGA GGATGGAGTA    1020
GATATTGATC GTACTCTAGT TGCTAAGCAG TCTGTAGTGA AGTTTGAGCT GAAAACAGAA    1080
GCTTTAACTG CTGGTCGTCC AAAAACAACT TCGTTTGTAT GGTAGATCC ACTTCCAACT    1140
GGCTATCAGT TTGATTTGGA AGCAACCAAG GCTGCAAGCA AAGGTTTTGA AACAAGCTAT    1200
GACAAAGCTA GTCACACTGT AACCTTTAAG GCTACTGAGG AGACCTTAGC TGCTTTCAAT    1260
GCTGATTTGA CAAAATCCTT TGAGACTCTA TATCCAACTG TTGTTGGTCG TGTCTTGAAT    1320
GATGGGGCGA CTTATACGAA TAACTTTACA TTGACAGTCA ACGATGCTAC TGGTGTCAAG    1380
TCAAACATTG TTCGTGTAAC GACTCCAGGT AAACCAAATG ATCCTGACAA TCCAAATAAC    1440
AACTACATCA AGCCTTTGAA AGTTAACAAG AACAAGCAAG GTGTGAATAT TGATGGCAAA    1500
GAAGTTCTAG CTGGTTCAAC GAACTACTAT GAACTCACAT GGGATTTGGA TCAATACAAG    1560
GGAGATAAAT CTTCTAAAGA AGCGATTCAA AATGGTTTCT ACTATGTGGA TGATTATCCA    1620
GAAGAAGCTT TAACGCTTCA ACCAGAATTG GTTAAGATTC GTGATCTAGA GGGCAACCTT    1680
GTATCAGGTA TCAGTGTTCA ACAGTTTGAT AGTTTAGAAC GTGCGCCTAA GAAGGTTCAA    1740
GATCTGTTGA AGAAAGCAAA CATCACTGTT AAAGGTGCTT TCCAACTCTT CTCAGCTGAT    1800
AATCCAGCTG AATTC                                                    1815
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal (v i) ORIGINAL SOURCE:
  (A) ORGANISM: Streptococcus oralis (x i) SEQUENCE DESCRIPTION: SEQ ID NO:3:

Tyr Glu Val Glu Lys Pro Leu Glu Pro Ala Pro Val Ala Pro Ser
1               5                   10                  15

(2) INFORMATION FOR SEQ ID NO:4:

(i) SEQUENCE CHARACTERISTICS:
    (A) LENGTH: 14 amino acids
    (B) TYPE: amino acid
    (D) TOPOLOGY: unknown (i i) MOLECULE TYPE: peptide (i i i) HYPOTHETICAL: NO (i v) ANTI-SENSE: NO (v) FRAGMENT TYPE: internal (v i) ORIGINAL SOURCE:
    (A) ORGANISM: Streptococcus oralis (x i) SEQUENCE DESCRIPTION: SEQ ID NO:4:

Ser Tyr Glu Asn Glu Pro Thr Pro Pro Val Lys Thr Pro Asp
1               5                   10

(2) INFORMATION FOR SEQ ID NO:5:

(i) SEQUENCE CHARACTERISTICS:
    (A) LENGTH: 15 amino acids
    (B) TYPE: amino acid
    (D) TOPOLOGY: unknown (i i) MOLECULE TYPE: peptide (i i i) HYPOTHETICAL: NO (i v) ANTI-SENSE: NO (v) FRAGMENT TYPE: internal (v i) ORIGINAL SOURCE:
    (A) ORGANISM: Streptococcus oralis (x i) SEQUENCE DESCRIPTION: SEQ ID NO:5:

Lys Thr Pro Asp Gln Pro Glu Pro Ser Lys Pro Glu Glu Pro Thr
1               5                   10                  15

(2) INFORMATION FOR SEQ ID NO:6:

(i) SEQUENCE CHARACTERISTICS:
    (A) LENGTH: 15 amino acids
    (B) TYPE: amino acid
    (D) TOPOLOGY: unknown (i i) MOLECULE TYPE: peptide (i i i) HYPOTHETICAL: NO (i v) ANTI-SENSE: NO (v) FRAGMENT TYPE: internal (v i) ORIGINAL SOURCE:
    (A) ORGANISM: Streptococcus oralis (x i) SEQUENCE DESCRIPTION: SEQ ID NO:6:

Glu Pro Ala Pro Val Ala Pro Ser Tyr Glu Asn Glu Pro Thr Pro
1               5                   10                  15

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Streptococcus sobrinus
        ( B ) STRAIN: Streptococcus sobrinus MUCOB 263

( x i ) SEQUENCE DESCRIPTION: SEQ ID NO:7:

```
Tyr  Glu  Val  Glu  Lys  Glu  Leu  Val  Asp  Leu  Pro  Val  Glu  Pro  Ser
1                   5                        10                       15
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Streptococcus sobrinus
        ( B ) STRAIN: Streptococcus sobrinus MUCOB 263

( x i ) SEQUENCE DESCRIPTION: SEQ ID NO:8:

```
Lys  Thr  Pro  Asp  Gln  Asn  Ile  Pro  Asp  Lys  Pro  Val  Glu  Pro  Thr
1                   5                        10                       15
```

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Streptococcus oralis ( x i ) SEQUENCE DESCRIPTION: SEQ ID NO:9:

```
Thr  Met  Tyr  Pro  Asn  Arg  Gln  Pro  Gly  Ser  Gly  Trp  Asp  Ser  Ser
1                   5                        10                       15
```

( 2 ) INFORMATION FOR SEQ ID NO:10:

( i ) SEQUENCE CHARACTERISTICS:
        ( A ) LENGTH: 15 amino acids
        ( B ) TYPE: amino acid (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
    (A) ORGANISM: Streptococcus oralis (xi) SEQUENCE DESCRIPTION: SEQ ID NO:10:

| Trp | Tyr | Ser | Leu | Asn | Gly | Lys | Ile | Arg | Ala | Val | Asp | Val | Pro | Lys |
|---|---|---|---|---|---|---|---|---|---|---|---|---|---|---|
| 1 | | | | 5 | | | | | 10 | | | | | 15 |

(2) INFORMATION FOR SEQ ID NO:11:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:11:

CAGTCTCCGT CCCAACGACT GCG               23

(2) INFORMATION FOR SEQ ID NO:12:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:12:

GCTCCTCTTG TCACATGGTC               20

(2) INFORMATION FOR SEQ ID NO:13:

(i) SEQUENCE CHARACTERISTICS:
    (A) LENGTH: 7 amino acids
    (B) TYPE: amino acid
    (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

| Asn | Phe | Lys | Gln | Gly | Gln | Gly |
|---|---|---|---|---|---|---|
| 1 | | | | 5 | | |

(2) INFORMATION FOR SEQ ID NO:14:

(i) SEQUENCE CHARACTERISTICS:
    (A) LENGTH: 4 amino acids
    (B) TYPE: amino acid
    (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:14:

Arg Gln Pro Gly
1

(2) INFORMATION FOR SEQ ID NO:15:

(i) SEQUENCE CHARACTERISTICS:
(A) LENGTH: 6 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:15:

Ser Trp Tyr Gly Ala Gly
1               5

(2) INFORMATION FOR SEQ ID NO:16:

(i) SEQUENCE CHARACTERISTICS:
(A) LENGTH: 6 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:16:

Gly Lys Ile Arg Ala Val
1               5

(2) INFORMATION FOR SEQ ID NO:17:

(i) SEQUENCE CHARACTERISTICS:
(A) LENGTH: 7 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:17:

Arg Leu Phe Ala Gln Pro Gln
1               5

(2) INFORMATION FOR SEQ ID NO:18:

(i) SEQUENCE CHARACTERISTICS:
(A) LENGTH: 5 amino acids
(B) TYPE: amino acid
(D) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:18:

Ala Gly Arg Pro Lys
1               5

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:19:

Pro Thr Gly Tyr Gln Phe Asp
1               5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:20:

Tyr Pro Thr Val Val
1               5

( 2 ) INFORMATION FOR SEQ ID NO:21:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:21:

Leu Leu Lys Lys Ala
1               5

( 2 ) INFORMATION FOR SEQ ID NO:22:

( i ) SEQUENCE CHARACTERISTICS:
  ( A ) LENGTH: 5077 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Streptococcus sobrinus ( x i ) SEQUENCE DESCRIPTION: SEQ ID NO:22:

| | | | | | |
|---|---|---|---|---|---|
| GCTCCTCTTG | TGACATGGTC | ATAGTAACAG | ATAATCTGTT | TAATTTCAAG | CAGATTTAAT | 60 |
| AGCCTCCAGG | AAACTTGAAA | TAAAACTGAA | ATAAAACTGA | ATTTTTATA | AAGCCTAGAT | 120 |
| TAAGCAATCG | TTTGCATTGA | CAATCACTAG | ATAAGTGTTA | TTATAGATAG | TATTGTAACG | 180 |
| AAACATTTCA | GATGTTACAA | AAATGTAAAT | TGGAGGGAAT | TATAATATGC | AACGAAAAGA | 240 |
| GACTTTTGGG | TTTCGCAAAA | GTAAAATCAG | TAGGACCCTT | TGTGGTGCCT | TACTAGGAAC | 300 |
| TGCTATCTTA | GCGTCTGTAA | CAGGTCAAAA | GGCGCTCGCT | GAAGAAACAA | GTACCACTTC | 360 |
| AACTTCGGGG | GTTAATACCG | CAGTCGTTGG | GACGGAGACT | GGGAATCCCG | CCACCAACCT | 420 |
| GCCTGACAAA | CAGGACAATC | CAAGTTCGCA | AGCCGAGACA | AGTCAGGCCC | AAGCCGGTCA | 480 |
| AAAGACAGGG | GCAATGTCAG | TAGATGTGTC | TACAAGTGAG | CTTGACGAAG | CTGCTAAAAG | 540 |
| TGCCCAAGAA | GCTGGTGTGA | CCGTTTCGCA | GGATGCTACC | GTCGATAAAG | GGACAGTAGA | 600 |
| AACTTCTGAC | GAAGCTAACC | AAAAAGAAAC | CGAAATCAAG | GATGACTACA | GCAAGCAAGC | 660 |
| AGCAGACATC | CAAAAGACAA | CAGAAGACTA | CAAGGCAGCT | GTGGCTCGTA | ACCAAGCCGA | 720 |
| AACAGACCGA | ATCACTCAAG | AAAACGCGGC | TAAGAAGGCC | CAATACGAAC | AAGATTTGGC | 780 |
| GGCCAACAAG | GCAGAAGTGG | AACGCATTAC | CAATGAGAAT | GCGCAACGCA | AGGCTGATTA | 840 |
| CGAAGCTAAG | CTGGCTCAAT | ATCAAAAGGA | CCTAGCAGCC | GTTCAACAAG | CTAATAATGA | 900 |
| CAGTCAAGCA | GCCTACGCTG | CTGCCAAGGA | AGCCTACGAC | AAAGAATTGG | CTCGGGTTCA | 960 |
| AGCTGCTAAT | GCCGCTGCTA | AGAAAGAATA | CGAAGAGGCT | CTAGCTGCCA | ACACCACTAA | 1020 |
| GAATGAGCAA | ATCAAGGCAG | AAAACGCCGC | TATCCAGCAA | CGCAATGCCC | AAGCTAAGGC | 1080 |
| AGATTACGAA | GCCAAGTTGG | CTCAATATGA | AAAAGATTTA | GCCGCAGCCC | AGTCTGGTAA | 1140 |
| TGCTACAAAT | GAAGCGGACT | ACCAAGCTAA | GAAGGCAGCT | TATGAACAAG | AGTTAGCGCG | 1200 |
| CGTGCAAGCC | GCTAATGCAG | CTGCCAAGCA | GGCCTACGAA | CAAGCTCTAG | CTGCCAACAC | 1260 |
| GGCCAAGAAC | GCCCAAATCA | CGGCCGAAAA | TGAGGCTATC | CAGCAGCGCA | ATGCGCAAGC | 1320 |
| TAAGGCTAAC | TATGAAGCTA | AATTAGCCCA | ATATCAAAAG | GATTTGGCCG | CAGCTCAATC | 1380 |
| TGGTAACGCC | GCTAATGAGG | CAGACTACCA | AGAAAAATTA | GCAGCCTATG | AAAAGGAACT | 1440 |
| GGCTCGTGTG | CAAGCAGCCA | ATGCAGCTGC | TAAGCAAGAA | TATGAGCAGA | AAGTTCAGGA | 1500 |
| AGCTAATGCT | AAAAATGCCG | AAATTACGGA | AGCCAACCGT | GCTATCCGTG | AACGCAATGC | 1560 |
| CAAGGCCAAG | ACAGACTATG | AACTCAAACT | GTCTAAGTAC | CAAGAAGAGC | TTGCTCAGTA | 1620 |
| CAAGAAGGAC | CTAGCGGAAT | ACCCAGCTAA | ACTCCAAGCC | TATCAAGATG | AACAAGCCGC | 1680 |
| AATCAAGGCA | GCTCTGGAAG | AGTTGGAAAA | GCACAAGAAT | GAAGATTGGA | ACCTCAGTGA | 1740 |
| GCCCTCAGCC | CAGAGTCTGG | TCTATGACTT | GGAGCCCAAT | GCTCAGATTT | CCCTAGTGAC | 1800 |
| CGATTGGAAG | CTACTGAAAG | CCTCCTCCCT | TGATGAATCC | TTTAGCCACG | ATACTGAACA | 1860 |
| ATATAACAAA | CACAACCTGC | AGCCAGATAA | TCTAAATATA | ACCTATCTGG | AGCAGGCTGA | 1920 |

```
TGATGTGGCC  TCCTCAGTAG  AGCTCTTTGG  TAATTTCGGT  GATAAGGCTG  GTTGGACAAC   1980
CACTGTCAGC  AATGGTTCAG  AAGTTAAGTT  TGCCTCTGTC  CTCCTCAAGC  GTGGCCAGAG   2040
TGCTACAGCC  ACCTATACCA  ACCTGAAAAA  CTCTTACTAC  AATGGTAAGA  AAATTTCTAA   2100
GGTGGTCTAC  AAGTATACGG  TTGACCCTGA  CTCCAAGTTT  CAAAATCCTA  CTGGTAACGT   2160
TTGGTTAGGT  ATCTTTACTG  ACCCAACCCT  AGGGGTCTTT  GCCTCAGCCT  ATACGGGTCA   2220
AAACGAGAAG  GATACCTCTA  TCTTTATCAA  GAATGAATTC  ACCTTCTACG  ATGAAGACGG   2280
TAATCCCATC  GACTTTGATA  ATGCCCTCTT  GTCAGTTGCC  TCCCTTAACA  GGGAACACAA   2340
TTCCATTGAG  ATGGCCAAGG  ACTACAGCGG  TACCTTCGTT  AAGATTTCTG  GCTCATCCAT   2400
TGGTGAAAAA  AATGGCATGA  TCTATGCGAC  CGACACCCTC  AACTTTAAAA  AGGGTGAAGG   2460
CGGTTCCCTT  CACACCATGT  ACACCAGAGC  AAGTGAGCCT  GGTTCAGGTT  GGGACTCTGC   2520
TGATGCTCCT  AATTCTTGGT  ATGGTGCTGG  TGCTGTCAGA  ATGTCCGGCC  CAAACAACTA   2580
CATCACTTTG  GGGCAACCT   CAGCGACCAA  TGTCCTCAGC  CTAGCTGAAA  TGCCACAGGT   2640
ACCTGGTAAA  GATAATACTG  CTGGTAAAAA  ACCAAATATC  TGGTATTCCC  TTAATGGTAA   2700
GATTCGGGCA  GTCAATGTCC  CTAAAGTGAC  CAAGGAAAAA  CCAACCCCAC  CAGTTGAGCC   2760
AACCAAGCCA  GACGAGCCAG  TCTATGAAGT  TGAGAAGGAA  TTGGTAGATC  TGCCAGTTGA   2820
ACCAAGCTAC  GAAAAGGAAC  CAACCCCACC  AAGCAAGACT  CCAGACCAAA  ATATCCCAGA   2880
CAAACCAGTA  GAGCCTACTT  ATGAGGTTGA  AAAGGAGCTG  GAACCGGCAC  CAGTTGAGCC   2940
AAGCTACGAA  AAGGAACCAA  CGCCACCAAG  CAAGACTCCG  GATCAAGCGA  TTCCAGACAA   3000
ACCGGTAGAG  CCAACCTATG  AGGTTGAAAA  GGAGTTGGAA  CCAGTACCTG  TAGAAACAAA   3060
CTACGAAAAG  GAACCAACCC  CGCCTCAGTC  AACCCCAGAC  CAAGAAGAGC  CCACCAAACC   3120
GGTGGAACCA  AGCTACCAAA  GCTTGCCAAC  CCCACCAGTG  GCACCGACTT  ATGAAAAGGT   3180
TCCTGGTCCT  GTCAGTGTGC  CAACGGTTCG  GTACCACTAC  TATAAACTAG  CGGTCCAACC   3240
CGGCGTCACC  AAGAAAATCA  AAAACCAGGA  TGACCTGGAT  ATTGACAAGA  CCCTGGTGGC   3300
TAAGCAGTCG  ACGGTTAAGT  TCCAATTGAA  GACAGCAGAC  CTGCCAGCCG  GTCGTCCAGA   3360
AACGACCTCC  TTTGTCTTGA  TGGATCCTCT  GCCAAGCGGT  TACCAACTTA  ATCTGGAAGC   3420
TACCAAGGTC  GCCAGCCCAG  GCTTTGAAGC  TAGCTATGAT  GCCATGACCC  ATACGGTAAC   3480
CTTCATCGCA  ACCGCTGAGA  CCTTGGCGGC  GCTCAACCAG  GATCTGACCA  AGGCCGTGGC   3540
GACTATCTAC  CCAACAGTTG  TGGACAAGT   CCTCAACGAT  GGCGCTACCT  ACACCAATAA   3600
CTTCACCCTG  ATGGTCAATG  ATGCTTACGG  TATTAAATCC  AATATCGTTC  GCGTGACCAC   3660
ACCAGGGAAA  CCTAACGACC  CAGACAACCC  AAGCAACAAC  TACATCACCC  CGCACAAGGT   3720
CAACAAGAAT  GAAAACGGTG  TGGTGATTGA  TGGTAAGTCC  GTCCTAGCTG  GTACCACCAA   3780
CTACTATGAA  TTGACTTGGG  ACCTGGACCA  ATACAAGGGC  GATAAATCGG  CCAAGGAGAC   3840
CATCCAAAAA  GGCTTCTTCT  ATGTGGATGA  CTATCCTGAA  GAAGCGCTGG  ACTTGCGCAC   3900
CGACCTGATT  AAGCTGACCG  ATGCCAACGG  CAAGGCGGTC  ACTGGTGTCA  GCGTGGCTGA   3960
CTACGCCAGT  CTGGAGGCCG  CACCAGCAGC  TGTTCAAGAC  ATGCTCAAGA  AGGCCAACAT   4020
TACCCCTAAG  GGAGCCTTCC  AAGTCTTTAC  CGCTGACGAT  CCTCAGGCCT  TCTACGATGC   4080
CTATGTGGTT  ACCGGAACTG  ACCTGACCAT  CGTCACTCCA  ATGACGGTCA  AGGCTGAGAT   4140
GGGCAAGATC  GGTGGTAGCT  ATGAAAACAA  GGCCTACCAG  ATTGACTTTG  GTAATGGCTA   4200
TGAATCTAAT  ATTGTGATTA  ACAATGTGCC  GCAAATCAAT  CCTGAAAAGG  ATGTGACCTT   4260
GACCATGGAT  CCAGCGGATA  GTACCAATGT  GGATGGACAG  ACCATCGCCC  TCAATCAGGT   4320
```

```
CTTTAACTAC  CGTCTCATCG  GTGGTATCAT  TCCAGCGGAC  CATGCCGAAG  AGCTCTTTGA      4380

GTACAGCTTT  AGCGATGACT  ATGACCAAAC  TGGAGACCAG  TACACGGGCC  AATACAAGGC      4440

CTTTGCCAAG  GTTGACCTGA  CCCTCAAGGA  TGGTACAATC  ATCAAGGCGG  GTACTGACTT      4500

GACTTCATAT  ACAGAAGCGC  AAGTTGATGA  AGCTAATGGC  CAAATTGTTG  TGACCTTCAA      4560

GGAAGATTTC  TTGCGGTCTG  TGTCTGTAGA  CTCGGCCTTC  CAAGCGGAAG  TCTACCTACA      4620

GATGAAGCGG  ATAGCCGTCG  GGACCTTTGC  CAATACCTAT  GTCAATACGG  TCAATGGAAT      4680

TACCTATAGC  TCTAATACGG  TAAGGACCAG  CACACCAGAG  CCGAAGCAGC  CAAGTCCAGT      4740

GGTACCTAAG  ACCACTACTA  CGGTAGTCTT  CCAGCCTCGT  CAGGGTCAAG  CTTATCAGCC      4800

AGCGCCGCCA  GCAGGAGCTC  AATTGCCAGC  CACAGGGGAT  AGTAGCAATG  CTTACCTGCC      4860

ACTTTTAGGC  CTCGTAAGCC  TGACTGCTGG  CTTTAGCCTG  TTAGGACTGC  GCCGGAAGCA      4920

GGACTAAAGA  ATCCAACAAG  AAAAAATGGG  AAAGTTTGCC  TTTCTCATTT  TTTATATTCC      4980

CAGCTAGCTG  AGTAGTCAAG  AAGTACTCTT  AGAAAACCCT  AGAGAACATT  AGCTAACTTT      5040

TCCAAACCGA  TAGACGTTTA  TTTTAGTCTA  AGTATGG                                 5077
```

( 2 ) INFORMATION FOR SEQ ID NO:23:

( i ) SEQUENCE CHARACTERISTICS:
        ( A ) LENGTH: 1566 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Streptococcus sobrinus ( x i ) SEQUENCE DESCRIPTION: SEQ ID NO:23:

```
Met  Gln  Arg  Lys  Glu  Thr  Phe  Gly  Phe  Arg  Lys  Ser  Lys  Ile  Ser  Arg
 1                 5                      10                       15

Thr  Leu  Cys  Gly  Ala  Leu  Leu  Gly  Thr  Ala  Ile  Leu  Ala  Ser  Val  Thr
               20                      25                       30

Gly  Gln  Lys  Ala  Leu  Ala  Glu  Glu  Thr  Ser  Thr  Thr  Ser  Thr  Ser  Gly
              35                      40                       45

Val  Asn  Thr  Ala  Val  Val  Gly  Thr  Glu  Thr  Gly  Asn  Pro  Ala  Thr  Asn
          50                      55                       60

Leu  Pro  Asp  Lys  Gln  Asp  Asn  Pro  Ser  Ser  Gln  Ala  Glu  Thr  Ser  Gln
 65                      70                      75                       80

Ala  Gln  Ala  Gly  Gln  Lys  Thr  Gly  Ala  Met  Ser  Val  Asp  Val  Ser  Thr
                    85                      90                       95

Ser  Glu  Leu  Asp  Glu  Ala  Ala  Lys  Ser  Ala  Gln  Glu  Ala  Gly  Val  Thr
              100                    105                      110

Val  Ser  Gln  Asp  Ala  Thr  Val  Asp  Lys  Gly  Thr  Val  Glu  Thr  Ser  Asp
              115                    120                      125

Glu  Ala  Asn  Gln  Lys  Glu  Thr  Glu  Ile  Lys  Asp  Tyr  Ser  Lys  Gln
         130                    135                      140

Ala  Ala  Asp  Ile  Gln  Lys  Thr  Thr  Glu  Asp  Tyr  Lys  Ala  Ala  Val  Ala
145                      150                     155                      160

Arg  Asn  Gln  Ala  Glu  Thr  Asp  Arg  Ile  Thr  Gln  Glu  Asn  Ala  Ala  Lys
```

|     |     |     |     | 165 |     |     |     | 170 |     |     |     | 175 |     |
|---|---|---|---|---|---|---|---|---|---|---|---|---|---|
| Lys | Ala | Gln | Tyr<br>180 | Glu | Gln | Asp | Leu | Ala<br>185 | Asn | Lys | Ala | Glu<br>190 | Val | Glu |
| Arg | Ile | Thr<br>195 | Asn | Glu | Asn | Ala | Gln<br>200 | Arg | Lys | Ala | Asp | Tyr<br>205 | Glu | Ala | Lys |
| Leu | Ala | Gln | Tyr<br>210 | Gln | Lys | Asp<br>215 | Leu | Ala | Ala | Val | Gln<br>220 | Gln | Ala | Asn | Asn |
| Asp<br>225 | Ser | Gln | Ala | Ala | Tyr<br>230 | Ala | Ala | Ala | Lys | Glu<br>235 | Ala | Tyr | Asp | Lys | Glu<br>240 |
| Leu | Ala | Arg | Val | Gln<br>245 | Ala | Ala | Asn | Ala | Ala<br>250 | Lys | Lys | Glu | Tyr<br>255 | Glu |
| Glu | Ala | Leu | Ala<br>260 | Ala | Asn | Thr | Thr | Lys<br>265 | Asn | Glu | Gln | Ile | Lys<br>270 | Ala | Glu |
| Asn | Ala | Ala<br>275 | Ile | Gln | Gln | Arg | Asn<br>280 | Ala | Gln | Ala | Lys | Ala<br>285 | Asp | Tyr | Glu |
| Ala | Lys<br>290 | Leu | Ala | Gln | Tyr | Glu<br>295 | Lys | Asp | Leu | Ala | Ala<br>300 | Ala | Gln | Ser | Gly |
| Asn<br>305 | Ala | Thr | Asn | Glu | Ala<br>310 | Asp | Tyr | Gln | Ala | Lys<br>315 | Lys | Ala | Ala | Tyr | Glu<br>320 |
| Gln | Glu | Leu | Ala | Arg<br>325 | Val | Gln | Ala | Ala | Asn<br>330 | Ala | Ala | Ala | Lys | Gln<br>335 | Ala |
| Tyr | Glu | Gln | Ala<br>340 | Leu | Ala | Ala | Asn | Thr<br>345 | Ala | Lys | Asn | Ala | Gln<br>350 | Ile | Thr |
| Ala | Glu | Asn<br>355 | Glu | Ala | Ile | Gln | Gln<br>360 | Arg | Asn | Ala | Gln | Ala<br>365 | Lys | Ala | Asn |
| Tyr | Glu<br>370 | Ala | Lys | Leu | Ala | Gln<br>375 | Tyr | Gln | Lys | Asp | Leu<br>380 | Ala | Ala | Ala | Gln |
| Ser<br>385 | Gly | Asn | Ala | Ala | Asn<br>390 | Glu | Ala | Asp | Tyr | Gln<br>395 | Glu | Lys | Leu | Ala | Ala<br>400 |
| Tyr | Glu | Lys | Glu | Leu<br>405 | Ala | Arg | Val | Gln | Ala<br>410 | Ala | Asn | Ala | Ala | Ala<br>415 | Lys |
| Gln | Glu | Tyr | Glu<br>420 | Gln | Lys | Val | Gln | Glu<br>425 | Ala | Asn | Ala | Lys | Asn<br>430 | Ala | Glu |
| Ile | Thr | Glu<br>435 | Ala | Asn | Arg | Ala | Ile<br>440 | Arg | Glu | Arg | Asn | Ala<br>445 | Lys | Ala | Lys |
| Thr | Asp<br>450 | Tyr | Glu | Leu | Lys | Leu<br>455 | Ser | Lys | Tyr | Gln | Glu<br>460 | Glu | Leu | Ala | Gln |
| Tyr<br>465 | Lys | Lys | Asp | Leu | Ala<br>470 | Glu | Tyr | Pro | Ala | Lys<br>475 | Leu | Gln | Ala | Tyr | Gln<br>480 |
| Asp | Glu | Gln | Ala | Ala<br>485 | Ile | Lys | Ala | Ala | Leu<br>490 | Glu | Glu | Leu | Glu | Lys<br>495 | His |
| Lys | Asn | Glu | Asp<br>500 | Trp | Asn | Leu | Ser | Glu<br>505 | Pro | Ser | Ala | Gln | Ser<br>510 | Leu | Val |
| Tyr | Asp | Leu<br>515 | Glu | Pro | Asn | Ala | Gln<br>520 | Ile | Ser | Leu | Val | Thr<br>525 | Asp | Trp | Lys |
| Leu | Leu<br>530 | Lys | Ala | Ser | Ser | Leu<br>535 | Asp | Glu | Ser | Phe | Ser<br>540 | His | Asp | Thr | Glu |
| Gln<br>545 | Tyr | Asn | Lys | His | Asn<br>550 | Leu | Gln | Pro | Asp | Asn<br>555 | Leu | Asn | Ile | Thr | Tyr<br>560 |
| Leu | Glu | Gln | Ala | Asp<br>565 | Asp | Val | Ala | Ser | Ser<br>570 | Val | Glu | Leu | Phe | Gly<br>575 | Asn |
| Phe | Gly | Asp | Lys<br>580 | Ala | Gly | Trp | Thr | Thr<br>585 | Thr | Val | Ser | Asn | Gly<br>590 | Ser | Glu |

```
Val Lys Phe Ala Ser Val Leu Leu Lys Arg Gly Gln Ser Ala Thr Ala
    595             600                 605
Thr Tyr Thr Asn Leu Lys Asn Ser Tyr Tyr Asn Gly Lys Lys Ile Ser
    610             615                 620
Lys Val Val Tyr Lys Tyr Thr Val Asp Pro Asp Ser Lys Phe Gln Asn
625             630                 635                 640
Pro Thr Gly Asn Val Trp Leu Gly Ile Phe Thr Asp Pro Thr Leu Gly
                645                 650                 655
Val Phe Ala Ser Ala Tyr Thr Gly Gln Asn Glu Lys Asp Thr Ser Ile
                660             665                 670
Phe Ile Lys Asn Glu Phe Thr Phe Tyr Asp Glu Asp Gly Asn Pro Ile
            675             680                 685
Asp Phe Asp Asn Ala Leu Leu Ser Val Ala Ser Leu Asn Arg Glu His
    690                 695                 700
Asn Ser Ile Glu Met Ala Lys Asp Tyr Ser Gly Thr Phe Val Lys Ile
705             710                 715                 720
Ser Gly Ser Ser Ile Gly Glu Lys Asn Gly Met Ile Tyr Ala Thr Asp
                725                 730                 735
Thr Leu Asn Phe Lys Lys Gly Glu Gly Ser Leu His Thr Met Tyr
                740                 745                 750
Thr Arg Ala Ser Glu Pro Gly Ser Gly Trp Asp Ser Ala Asp Ala Pro
        755                 760                 765
Asn Ser Trp Tyr Gly Ala Gly Ala Val Arg Met Ser Gly Pro Asn Asn
    770                 775                 780
Tyr Ile Thr Leu Gly Ala Thr Ser Ala Thr Asn Val Leu Ser Leu Ala
785                 790                 795                 800
Glu Met Pro Gln Val Pro Gly Lys Asp Asn Thr Ala Gly Lys Lys Pro
                805                 810                 815
Asn Ile Trp Tyr Ser Leu Asn Gly Lys Ile Arg Ala Val Asn Val Pro
                820                 825                 830
Lys Val Thr Lys Glu Lys Pro Thr Pro Pro Val Glu Pro Thr Lys Pro
            835                 840                 845
Asp Glu Pro Val Tyr Glu Val Glu Lys Glu Leu Val Asp Leu Pro Val
    850                 855                 860
Glu Pro Ser Tyr Glu Lys Glu Pro Thr Pro Ser Lys Thr Pro Asp
865                 870                 875                 880
Gln Asn Ile Pro Asp Lys Pro Val Glu Pro Thr Tyr Glu Val Glu Lys
                885                 890                 895
Glu Leu Glu Pro Ala Pro Val Glu Pro Ser Tyr Glu Lys Glu Pro Thr
                900                 905                 910
Pro Pro Ser Lys Thr Pro Asp Gln Ala Ile Pro Asp Lys Pro Val Glu
            915                 920                 925
Pro Thr Tyr Glu Val Glu Lys Glu Leu Glu Pro Val Pro Val Glu Thr
    930                 935                 940
Asn Tyr Glu Lys Glu Pro Thr Pro Pro Gln Ser Thr Pro Asp Gln Glu
945                 950                 955                 960
Glu Pro Thr Lys Pro Val Glu Pro Ser Tyr Gln Ser Leu Pro Thr Pro
                965                 970                 975
Pro Val Ala Pro Thr Tyr Glu Lys Val Pro Gly Pro Val Ser Val Pro
                980                 985                 990
Thr Val Arg Tyr His Tyr Tyr Lys Leu Ala Val Gln Pro Gly Val Thr
        995                 1000                1005
Lys Lys Ile Lys Asn Gln Asp Asp Leu Asp Ile Asp Lys Thr Leu Val
        1010                1015                1020
```

-continued

```
Ala Lys Gln Ser Thr Val Lys Phe Gln Leu Lys Thr Ala Asp Leu Pro
1025                1030                1035                1040

Ala Gly Arg Pro Glu Thr Thr Ser Phe Val Leu Met Asp Pro Leu Pro
                1045                1050                1055

Ser Gly Tyr Gln Leu Asn Leu Glu Ala Thr Lys Val Ala Ser Pro Gly
                1060                1065                1070

Phe Glu Ala Ser Tyr Asp Ala Met Thr His Thr Val Thr Phe Ile Ala
            1075                1080                1085

Thr Ala Glu Thr Leu Ala Ala Leu Asn Gln Asp Leu Thr Lys Ala Val
            1090                1095                1100

Ala Thr Ile Tyr Pro Thr Val Val Gly Gln Val Leu Asn Asp Gly Ala
1105                1110                1115                1120

Thr Tyr Thr Asn Asn Phe Thr Leu Met Val Asn Asp Ala Tyr Gly Ile
                1125                1130                1135

Lys Ser Asn Ile Val Arg Val Thr Thr Pro Gly Lys Pro Asn Asp Pro
                1140                1145                1150

Asp Asn Pro Ser Asn Asn Tyr Ile Thr Pro His Lys Val Asn Lys Asn
            1155                1160                1165

Glu Asn Gly Val Val Ile Asp Gly Lys Ser Val Leu Ala Gly Thr Thr
            1170                1175                1180

Asn Tyr Tyr Glu Leu Thr Trp Asp Leu Asp Gln Tyr Lys Gly Asp Lys
1185                1190                1195                1200

Ser Ala Lys Glu Thr Ile Gln Lys Gly Phe Phe Tyr Val Asp Asp Tyr
                1205                1210                1215

Pro Glu Glu Ala Leu Asp Leu Arg Thr Asp Leu Ile Lys Leu Thr Asp
                1220                1225                1230

Ala Asn Gly Lys Ala Val Ala Gly Val Ser Val Ala Asp Tyr Ala Ser
            1235                1240                1245

Leu Glu Ala Ala Pro Ala Ala Val Gln Asp Met Leu Lys Lys Ala Asn
            1250                1255                1260

Ile Thr Pro Lys Gly Ala Phe Gln Val Phe Thr Ala Asp Asp Pro Gln
1265                1270                1275                1280

Ala Phe Tyr Asp Ala Tyr Val Val Thr Gly Thr Asp Leu Thr Ile Val
            1285                1290                1295

Thr Pro Met Thr Val Lys Ala Glu Met Gly Lys Ile Gly Gly Ser Tyr
            1300                1305                1310

Glu Asn Lys Ala Tyr Gln Ile Asp Phe Gly Asn Gly Tyr Glu Ser Asn
            1315                1320                1325

Ile Val Ile Asn Asn Val Pro Gln Ile Asn Pro Glu Lys Asp Val Thr
    1330                1335                1340

Leu Thr Met Asp Pro Ala Asp Ser Thr Asn Val Asp Gly Gln Thr Ile
1345                1350                1355                1360

Ala Leu Asn Gln Val Phe Asn Tyr Arg Leu Ile Gly Gly Ile Ile Pro
                1365                1370                1375

Ala Asp His Ala Glu Glu Leu Phe Glu Tyr Ser Phe Ser Asp Asp Tyr
            1380                1385                1390

Asp Gln Thr Gly Asp Gln Tyr Thr Gly Gln Tyr Lys Ala Phe Ala Lys
            1395                1400                1405

Val Asp Leu Thr Leu Lys Asp Gly Thr Ile Ile Lys Ala Gly Thr Asp
        1410                1415                1420

Leu Thr Ser Tyr Thr Glu Ala Gln Val Asp Glu Ala Asn Gly Gln Ile
1425                1430                1435                1440

Val Val Thr Phe Lys Glu Asp Phe Leu Arg Ser Val Ser Val Asp Ser
```

|   |   |   |   |   |   |   |   |   |   |   |   |   |   |   |
|---|---|---|---|---|---|---|---|---|---|---|---|---|---|---|
| | | | | 1445 | | | | 1450 | | | | 1455 | | |
| Ala | Phe | Gln | Ala | Glu | Val | Tyr | Leu | Gln | Met | Lys | Arg | Ile | Ala | Val | Gly |
| | | | 1460 | | | | | 1465 | | | | 1470 | | |
| Thr | Phe | Ala | Asn | Thr | Tyr | Val | Asn | Thr | Val | Asn | Gly | Ile | Tyr | Tyr | Ser |
| | | 1475 | | | | 1480 | | | | | | 1485 | | |
| Ser | Asn | Thr | Val | Arg | Thr | Ser | Thr | Pro | Glu | Pro | Lys | Gln | Pro | Ser | Pro |
| | 1490 | | | | | 1495 | | | | 1500 | | | | |
| Val | Val | Pro | Lys | Thr | Thr | Thr | Thr | Val | Val | Phe | Gln | Pro | Arg | Gln | Gly |
| 1505 | | | | | 1510 | | | | | 1515 | | | | 1520 |
| Gln | Ala | Tyr | Gln | Pro | Ala | Pro | Pro | Ala | Gly | Ala | Gln | Leu | Pro | Ala | Thr |
| | | | | 1525 | | | | | 1530 | | | | | 1535 |
| Gly | Asp | Ser | Ser | Asn | Ala | Tyr | Leu | Pro | Leu | Leu | Gly | Leu | Val | Ser | Leu |
| | | | | 1540 | | | | 1545 | | | | | 1550 | |
| Thr | Ala | Gly | Phe | Ser | Leu | Leu | Gly | Leu | Arg | Arg | Lys | Gln | Asp | | |
| | | | 1555 | | | | 1560 | | | | 1565 | | | |

DIAGNOSIS AND TREATMENT OF INFECTIONS DUE TO STREPTOCOCCI AND ENTEROCOCCI

This is a Continuation of International Appln. No. PCT/GB95/00186 filed Jan. 30, 1995.

This invention concerns the diagnosis, prophylaxis and treatment of infections due to Streptococci and Enterococci, especially endocarditis and septicaemia.

Endocarditis is commonly caused by Streptococcal and Enterococcal infection. These are bacterial species which grow in the heart valves of an infected patient and cause damage thereto. Endocarditis is currently diagnosed by clinical features, echocardiogram and the presence of heart murmurs. The causative microorganism is usually identified by blood culture (culture-positive endocarditis). However, in approximately 10% of infective endocarditis patients the blood culture is negative. This may lead to a wrong diagnosis and/or delayed treatment.

Active infective endocarditis in which blood cultures are negative has been a recognised clinical entity since the beginning of the century. Etiological factors involved in such culture-negative endocarditis include (1) previous antibiotic therapy, (2) fastidious, slow growing bacteria and (3) non-bacterial organisms.

Patients with rheumatic fever, damaged heart valves or prosthetic valves are at risk of a secondary Streptococcal infection leading to endocarditis when having routine dental or gastrointestinal procedures.

Additionally, a growing problem in recent years has been the spread of vancomycin-resistnt enterococci (VRE). The emergence of enterococci resistant to most or all licensed antibiotics leaves few treatment options and recent studies have shown that 36.6% of those patients with VRE in blood died as compared with 16.4% of those with vancomycin sensitive enterococci. Clearly a treatment for enterococci of all descriptions, and especially of VRE is extremely desirable.

One method of diagnosing endocarditis and, more particularly, culture-negative endocarditis, is by immunoblotting sera of such patients to reveal raised levels of antibodies against causative microorganisms and also a pattern on immunoblot which appears to be species specific (Clark & Burnie, J. Clin. Pathol. 1991, 44, 152–156; Burnie et al, J. Clin. Pathol, 1987, 40: 1149–1158; Burnie & Clark, J. Immunol. Methods, 1989, 123: 217–225). However, although individual species of both Streptococcus and Enterococcus can be identified, there is some cross- reaction between species making absolute diagnosis sometimes difficult. Immunoblotting is also cumbersome as well as expensive.

Current therapy of both culture-positive and culture-negative endocarditis involves antibiotics, however, some of the antibiotics necessary to treat endocarditis are highly toxic, for example, vancomycin and gentamicin may be nephrotoxic and ototoxic. Additionally, it is difficult to assess patient response to antibiotic treatment since, although the organism may no longer be viable, fever may persist.

The present invention provides a method of diagnosis and treatment ("treatment" from herein being taken to include prophylaxis) of infections due to Streptocci and Enterococci which is specific to both culture-positive and culture-negative endocarditis, thereby overcoming at least to some extent, the aforesaid problems.

Experiments were undertaken which resulted in the cloning, sequencing and characterisation of Streptococcal antigens, resulting in the determination of an antigen expressed during infection due to Streptococci and Enterococci, together with immunogenic fragments thereof which were found to be useful in the prophylaxis and treatment of infections due to both Streptococci and Enterococci.

According to the present invention there is provided a purified bacterial protein expressed during infection due to streptococci or Enterococci and isolated from human sera having at least the sequence of formula (1) (SEQ ID NO:1):

```
NH—          10                           30
   E F T F Y D E N D Q   P I N F D N A L L S   V A S L N R E H N S
                                50
   I E M A K D Y S G T   F I K I S G S S I G   E K N G M I Y A T E
                70                           90
   T L N F K Q G Q G G   A R W T M Y P N R Q   P G S G W D S S D A
                               110
   P N S W Y G A G A I   S M S G P T N H V T   V G A T S A T N V M
                130                          150
   S V A E M P Q V P G   R D N T E G K R P N   I W Y S L N G K I R
                               170
   A V D V P K I T K E   K P T P P V A P T E   P Q A P T Y E V E K
                190                          210
   P L E P A P V A P S   Y E N E P T P P V K   T P D Q P E P S K P
                               230
   E E P T Y E Y E K P   L E P A P V A P N Y   E N E P T P P V K T
                250                          270
   P D Q P D P S K P E   E P N Y E T E K P L   E P A P V A P S Y E
                               290
   N E P T P P V K T P   D Q P E P S K P E E   P N Y D P L P T P P
                310                          330
   L A P T P K Q L P T   P P A V P T V H F H   Y N R L F A Q P Q I
                               350
   N K E I K N E D G V   D I D R T L V A K Q   S V V K F E L K T E
                370                          390
   A L T A G R P K T T   S F V L V D P L P T   G Y Q F D L E A T K
                               410
   A A S K G F E T S Y   D K A S H T V T F K   A T E E T L A A F N
                430                          450
   A D L T K S F E T L   Y P T V V G R V L N   D G A T Y T N N F T
                               470
   L T V N D A T G V K   S N I V R V T T P G   K P N D P D N P N N
                490                          510
   N Y I K P L K V N K   N K Q G V N I D G K   E V L A G S T N Y Y
                               530
   E L T W D L D Q Y K   G D K S S K E A I Q   N G F Y Y V D D Y P
                550                          570
   E E A L T L Q P E L   V K I R D L E G N L   V S G I S V Q Q F D
                               590
   S L E R A P K K V Q   D L L K K A N I T V   K G A F Q L F S A D
                610
   N P A E F
``` or an immunogenic fragment thereof or an analogue thereof.

The single letters in formula (1) are each to be understood to represent a separate amino acid, and each is the conventional single letter symbol used for amino acids.

Bacterial protiens expressed during infection due to Streptococci or Enterococci according to the invention include those proteins wherein one or more amino acids in the sequence of formula (1) is replaced by another amino acid, providing that overall functionality of the protein is conserved.

A bacterial protein according to the invention may be further characterised by either one or both of the following features:

(1) It is an immunodominant conserved antigen; and
(2) Recombinant human antibody in an animal model (mouse) protected against septicaemia infection;

A bacterial protein according to the invention may also be characterised in that it is involved in binding to heart valves.

The bacterial protein may be obtained from one of the group of Streptococcus oralis, Streptococcus sobrinus, Streptococcus gordonii, Streptoccocus sanguis, Streptococcus mutans, Streptococcus mitis, Streptococcus mitior, Streptococcus parasanguis, Streptococcus bovis, Enterococcus faecalis and Enterococcus faecium.

Additionally, the bacterial protein may be obtained from either one of the group of vancomycin-resistant Enterococcus faecalis and Enterococcus faecium.

Particular fragments of a bacterial protein expressed during infection due to Streptococci or Enterococci include any peptide epitopes ("imnunogenic fragments"), for example, a few amino acids or analogues thereof. Examples of such epitopes include YEVEKPLEPAPVAPS (SEQ ID NO:3), SYENEPTPPVKTPD (SEQ ID NO:4), KTPDQPEPSKPEEPT (SEQ ID NO:5), EPAPVAPSYENEPTP (SEQ ID NO:6), YEVEKELVDLPVEPS (SEQ ID NO:7), KTPDQNIPDKPVEPT (SEQ ID NO:8), TMYPNRQPGSGWDSS (SEQ ID NO:9) and WYSLNGKIRAVDVPK (SEQ ID NO:10). Peptides of this type may be synthesised using conventional liquid or solid phase peptide synthesis techniques.

In a further aspect the invention particularly provides a recombinant bacterial protein expressed during infection due to Streptococci or Enterococci having an amino acid sequence which includes at least the sequence of formula (1) or an immunogenic fragment thereof, or an analogue thereof.

As mentioned earlier, current treatment of endocarditis is by antibiotics and recovery is often difficult to assess as fever may persist after other symptoms have been relieved. Tests currently available to measure the efficiency of antibiotic treatment, for example, minimum inhibitory concentration, minimum bactericidal concentrations and back titrations, measure only organism sensitivity not actual organism death in the patient. We show for the first time, as detailed below, that in patients with endocarditis due to Streptococcus oralis, S. gordonii, S. sanguis and S. mitis and undergoing antibiotic therapy, resolution of the disease was accompanied by at least a 50% drop in IgM titre within two weeks. This provides a direct marker of successful antibiotic therapy showing for the first time a direct marker of pathogen kill. Since the IgM antibody is specific to endocarditis it can be used in the diagnosis of both culture-positive and, more particularly, culture-negative endocarditis.

Thus the present invention also provides a method of diagnosis of culture-positive and culture-negative endocarditis using IgM antibody to a bacterial protein expressed during infection due to Streptococci or Enterococci, said bacterial protein, and therefore IgM antibody raised thereto, falling by 50% within two weeks after commencement of antibiotic treatment, thereby acting as a marker of pathogen kill.

In another use the bacterial protein according to the present invention may be employed, using conventional techniques, for screening to obtain activity inhibiting agents for use in the prophylaxis and treatment due to Streptococci or Enterococci and in particular of culture-positive and culture-negative endocarditis-causing bacterial infection. Such screening methods forms a further aspect of the invention.

In a further use, the bacterial protein according to the invention is particularly well suited for the generation of antibodies. Thus according to a further aspect of the invention we provide a bacterial protein expressed during infection due to Streptococci or Enterococci having an amino acid sequence which includes at least the sequence of formula (1) or an immunogenic fragment thereof or an analogue thereof, for use as an immunogen.

Standard immunological techniques may be employed with the bacterial protein in order to use it as an imunogen. Thus, for example, any suitable host may be injected with the protein and the serum collected to yield the desired polyclonal anti-bacterial protein antibody after purification and/or concentration. Prior to injection of the host the bacterial protein may be formulated in a suitable vehicle and thus according to a further aspect of the invention we provide a composition comprising a bacterial protein expressed during infection due to Streptococci or Enterococci and having an amino acid sequence which includes at least the sequence of formula (1) or an analogue thereof together with a pharmaceutically acceptable carrier, diluent or excipient.

For purification of any anti-bacterial protein antibody, use may be made of affinity chromatography employing an immobilised bacterial protein of the present invention as the affinity medium. Thus according to another aspect of the invention we provide a bacterial protein expressed during infection due to Streptococci or Enterococci having an amino acid sequence which includes at least the sequence of formula (1), or an immunogenic fragment thereof or an analogue thereof, covalently bound to an insoluble support.

Various derivatives of the bacterial protein or fragment or analogue may be used to inhibit said protein, fragment or analogue. The use of the bacterial protein expressed during infection according to the invention as imnmunogens for the production of antibodies generates one type of inhibitor of the action of the protein. Generally, inhibitors of the bacterial protein are potentially useful in the diagnosis, and in particular the prevention and treatment, of infections due to Streptococci or Enterococci and in particular of both culture-positive and culture-negative endocarditis, and provide a further feature of the invention. Inhibitors include any antagonists of the action of the bacterial protein expressed during infection or agents which prevent their production, and in particular those which may be used in treatment of endocarditis-causing bacterial infections. Suitable inhibitors include, for example, pharmaceutical reagents, including antibodies, and chemical analogues of the bacterial protein expressed during infection to antagonise the action of the bacterial protein, and anti-sense RNA and DNA to prevent production of the bacterial protein. Suitable inhibitors may be determined using appropriate screens, for example, by measuring the ability of a potential inhibitor to antagonise the action of, or prevent the production of a bacterial protein expressed during infection due to Streptococci or Enterococci according to the invention or an immunogenic fragment thereof, or an analogue thereof, in a test model for example an animal model such as the mouse model.

It will also be appreciated that by suitable epitope mapping using conventional procedures[Geysen et al., J. Immunol. Methods, 102: 259–274 (1987); Hopp and Woods, PNAS USA, 78(6): 3824–3828 (1981); Novotny et al., PNAS USA, 83: 226–230 (1986)], peptide fragments of the bacterial protein expressed during infection may be identified which can be chemically synthesised. Synthetic peptide antigens of this type may be used to produce inhibitors e.g. to raise antibodies for use in diagnosis and/or therapy, as previously described, or to produce-antiseras, e.g. non-specific polyclonal antisera, for use as a vaccine, and as discussed above form a further aspect of the invention.

According to a further aspect of the invention we provide a derivative of a bacterial protein expressed during infection due to Streptococci or Enterococci, said protein having an amino acid sequence which includes at least the sequence of formula (1) or an immunogenic fragment thereof or an analogue thereof, wherein the derivative inhibits said protein, fragment or analogue.

Such inhibitors may be used either alone or where appropriate in combination with other pharmaceutical agents, for example, other antibiotics.

One particularly useful group of inhibitors according to this aspect of the invention are antibodies capable of recognising and binding to the bacterial proteins.

Thus according to yet another aspect of the invention we provide isolated and purified antibody specific for one or more epitopes of a bacterial protein expressed during infection due to Streptococci or Enterococci having an amino acid sequence which includes at least the sequence of formula (1) or an immunogenic fragment thereof or an analogue thereof.

The antibody may be a whole antibody or an antigen binding fragment thereof and may in general belong to any immunoglobulin class. Thus, for example, it may be an immunoglobulin M antibody or, in particular, an immunoglobulin G antibody. The antibody or fragment may be of animal, for example, mammalian origin and may be for example of murine, rat or human origin. It may be a natural antibody or a fragment thereof, or, if desired, a recombinant antibody fragment, ie., an antibody or antibody fragment which has been produced using recombinant DNA techniques.

Particular recombinant antibodies or antibody fragments include human recombinant antibodies and in particular include (1) those having an antigen binding site at least part of which is derived from a different antibody, for example those in which the hypervariable or complementarity determining regions of one antibody have been grafted into the variable framework regions of a second, different antibody (as described in European Patent Specification No 239400); (2) recombinant antibodies or fragments wherein non-Fv sequences have been substituted by non-Fv sequences from other, different antibodies (as described in European Patent Specification Nos 171469, 173494 and 194276); or (3) recombinant antibodies or fragments possessing substantially the structure of a natural immunoglobulin but wherein the hinge region has a different number of cysteine residues from that found in the natural immunoglobulin but wherein one or more cysteine residues in a surface pocket of the recombinant antibody or fragment is in the place of another amino acid residue present in the natural inununoglobulin (as described in International Patent Application Nos PCT/GB88/00730 and PCT/GB88/00729).

The antibody or antibody fragment may be of polyclonal, or preferably, monoclonal origin. It may be specific for a single epitope or for a number of epitopes associated with the bacterial protein.

Antigen binding antibody fragments include, for example, fragments derived by proteolytic cleavage of a whole antibody, such as F(ab')2, Fab' or Fab fragments, or fragments obtained by recombinant DNA techniques, for example Fv fragments (as described in International Patent Application No PCT/GB88/0747).

The antibodies according to the invention may be prepared using well-known immunological techniques employing the bacterial protein expressed during infection as antigen. Thus, for example, any suitable host may be injected with the bacterial protein and the serum collected to yield the desired polyclonal antibody after appropriate purification and/or concentration (for example by affinity chromatography using the immobilised bacterial protein as the affinity medium). Alternatively, splenocytes or lymphocytes may be recovered from the bacterial protein-injected host and immortalised using for example the method of Kohler et al, Eur. J. Immunol. 6: 511, 1976, the resulting cells being segregated to obtain a single genetic line producing monoclonal anti-streptococcal or -enterococcal bacterial protein antibodies. Antibody fragments may be produced using conventional techniques, for example, by enzymatic digestion with pepsin or papain. Where it is desired to produce recombinant antibodies according to the invention these may be produced using for example the methods described in European Patent Specification Nos 171469, 173494, 194276 and 239400.

Antibodies according to the invention may be labelled with a detectable label or may be conjugated with effector molecule for example a drug eg. an antibacterial agent or a toxin or an enzyme, using conventional procedures and the invention extends to such labelled antibodies or antibody conjugates.

The antibodies according to the invention have a diagnostic and/or preventative and/or therapeutic use. Thus for diagnostic use the antibodies may be employed to detect whether the bacterial protein is present in a host organism, to confirm whether the host has a particular Streptococcal or Enterococcal bacterial infection, and especially to test for the presence of such organisms in culture-negative endocarditis, and/or to monitor the progress of therapeutic treatment of such infections. Diagnostic methods of this type form a further aspect of the invention and may generally employ standard techniques, for example, immunological methods such as enzyme-linked immunosorbent methods, radioimnmuno methods, latex agglutination methods or immunoblotting methods.

Antibodies according to the invention also have a therapeutic use in the treatment of bacterial infection due to Streptococci or Enterococci, for example, those just described and may be used alone or conjugated to an effector molecule, in the latter case to target the effector molecule, eg an antibacterial agent, to the infecting organism. For therapeutic use the antibody may be formulated in accordance with conventional procedures, for example, with a pharmaceutically acceptable carrier or excipient, eg., isotonic saline for the administration at an appropriate dosage, depending on the nature of the infection to be treated and the age of the patient.

If desired, mixtures of antibodies may be used for diagnosis and/or prevention and/or treatment, for example mixtures of two or more antibodies recognising different epitopes of a bacterial protein according to the invention, and/or mixtures of antibodies of a different class, eg., mixtures of IgG and IgM antibodies recognising the same or different epitope(s) of a bacterial protein of the invention.

The protein or any fragment, analogue, inhibitor, antibody or antigen binding fragment thereof according to the invention may be used in a method if treatment or diagnosis of the human or animal body.

The diagnostic test method may be selected from one of the group of enzyme-linked immunosorbent assay, radioimmunoassay, latex agglutination assay and immunoblot assay.

Such a protein, fragment, analogue, inhibitor, antibody or antigen binding fragment may form part of a composition for use in a method of diagnosis or treatment of the human or animal body together with a pharmaceutically acceptable carrier, diluent or excipient.

The bacterial proteins according to the invention may be prepared by a variety of processes, for example, by protein fractionation from appropriate bacterial cell extracts, using conventional separation techniques such as ion exchange and gel chromatography and electrophoresis, or by the use of recombinant DNA techniques, as more particularly described in the "Experiments" section hereinafter. The use of recombinant DNA techniques is particularly suitable for preparing substantially pure bacterial proteins according to the invention.

Thus according to a further aspect of the invention we provide a process for the production of a bacterial protein expressed during infection due to Streptococci or Enterococci having an amino acid sequence which includes at least the sequence of formula (1) or a fragment or an analogue thereof, comprising the steps of (1) culturing a host organism transformed with a vector including a gene coding for a precursor of said protein and (2) recovering said protein.

Preferably the precursor cleaved in this aspect of the invention is a fusion protein comprising at least a portion of a protein produced in a transformed host organism and at least the amino acid sequence of formula (1). Such fusion proteins form a further aspect of the invention. Desirably the fusion protein includes a protein produced at a high level by a transformed host organism. Suitable such proteins include at least a portion of a chloramphenicol acetyltransferase (CAT) protein or, preferably at least a portion of the B-galactosidase protein.

According to a still further aspect of the invention we provide a DNA sequence coding for a bacterial protein or an immunogenic fragment or an analogue thereof expressed during infection due to Streptococci or Enterococci having substancially the nucleotide sequence of formula (2) (SEQ ID NO:2):

```
5'         10                      30                      50
    GAATTCACCT TCTACGATGA AAATGACCAA CCAATTAATT TTGACAATGC TCTTCTTTCA 70                      90                     110
    GTAGCCTCAC TTAACCGTGA GCATAACTCT ATTGAGATGG CTAAGGATTA TAGTGGTACT 130                     150                     170
    TTTATTAAAA TCTCAGGTTC ATCCATCGGT GAAAAAAATG GCATGATTTA TGCCACAGAA 190                     210                     230
    ACCCTGAACT TTAAACAAGG ACAGGGTGGA GCTCGCTGGA CAATGTATCC AAATCGTCAG 250                     270                     290
    CCAGGTTCAG GTTGGGATTC ATCAGATGCA CCAAACTCTT GGTACGGTGC AGGGGCCATT 310                     330                     350
    AGTATGTCCG GTCCTACGAA TCACGTTACA GTTGGTGCAA CATCTGCTAC CAATGTGATG 370                     390                     410
    TCCGTAGCAG AAATGCCTCA AGTACCTGGA AGAGACAATA CTGAAGGTAA AAGACCAAAC 430                     450                     470
    ATCTGGTACT CACTCAATGG TAAAATTCGT GCGGTTGACG TTCCGAAAAT TACAAAAGAA 490                     510                     530
    AAACCAACTC CACCGGTAGC ACCAACTGAA CCACAAGCTC CTACCTATGA AGTGGAGAAA 550                     570                     590
    CCACTGGAAC CGGCTCCAGT AGCACCAAGC TACGAAAATG AGCCAACTCC ACCAGTAAAA 610                     630                     650
    ACTCCAGATC AACCGGAGCC ATCAAAACCA GAAGAGCCAA CATATGAGAC AGAGAAACCA 670                     690                     710
    TTGGAACCAG CTCCAGTAGC ACCAAACTAC GAAAATGAGC CAACTCCACC AGTAAAAACT 730                     750                     770
    CCAGATCAAC CAGACCCATC AAAACCGGAA GAGCCAAACT ATGAGACAGA GAAACCATTG 790                     810                     830
    GAACCAGCTC CAGTAGCACC AAGCTATGAA AATGAGCCAA CTCCACCGGT AAAAACTCCA 850                     870                     890
    GATCAACCAG AGCCATCAAA ACCAGAAGAG CCAAATTATG ATCCATTGCC AACTCCGCCG 910                     930                     950
    CTAGCACCAA CTCCTAAGCA GTTGCCAACA CCACCAGCGG TGCCAACAGT TCACTTCCAT 970                     990                    1010
    TACAATCGTC TATTTGCACA ACCTCAGATT AATAAAGAAA TTAAAAACGA GGATGGAGTA 1030                    1050                    1070
    GATATTGATC GTACTCTAGT TGCTAAGCAG TCTGTAGTGA AGTTTGAGCT GAAAACAGAA
```

-continued

```
        1090                     1110                      1130
GCTTTAACTG   CTGGTCGTCC   AAAAACAACT   TCGTTTGTAT   TGGTAGATCC   ACTTCCAACT 1150                     1170                      1190
GGCTATCAGT   TTGATTTGGA   AGCAACCAAG   GCTGCAAGCA   AAGGTTTTGA   AACAAGCTAT 1210                     1230                      1250
GACAAAGCTA   GTCACACTGT   AACCTTTAAG   GCTACTGAGG   AGACCTTAGC   TGCTTTCAAT 1270                     1290                      1310
GCTGATTTGA   CAAAATCCTT   TGAGACTCTA   TATCCAACTG   TTGTTGGTCG   TGTCTTGAAT 1330                     1350                      1370
GATGGGGCGA   CTTATACGAA   TAACTTTACA   TTGACAGTCA   ACGATGCTAC   TGGTGTCAAG 1390                     1410                      1430
TCAAACATTG   TTCGTGTAAC   GACTCCAGGT   AAACCAAATG   ATCCTGACAA   TCCAAATAAC 1450                     1470                      1490
AACTACATCA   AGCCTTTGAA   AGTTAACAAG   AACAAGCAAG   GTGTGAATAT   TGATGGCAAA 1510                     1530                      1550
GAAGTTCTAG   CTGGTTCAAC   GAACTACTAT   GAACTCACAT   GGGATTTGGA   TCAATACAAG 1570                     1590                      1610
GGAGATAAAT   CTTCTAAAGA   AGCGATTCAA   AATGGTTTCT   ACTATGTGGA   TGATTATCCA 1630                     1650                      1670
GAAGAAGCTT   TAACGCTTCA   ACCAGAATTG   GTTAAGATTC   GTGATCTAGA   GGGCAACCTT 1690                     1710                      1730
GTATCAGGTA   TCAGTGTTCA   ACAGTTTGAT   AGTTTAGAAC   GTGCGCCTAA   GAAGGTTCAA 1750                     1770                      1790
GATCTGTTGA   AGAAAGCAAA   CATCACTGTT   AAAGGTGCTT   TCCAACTCTT   CTCAGCTGAT

1810
AATCCAGCTG   AATTC
``` and homologues thereof.

A DNA sequence according to the invention may be further characterised in that the bacterial protein for which it encodes may be characterised by either one or both of the following features:

(1) It is an immunodominant conserved antigen; and
(2) Recombinant human antibody in an animal model (mouse) protected against septicaemia infection;

A DNA sequence may also be ferer characterised in that the protein for which it encodes is involved in binding to heart valves.

DNA with this sequence may be obtained from bacterial genomic DNA as described in the "Experiments" section hereinafter.

The DNA sequence according to this aspect of the invention may be incorporated in an expression vector using conventional techniques. Thus in a further aspect of the invention we provide an expression vector including substantially a DNA sequence of formula (2) or a homologue thereof.

The vector may be adapted for use in a given host cell by the provision of suitable selectable markers, promoters and other control regions as appropriate. Host cells transformed with such vectors form a farther aspect of the invention. Suitable host organisms include bacteria (eg. E.coli), and mammalian cells in tissue culture.

The DNA sequence of formula (2) may also be used to design DNA probes for use in identifyg the presence of Streptococcal and Enterococcal bacteria in the infected state and the invention extends to such DNA probes. Such probes may also be of use for detecting circulating bacterial nucleic acids, for example using a polymerase chain reaction, as a method of diagnosing such bacterial infections. The probe may also be synthesised using conventional techniques and may be immobilised on a solid phase, or may be labelled with a detectable label.

A DNA sequence, vector, probe or inhibitor according to the invention may be used in a method of treatment or diagnosis of the human or animal body.

It is known that Streptococci and Enterococci cause endocarditis by binding to heart valves and causing damage thereto. A possible mode of action of Streptococci in binding to heart valve tissue, or prosthetic valves, has been proposed to involve pre-binding of Steptococci to extracellular matrix proteins, such as fibronectin, which leads to the adherence and colonisation of bacteria to damaged valvular surfaces (Lowrance et al., J. Clin. Invest., 1990, 86: 7–13). This suggests that fibronectin acts as a tissue receptor for the bacteria. However, we show for the first time that the prior art theory on the role of fibronectin in endocarditis is incorrect. In our studies, described below, antibody against fibronectin binds to PAc and is neutralised by prior cross-absorption with fibronectin indicating that PAc acts like fibronectin binding to damaged heart valves directly, and not via fibronectin. This molecular mimicry is the probable mode of action of PAc.

Thus the invention also provides fibronectin or an inunu- nogenic fragment thereof or an analogue thereof or an antibody thereto or an antigen binding fragment thereof for use in a method of treatment or diagnosis of the human or animal body for infection due to Streptococci or Entero- cocci.

Additionally, as described below in the "Experiments" section, we have shown for the first time that serum from patients with endorcarditis due to S.oralis, S.gordonii and S.sanguis infection have antigen of approximately 85 kDa which reacts with a mouse monoclonal antibody specific to heat shock 90 molecules. We have also shown that in a mouse S. oralis infection model with death as an end point, antibody specific to HSP 90 shows a statistically significant increase in survival. This shows that this antigen is in the HSP 90 group. Thus antibodies against HSP 90 may be used for the diagnosis and treatment of infections caused by S.oralis, S.gordonii and S.sanguis.

Thus the present invention provides antibodies specific to HSP 90 or immunogenic fragments or analogues thereof for use in a method of diagnosis or treatment of the human or animal body of infection due to streptococci or Enterococci due to any one of the group of S.oralis, S.gordonii and S.sanguis.

BRIEF DESCRIPTION OF THE DRAWINGS

FIG. 8 shows short synthetic peptides covering the sequences of Streptococcus oralis and Streptococcus sobrinis.

FIG. 10 shows the gap alignment of the Streptococcus sobrinus antigenic region with the human fibronectin primary sequence. Fn Hum is the human fibronectin primary sequence homologous to the ESA STRSO peptin region. ESA STRSO is the proposed S. sobrinus endocaditis specific antigenic site. The numbers correspond to the amino acids of the complete human fibronectin primary sequence.

The invention will be further apparant from the following "Experiments" section which exemplifies the invention.

EXPERIMENTS

1. Characterisation of the Antibody Response

Sera was available from the following cases:

12 cases of septicaemia due to Streptococcus oralis, 14 cases of endocarditis due to Streptococcus gordonii, 2 cases of endocarditis due to Streptococcus oralis, 2 cases of endocarditis due to Streptococcus sanguis, 20 control sera from patients having no clinical evidence of endocarditis who were non-neutropenic, and 20 control sera from patients having no clinical evidence of endocarditis who were neutropenic.

2. Species Identification

Using the above sera, the causative organisms were identified, when available, according to the scheme of Beighton et al., J. Med. Microbiol., 1991, 35: 367–372. Specifically, isolates from 6 of the cases of S.oralis were available and identified as S.oralis by J M Hardie (personal communication). The others were aesculin-negative and raffinose-negative -viridans streptococci eliminating S.gordinii (100% aesculin positive), S.mitis (100% raffinose positive) and making it unlikely to be S.sanguis (75% aesculin positive and 75% raffinose positive). In the 14 cases of S.gordonii and 2 cases of S.sanguis endocarditis, isolates from 3 were positively identified as S.gordonii. All the other isolates were unobtainable but the original API Streptococcal profile showed they were aesculin positive. This would eliminate S.mitis and make it unlikely that they were S.oralis (18% aesculin positive). They were then subdivided into either S.gordonii or S.sanguis according to whether the more dominant IgM response on immunoblot was against S.gordonii or S.sanguis. The cases of S.oralis endocarditis were identified according to Beighton et al. 1991.

3. Source of Strains for Immunoblotting

Using the protocol outlined by Burnie et al., J. Clin. Pathol., 1987, 40: 1149–1158, antigenic extracts were made from S.sanguis NCTC 7863, S.oralis NCTC 7864 and S.gordinii NCTC 7868.

4. Immunolblotting

Immunoblotting using the above strains was then carried out as described in Burnie et al., 1987.

The results of immumoblots of the patients sera described above is summarised in Table 1 (S.oralis), Table 2 (S.gordonii) and Table 3 (S.sanguis) and in FIGS. 1 to 5.

Figure 1:
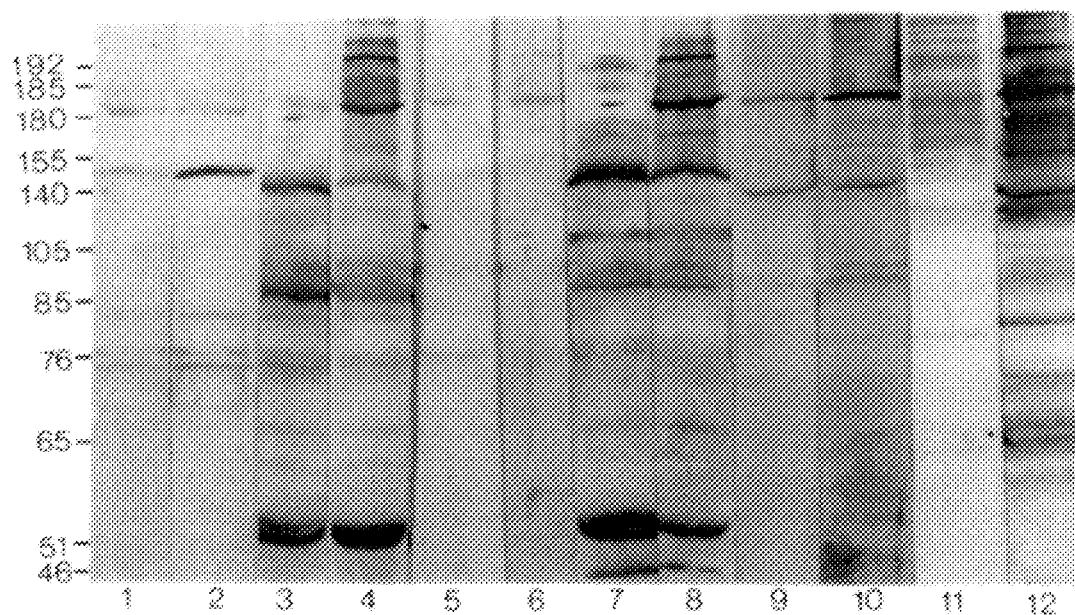
FIG. 1 shows the immunoblot of Streptococcus oralis septicaemias.

FIG. 1 shows the immunoblot for S.oralis septicaemias. Paired IgMs and paired IgGs covering pre and post sera from 3 of the cases showing the antibody changes.

Figure 2:
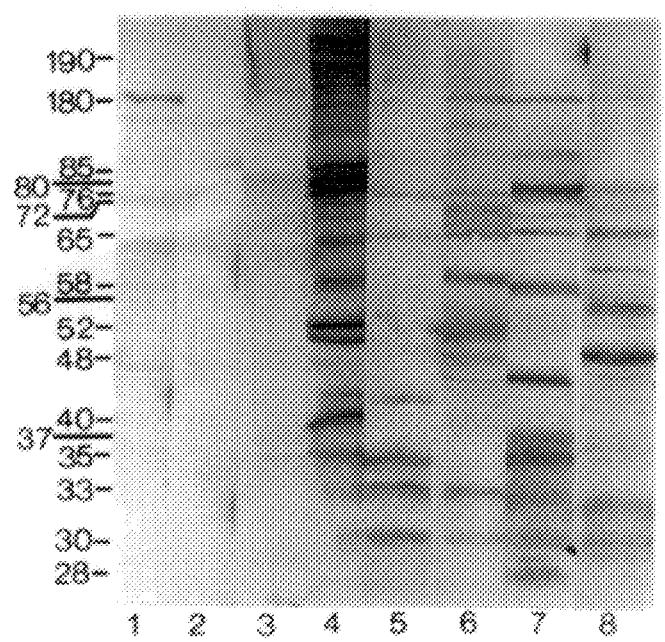
FIG. 2 shows the immunoblot of Streptococcus gordonii endocarditis.

FIG. 2 shows the immunoblot of S.gordonii endocarditis. Anti-fibronectin antibody against S.gordonii NCTC 7868 in Track 1, crossabsorbed against fibronectin in Track 2. Tracks 3–8 show IgM and IgG respectively in 3 cases of S. gordonii endocarditis.

Figure 3:
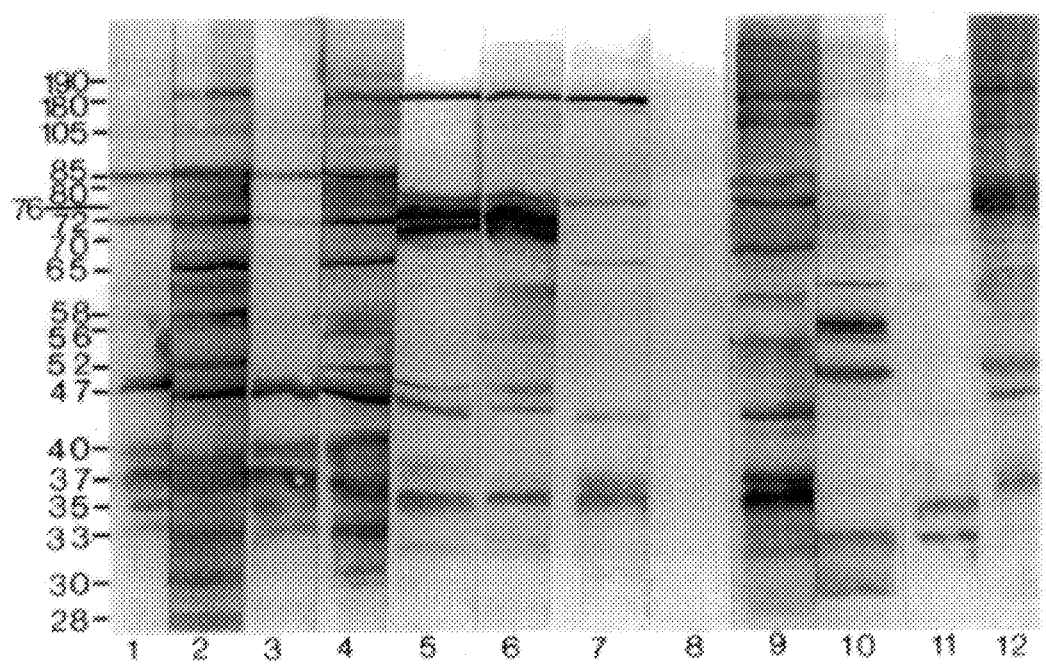
FIG. 3 compares immunoblots of Streptococcus gordonii endocarditis with S. gordonii antigen for five cases (Tracks 1/2, 3/4, 5/6, 9/10 and 11/12). Tracks 7/8 show pre-treatment of antibody levels of the case shown in tracks 9/10.

FIG. 3 shows 5 further case of S.gordonii endocarditis versus S.gordonii antigen Tracks 1/2, 3/4, 5/6, 9/10 and 11/12. Tracks 7/8 show pre-treatment of antibody levels of the same case as tracks 9/10 showing increased IgM to bands at approximately 85 KDa and IgG to bands at approximately 180, 58, 56 and 52 KDa.

Figure 4:
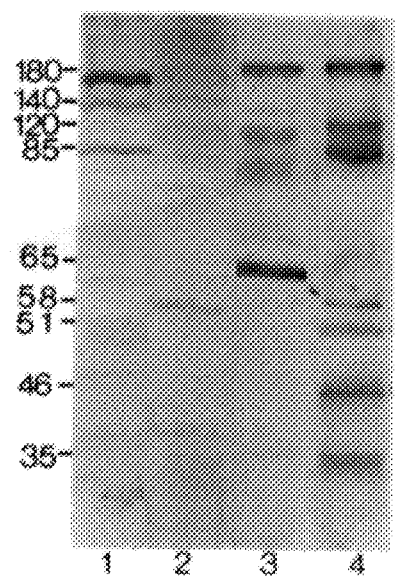
FIG. 4 shows the immunoblot of Streptococcus oralis endocarditis: IgM and IgG (Tracks 3/4), antifibronectin antibody cross reacting with 180 KDa band of S. oralis (Track 1), and effect of crossabsorption with fibronectin (Track 2).

FIG. 4 shows the immunoblot of S.oralis endocarditis, Tracks 3/4 IgM and IgG, antifibronectin antibody crossreacting with 180 KDa band of S.oralis, Track 1 and effect of crossabsorption with fibronectin, Track 2.

Figure 5:
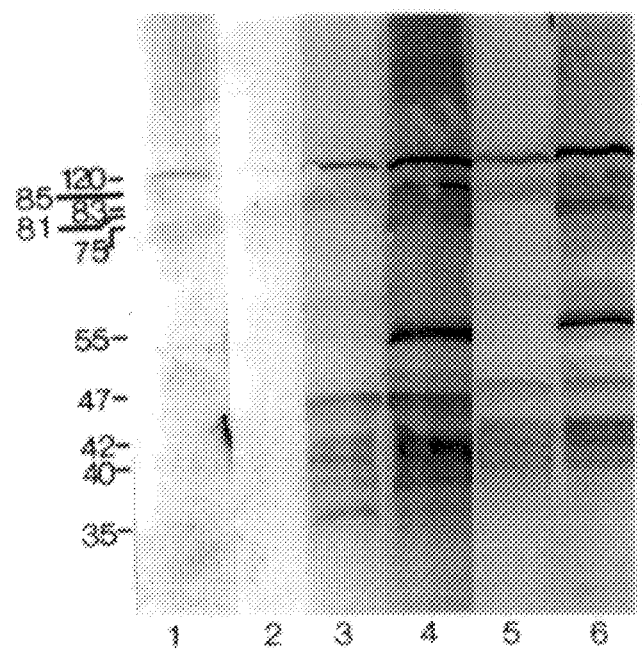
FIG. 5 shows the immunoblot of Streptococcus sanguis endocarditis: IgM (Tracks 3 and 5) and IgG (Tracks 4 and 6), antifibronectin antibody crossreacting with the 120 KDa band of S. sanguis (Track 1) and the effect of crossabsorption with fibronectin (Track 2).

FIG. 5 shows the immnunoblot of S.sanguis endocarditis, showing both IgM (track 3 and 5) and IgG (tracks 4 and 6) respectively of both cases, antifibronectin antibody crossreacting with the 120 KDa band of S.sanguis, Track 1 and the effect of crossabsorption with fibronectin, Track 2.

Comments (a) *S.oralis* septaceamia

IgM and/or IgG against band at approximately 180 KDa when recovering from infection.

(b) *S.gordonii* endocarditis

Additional IgG was detected against bands at approximately 185 (1 case), 165 (2 cases), 155 (1 case), 140 (1 case), 132 (1 case), 110 (1 case), 94 (1 case), 61 (1 case), 50 (1 case) and 45 KDa (1 case). Additional IgM was detected against the 45 KDa band (1 case). The majority of cases has IgM and all IgG against the bands at 85 and 180 KDa from *S.gordonii* NCTC 7868. Other immunodominant bands included those at approximately 65 and 47 KDa.

(c) *S.oralis* endocarditis case 1: Had additional antibody as follows. IgM against bands at approximately 180, 140 and 65 KDa and IgG agaist bands at approximately 180, 140, 120, 58, 51, 46 and 35 KDa. Both cases had IgM and IgG against the bands at 85 and 180 KDa from *S.oralis* NCTC 7864.

(d) *S.sanguis* endocarditis

Both patients produced antibody (IgM and IgG) against bands at approximately 120 and 85 KDa from *S.sanguis* NCTC 7863.

(e) *S.sobrinus/S.mutans* endocarditis

Immunoblotting demonstrated that patients with endocarditis had antibody (IgM and IgG) against three bands at approximately 185, 200 and 220 KDa.

Figure 6:
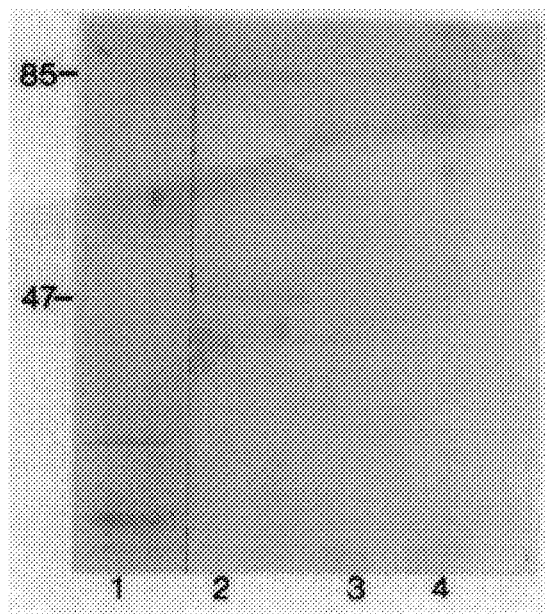
FIG. 6 shows immunoblots for Streptococcus oralis NCTC 7864 (Track 1), Streptococcus gordonii NCTC 7868 (Track 2), Streptococcus sanguis NCTC 7863 (Track 3), and the clinical isolate of Streptococcus oralis (Track 4).

Additionally the bands at 85 KDa (*S.oralis* NCTC 7864, *S.gordonii* NCTC 7868 and *S.sanguis* NCTC 7863) all react with a mouse monoclonal specific to heat shock 90 molecules (versus LKVIRK, see our previous patent application Nos WO 92/01717, WO 91/00351 and GB 2270076) showing that this molecule is in the HSP 90 group (FIG. 6), Track 1 *S.oralis* NCTC 7864, Track 2 *S.gordonii* NCTC 7868, Track 3 *S.sanguis* NCTC 7863, Track 4 clinical isolate of *S.oralis*.

5. Cloning of the immunodominant antigen of *S.sobrinus* and *S.oralis*

5.1 *S.sobrinus* cloning (i) DNA isolation and lambda ZAPII library preparation.

Strain *S.sobrinus* Manchester University Collection of Bacteria No.263 (MUCOB 263), was used as the source of *S.sobrinus*. Initially, the MUCOB 263 organism was identified as an *S.mutans*, a fact reflected in the aboved mentioned publication. However, a more detailed testing of theis strain revealed that MUCOB 263 is biochemically more similar to *S.sobrinus* (Professor D. Bratthall, personal communication). To avoid future confusion, the organism has now been renamed *S.sobrinus* MUCOB 263. Bacterial cells were grown overnight at 37° C., with shaking, in brain-heart infusion broth containing 0.2% glucose and 40 mM D,L-threonine (Sigma). The bacteria were harvested by spinning at 5,000 rpm for 10 mins before being washed, and resuspended in 12.5 ml of 0.02M Tris pH 8.2. Then 25 ml of 20M polyethylene glycol (PEG) 24% in distilled water was added and mixed. Lysozyme was added at 34.6 mg/ml equivalent to 100 μg/unit obtained by measuring the OD600 of a tenfold dilution of bacterial cultures. After 1 hour at 37° C., the spheroblasts formed were spun down at 5,000 rpm for 10 mins and thoroughly resuspended in 50 ml of 10 mM Tris-Cl pH 8.0, 1 mM EDTA (TE). The spheroblasts were lysed with 5.5 ml of 10% sodium dodecyl sulphate (SDS) at 60° C. for 15 mins. The DNA was purified by standard procedures (Maniatis et al., Molecular Cloning—A laboratory manual, 2nd edn. Cold Spring Harbour, N.Y., 1989), RNAase A (sigma) treated (after preboiling the RNAase at 100° C. for 15 mins), proteinase K treated, phenol:chloroform:isoamylalcohol (25:24:1) extracted, and ethanol precipitated. Plasmid DNA was removed by ethanol precipitation in the presence of 0.3M ammonium acetate pH 5.2. Further purification was obtained by dialysis against TE over 36 hrs at 4° C.

The DNA was mechanically sheared, EcoRI linkers added, fractionated and inserts ligated into lambda ZAPII vector arms. The library had an insert size range of 2 kb–7 kb.

(ii) Antibody Screening

Serum was taken from a patient with endocarditis and used for antibody screening. *Escherichia coli* XL1-Blue cells were infected at approximately 3,000 pfu/85 mm on L broth agar (Bacto-tryptone 10 g/l, yeast extract 5 g/l, sodium chloride 10 g/l, maltose 2 g/l, bacto-agar 15 g/l). Plaques were transferred to nitrocellulose filters (0.45 μm pore size, Sartorius AG, Gottingen, Germany), impregnated with 10 mM isopropyl B-D-thiogalactopyranoside (IPTG), at 37° C. for 2 hrs, after a 42° C. incubation for 3 hrs. These filters were blocked overnight at 4° C. with 3% bovine serum albumin (BSA—Sigma) in buffered saline (150 mM NaCl, 10 mM Tris). Patient serum, diluted one hundredfold in 3% BSA, was added to the filters and incubated at room temperature for 2 hrs, the filters then being washed for 30 mins in washing solution (150 mM NaCl, Tween 20, 0.05%), before the second antibody, a thousandfold dilution of anti-human IgG alkaline phosphatase conjugate (Sigma) in BSA 3% was added. After 1 hr at room temperature, the filters were again washed and stained with equal volumes of naphthol ASMX phosphate (Sigma, 0.4 mg/ml in distilled water) and Fast Red TR salt (Sigma, 6 mg/ml in 0.2M Tris pH 8.2) (the Fast Red stain). Positive plaques were transformed to 1.5 ml tubes containing 200 μl of SM (100 mM sodium chloride, 50 mM Tris-Cl pH 7.5, 10 mM magnesium sulphate, gelatine, 0.0001%), and 2 to 3 drops of chloroform. Plaque purification was performed by the above method.

(iii) Antigen-directed antibody selection

Two 100 μl aliquots of resuspended *E.coli* XL1-Blue cells were infected with a dilution of a high titre stock of purified positive phage, to give 5,000 pfu/85 mm L broth agarplate. Phage adsorption occured at 37° C. for 30 mins. The adsorption mixes were added to 2.5 ml aliquots of L broth agarose 0.8%, mixed, and poured onto L broth agar plates. These plates were incubated at 42° C. for 2.5 hrs, before nitrocellulose filters (0.45 μm pore size, Sartorius), pre-soaked in 10 mM IPTG and dried at room temperature for at least 1 hr, were added and incubated at 37° C. overnight. Each filter was then washed 3 times over 30 mins in Tris-buffered saline (150 mM sodium chloride, 10 mM Tris-Cl pH 7.2), and blocked overnight at 4° C. in 3% BSA. A tenfold dilution of patient serum in BSA 3% was added to the filters and incubated, with shaking, at room temperature for 3 hrs. This serum was removed, called the depleted serum and stored at 4° C. The filters were washed 5 times over 100 mins with Tween 20-Tris-buffered saline (150 mM sodium chloride, 10 mM Tris-Cl pH 7.2, Tween 20, 0.05%), and once with salt-Tween 20 solution (150 mM sodium chloride, Tween 20, 0.05o). The bound antibody was eluted by adding 5 ml of glycine saline buffer (150 mM sodium chloride, 200 mM glycine-Cl pH 2.8), and shaking at room temperature for 30 mins. The buffer was aspirated into a bijoux, containing Tris 0.04 g per 100 μl, mixed, termed the eluted antibody and stored at 4° C. A Western blot of *S.sobrinus* MUCOB 263 was performed essentially by the immunoblot method above with the original serum, depleted serum and eluted antibody being used as the primary antibodies. The antigen was the supernatant of the strain following crushing in an X-press. The secondary antibody was a thousandfold dilution of anti-human IgM and IgG alkaline phosphatase conjugates in 3% BSA, and the stain was the alkaline phosphatase stain.

Results

Six antibody positive clones were isolated and purified from the 60,000 pfu initially screened with culture-positive endocarditis patient serum. Antigen-directed antibody selection showed that the cloned, expressed sequence contained epitopes shared by *S.sobrinus* as the eluted antibody bound to the approximately 185 KDa antigen.

(iv) In vivo excision of DNA insert

A 10 ml overnight culture of *E.coli* XL1-Blue cells grown at 37° C. in L broth, containing tetracycline 125 µg/µl, was spun down at 2,000 rpm for 10 mins, resuspended in 4 ml of 10 mM magnesium sulphate, and stored at 4° C. In a 50 ml plastic conical tube, 200 µl of the resuspended *E.coli* XL1-Blue cells, 180 µl of high titre antibody-positive phage (1.78×108/85 mm plate approx) and 1 µl of R408 helper phage were combined and incubated at 37° C. for 15 mins. (Helper phage and *E.coli* XL1-Blue cells from CLONTECH). Then, 5 ml of 2×YT media (sodium chloride 5 g/l, yeast extract 10 g/l, bacto-tryptone 16 g/l pH 7.0) was added to the dual-infected bacteria and incubated, with shaking, at 37° C. for 3 hrs. The cells were killed by heating at 70° C. for 20 mins and ruptured by vortexing for 5 mins. The cells were spun at 4,000 rpm for 5 mins, and the supernatant containing pBluescript SK(-) phagemid decanted and stored at 4° C. The phagemid was propagated by adding 10 µl of the phagemid solution to 200 µl of resuspended *E.coli* XL1-Blue cells, incubating the culture at 37° C. for 15 mins, and plating 1 µl, 25 µl, 75 µl and 100 µl aliquots onto L broth agar plates, containing ampicillin 50 µg/ml.

(v) Plasmid DNA preparation and denaturation

The pBluescript SK(-) plasmid DNA was purified from the bacterial colonies with the Magic (RTM) Minipreps DNA purification System (Promega) and alkaline denatured by the method of Maniatis et al., 1989. Hence, 8 µl of solution, containing DNA 1.5–200 µg was added to 2 µl of 2M sodium hydroxide, briefly vortexed and spun, and left at room temperature for 10 mins. Then 3 µl of 3M sodium acetate (pH 4.8), 7 µl of distilled water, and 60 µl of -20° C. absolute ethanol were added and the DNA precipitated at -70° C. for 30 mins. The precipitate was pelleted at 13,000 rpm for 1 min, washed with -20° C. ethanol 70%, and vacuum-dried. The dried pellets were stored at -20° C.

(vi) DNA sequencing

DNA sequencing was performed by the two-step chain-termination method, with Sequenase (R) Version 2.0 (Cambridge Bioscience). The annealing step was carried out at 66° C. for 2 mins, the labelling at 22° C. for 4 mins, and the termination at 38° C. for 5 mins. Areas containing secondary structure were resolved by the substitution of dITP for dGTG. Sequencing reactions were run on acrylamide gels 6% for 11, 8, 5 and 2 hrs at 46°–51° C.

(vii) Subcloning with the TA cloning (RTM) system

The phagemid clone did not carry the 5' end of the cloned gene, therefore it was decided to subdlone the 5' end by Polymerase Chain Reaction (PCR), followed by TA cloning (RTM). The following PCR reagents were added to each of the 2 tubes containing 0.0 µg, 0.7 µg of *S.sobrinus* MUCOB 263 genomic DNA, with distilled water to give 64.3 µl total volume; 5.3 µl or 0.1 µg/µl Primer 1 (CAGTCTCCGTCCCAACGACTGCG) (SEQ ID NO:11), 4.4 µl of 0.1 µg/µl Primer 2 (GCTCCTCTTGTGACATGGTC) (SEQ ID NO:12), 10 µl of 10×Taq buffer (Northumbria Biochemicals Ltd., Northumberland (nbl), and 16 µl of dNTP's (12.5 µl of each of dATP, dGTP, dCTP, dTTP (Promega), added to 950 µl of deionized water). Then, 60 µl of mineral oil was carefully layered on top of the PCR reactions, the DNA denatured at 95° C. for 10 mins, and 2.5 Weiss Units of Taq (nbl) added. The PCR conditions were 94° C. for 1.5 mins, 50° C. for 1.5 mins, and 72° C. for 3 mins for 30 cycles, before a final long extension of 72° C. for 10 mins. The PCR products (30 µl) were run on a TBE gel 0.8%, at 50 volts for 2 hours, alongisde 4 µl of EcoR1-Hind III cut lambda DNA markers (nbl).

Insert DNA was subcloned with the TA Cloning (RTM) System Version 1.3 (In Vitrogen Corporation, British Biotechnologies Ltd, Oxon) as specified in the manufacturers protocol. Overnight, 12° C., ligation reactions containing 3.0 µl of a fourfold dilution, in distilled water, of the 0.7 µg PCR reaction, 4.7 µl of doubling dilution of the 0.7 µg PCR reaction, and a negative control were performed. In the transformation, white recombinant colonies were picked after overnight 37° C. incubation, and twice replated on kanamycin (50 µg/ml)/5-bromo-4-chloro-3-indolyl-β-D-galactopyranoside (X-Gal-25 µl of 40 mg/ml solution/plate) to achieve pure and stable subclones. Plasmid DNA was obtained, purified, denatured and sequenced. The origin of the cloned DNA from *S.sobrinus* was confirmed by Southern Blotting. The full sequence obtained in shown in Table 4.

5.2 *S.oralis* cloning

Figure 7:
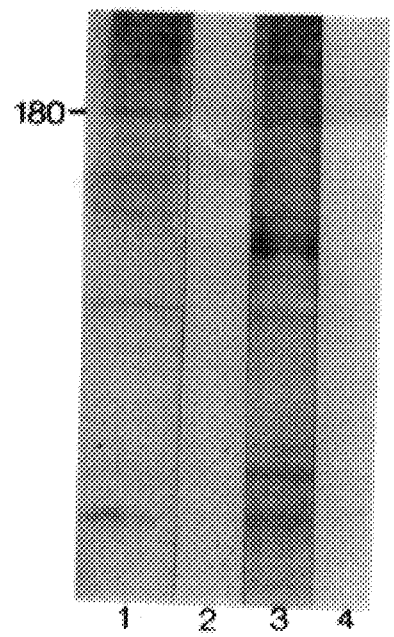
FIG. 7 shows that the clone from Streptococcus oralis had epitopes which cross reacted with the 180 KDa antigen of S. oralis. Tracks 1 and 3 are the original serum from two patients with antibody against S. oralis; Tracks 2 and 4 show the eluted subcomponent binding to the band at 180 KDa.

This was done essentially by the methods described above. The differences were that the vector was lambda gt11 and the DNA source was a clinical isolate of *Streptococcus oralis*. The library was a genomic DNA library partially digested with EcoR1. Ten positive clones were identified and one of these subcloned by the TA Cloning (RTM) System. The origin of the clone from *S.oralis* was confirmed by Southern Blotting. Antigen directed antibody selection showed that it had epitopes which cross-reacted with the 180 KDa antigen of *S.oralis* (FIG. 7). Tracks 1 and 3 show the original serum from two patients with antibody against *S.oralis*, and tracks 2 and 4 show the eluted subcomponent binding to the band at 180 kDa. The sequence of the clone is given in Table 5.

Comparison of the Sequences

The sequence obtained from *S.sobrinus* had a 99.2% homology to the SpaA antigen of *S.sobrinus* and a 68.4% homology to the PAc antigen of *S.mutans*. The *S.oralis* peptide carried a 76.2% homology over 605 amino acids with the *S.mutans* PAc protein precursor and 73.8% homology over 606 amino acids with both the *S.sobrinus* SpaA protein precursor and the *S.mutans* surface antigen I/II precursor. Both sequences contain a three tandem repeat motif of 39 amino acids. Six peptides were derived from these and used to epitope map this communal sera.

Epitope Mapping

Epitope mapping of the antigen cloned from *S. oralis* was carried out according to the protocol outlined by Geysen et al., J. Immunol. Methods, 102: 259–274 (1987) and references therein. In this epitope mapping, a complete set of overlapping nonapeptides was synthesised for the cloned *S. oralis* antigen. Peptide 1 covered residues 1–9, peptide 2 covered residues 2–10 and peptide 3 covered residues 3–11 etc. The epitopes were tested against various patient sera. All of the sera were examined at a 1 in 200 dilution for IgG and recording was stopped after 30 minutes. The sera examined were:

(1) Viridans endocarditis (n=8) (*S. sanguis* n=2, *S. oralis* n=2, *S. gordonii* n=4)

(2) *S. oralis* septicaemia n=5

(3) *S. mutans* endocarditis (n=2)

(4) *E. faecalis* endocarditis (n=2)

(5) Negative control (n=5)

Epitopes were defined as those peptides which:

(1) were positive in at least 3 wells (2) had an optical density of each well which was at least double the negative control value and in the majority of wells greater than 0.8

This epitope mapping identified a total of 9 epitopes (see table 10) NFKQGQG (SEQ ID NO:13), RQPG (SEQ ID NO:14), SWYGAG (SEQ ID NO:15), GKIRAV (SEQ ID NO:16), RLFAQPQ (SEQ ID NO:17), AGRPK (SEQ ID NO:18), PTGYQFD (SEQ ID NO:19), YPTVV (SEQ ID NO:20) and LLKKA (SEQ ID NO:21).

After the initial epitope mapping, each individual serum was then reexamined for positivity with each well (see table 11).

6. Preparation of Immunodominant Epitopes from Cloned *S.oralis*

Of the synthetic peptides (see 5.2; "Comparison of the Sequences"), peptides 1–4 cover the sequence of *S.oralis* as short peptides of 15 amino acid length. Peptides 5 and 6 covered the *S.sobrinus* area which differed. These sequences are listed (Table 6) and illustrated (FIG. 8).

The six synthetic peptides were produced by Cambridge Biochemicals Ltd., Nantwich and dissolved in a double-distilled water to give a final concentration of 2 mg/ml. Aliquots, 0.5 ml, were stored at −70° C. and after one freeze-thaw cycle, stored at −20° C.

The wells of six plastic microtiter plates (Falcon (R) 3912, Microtest (RTM Flexible Assay Plate, 96 flat-bottom wells—Becton Dickinson & Co, Fred Baker, Liverpool), one for each peptide, were coated with 200 μl of the appropriate 10 μg/ml synthetic peptide solution diluted in phosphate buffered saline (one tablet dissolved in 100 ml distilled water, Oxoid, Unipath Ltd, Basingstoke; PBS). The peptides were added and left at 4° C. overnight to coat the wells. Excess peptide was then removed by washing the microtitre plates five times in PBS with a Nunc-Immuno Wash (RTM) (InterMed, Denmark). The primary antibody, 200 μl of a 1/10 dilution in 3% BSA of sera was added and left at room temperature for 1 hour to allow antigen-antibody binding. After washing five times in PBS, the wells were filled with 200 μl of one of i) a 1/1000 dilution of goat anti-human IgM peroxidase conjugate in 3% BSA (Sigma), ii) a 1/1000 dilution of goat anti-human IgG peroxidase conjugate in 3% BSA (Sigma), or iii) with PBS.

The conjugates were left to react at room temperature for 1 hour. The plates were then washed as before and 200 μl of ABTS stain was added to each well (three tablets of 2.2' amino-bis(3-ethylbenzthiazoline-6-sulfonic acid); diammonium salt; Sigma) and 160 μl of 30% w/w hydrogen peroxide solution; Sigma, in 60 ml of 125 mM disodium hydrogen orthophosphate buffer brought to pH 4.0 with 1M citric acid). This ABTS stain was prepared just prior to use. The signal strength for each well was then read at 405 nm at 5, 10 and 15 mins after the start of the reaction with a microtitre plate reader (Titertek Muliskan (10) PLUS MKH, Labsystems, Finland) attached to an impact dot matrix printer (Panasonic KX-P1081, Panasonic Matsushita Electric Industrial Co Ltd, Osaka, Japan).

To determine which of the six peptides representing the *S.sobrinus/S.oralis* antigenic region which produced the most specific and strongest positive signal, each of the peptides was used in an indirect ELISA.

All peptides were screened against a panel of 5 sera (single sera from cases of *S.mutans* endocarditis, *S.oralis* endocarditis, *S.oralis* septicaemia, *S.lactis* endocarditis and *S.aureus* endorcarditis).

All 6 peptides were recognised by the sera from the cases of endocarditis due to *S.mutans* and *S.oralis*. They had much lower Optical Densities with the sera from the septicaemia due to *S.oralis* and the control sera from cases of endocarditis due to *S.lactis* and *S.aureus*. Peptide 1 showed the highest OD (IgG) in *S.mutans* endocarditis and was selected for firther studies (Table 7).

Indirect ELISA

As a result of the epitope mapping and of the preparation of immunodominant epitopes from clones *S. oralis* (see above), three peptides were investigated further in indirect ELISA tests. These peptides were YEVEKPLEPAPVAP (SEQ ID NO:3) (Peptide 1), TMYPNRQPGSGWDSS (SEQ ID NO:9)(contains the epitope RQPG (SEQ ID NO:14)-epitope numbers 74–79; Peptide 7) and WYSLNGKIRAVD-VPK (SEQ ID NO:10)(contains the epitope GKIRAV (SEQ ID NO:16)-epitope numbers 144–147; Peptide 8).

Sera Tested

Sera from cases of endocarditis due to *S.mutans* (2), *S.oralis* (3), *S.gordinii* (10), *S.sanguis* (2), *E.faecalis* (11), *S.bovis* (8), *S.agalactiae* (1), *S.lactis* (1), *S.pneunoniae* (4), Group G Streptococcus (2), *S.aureus* (2), Coagulase Negative Staphylococci (6), *Candida albicans* (1), *Candida parapsilosis* (2) and *E.coli* (1), septicaemias due to *S.oralis* (8), *E.faecalis* (7), *E.faecium* (2) and a brain abscess due to *S.milleri*. Further controls were sera from patients with SLE (3) and neutropenic leukaemic patients with no evidence of streptococcal infection (20).

The optical densities are given in Table 8 for Peptide 1, and in Table 8a for Peptides 1, 2 and 3.

Results

In summary, a raised IgG was specific to patients with Steptococcal endocarditis and a raised IgM specific to endocarditis due to *Streptococcus oralis/gordonii/sanguis/mitis*.

If a cut off point of 0.6 is taken for the Optical Densitivity for IgG and 0.4 for IgM then all cases of *S.mutans* (patient 1), *S.oralis* (patient 4), *S.gordonii* (patients 6–14) and *S.sanguis* (patients 16 and 17) endocarditis fulfilled one or other of these criteria. All other sera were classified as negative. All controls were negative except for a raised IgG in cases of endocarditis due to *E.faecalis, S.bovis* and Group G streptococci (Table 9).

This data proves the value of the test in culture positive endocarditis. It could also be extended to cover culture negative cases.

One treatment of IgM fell in cases 6, 13 and 15 showing that a falling IgM was a marker of successful therapy.

An analysis of the overall results (see tables 12 and 13 below) showed that the tests performed using peptide 1 gave the most accurate and specific results (100% specificity), but were the least sensitive (50% sensitivity). Tests wth the other two peptides were more sensitive, but less specific and gave more false positives. This suggests that although each of the peptides could be usefully used individually, a combination of tests using more than one peptide would allow for an overall test which was both highly sensitive and highly specific.

TABLE 12

|  | Peptide 1 | | Peptide 7 | | Peptide 8 | |
| --- | --- | --- | --- | --- | --- | --- |
|  | IgM | IgG | IgM | IgG | IgM | IgG |
| True Positives | 6 | 5 | 12 | 5 | 12 | 10 |
| False Positives | 0 | 1 | 28 | 15 | 25 | 21 |
| True Negatives | 42 | 41 | 14 | 27 | 17 | 21 |
| False Negatives | 6 | 7 | 0 | 7 | 0 | 2 |

(For raw data see table 8a)

TABLE 13

|  | IgM Peptides | | | IgG Peptides | | |
| --- | --- | --- | --- | --- | --- | --- |
|  | 1 | 7 | 8 | 1 | 7 | 8 |
| Sensitivity | 50% | 100% | 100% | 41.5% | 41.5% | 83% |
| Specificity | 100% | 33% | 40% | 98% | 64% | 50% |
| Efficiency | 89% | 48% | 53% | 85% | 59% | 57% |

7. Fibronectin Binding Studies

In order to test for fibronectin binding activity in the cloned proteins, each of the peptides 1–6 was reacted in an indirect ELISA according to the previous protocol.

Figure 9:
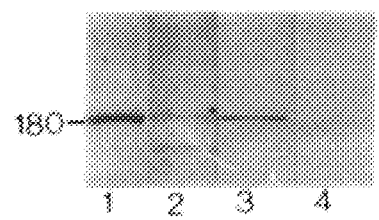
FIG. 9 shows antibody cross reacting with the 185 KDa antigen of Streptococcus sobrinus (Track 1) and the 180 KDa antigen of Streptococcus oralis (Track 3) and the elimination of the cross reactivity by prior absorption with fibronectin. (Tracks 2 and 4).

The indirect ELISA produced OD values greater than 2 forall six peptides regardless of whether fibronectin was added to the sandwich. This implied that the polyclonal serum (anti-fibronectin 0.5 mg/ml Sigma [F 1509]) reacted with the peptides directly. This serum was then immunoblotted at a dilution of 1 in 40 and again after crossabsorbing, 100 μl of 1 mg/ml antibody, with 100 μl of 1 mg/ml of fibronectin (F2006 Sigma) at 37° C. for 30 mins. This showed that the antiserun reacted specifically with the 180 kDa antigen of S.oralis, 180 kDa antigen of S.gordonii and 120 kDa antigen of S.sanguis. This is illustrated by FIG. 2 tracks 1 and 2 (S.gordonii), FIG. 4 tracks 1 and 2 (S.oralis) and FIG. 5 tracks 1 and 2 (S.sanguis). FIG. 9 shows the antibody crossreacting with the 185 kDa antigen of S.sobrinus (Track 1) and the 180 KDa antigen of S.oralis (clinical isolate) (Track 3) and the elimination of the crossreactivity by prior absoroption with fibronectin (Tracks 2 and 4).

This is with the previously identified immunodominant antigens of these microorganisms and implies that they act as a mimic for fibronectin. This appears to be the mechanism by which these streptococci bind to heart valves. A comparison of the sequences of the peptides with human fibronectin showed subtantial homology (GCG pogramme Gap; Sequence of fibronectin by Kornblitt et al. EMBO J. 4: 1755–1759, 1985). The most homologous region of the fibronectin molecule was a 69 residue sequence beginning at residue 750 of the fibronectin protein. The percentage similarity and identity values were 48.7% and 35.9% respectively (FIG. 10).

8. Human Recombinant Antibodies

Figure 11:
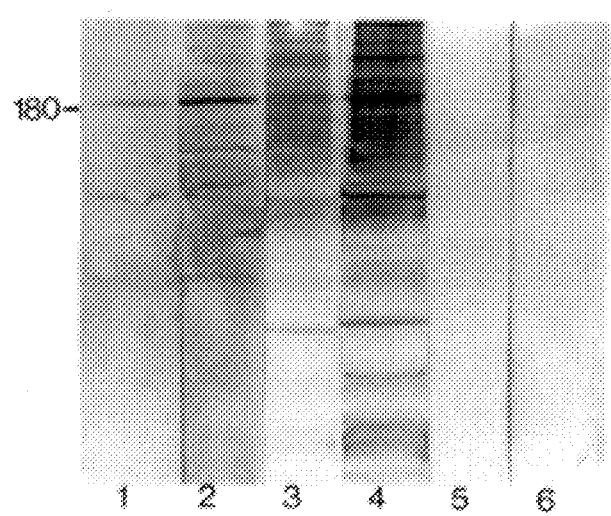
FIG. 11 shows the results of screening a library of immunoglobulin heavy and light chain variable genes from a patient with infection due to viridans streptococcus against Streptococcus oralis NCTC 7864 (Tracks 5 and 6). Pre and post IgM (Tracks 1 and 2) and IgG (Tracks 3 and 4) from a patient recovering from septicaemia due to S. oralis are shown for comparison.

A library of immunoglobulin heavy and light chain variable (V) genes was prepared from the peripheral blood lymphocytes of a patient with infection due to a viridans streptococcus (blood culture positive) septicaemia following an oesophagectomy who recovered on amoxicillin and gentamicin. Screening of this library by immunoblot against S.oralis NCTC 7864 showed recombinant antibody against the band at 180 KDa (FIG. 11, tracks 5 and 6). The pre and post IgM (Tracks 1 and 2) and IgG (Tracks 3 and 4) from a patient recovering from septicaemnia due to S.oralis is shown for comparison.

The library was produced essentially as described by Marks et al (J. Mol. Biol., 1991, 222: 581–597) using the pCANTAB 5 vector, which is now commercially available as part of a kit from Pharmacia (Milton Keynes, UK). The heavy and light chain V genes, obtained from cDNA prepared from the mRNA of peripheral blood lymphocytes of a patient recovering from a viridans streptococcus (blood culture positive) septicaemia, were randomly combined and subcloned into Not I/Sfi I digested pCANTAB 5. The resulting single chain Fv fragments (ScFv), expressed on the surface of phage, were enriched by panning four times against the specific synthetic peptide epitopes YEVEKPLEPAPVAPS (SEQ ID NO:3), TMYPNRQPGSGWDSS (SEQ ID NO:9) and WYSLNGKIRAVDVPK (SEQ ID NO:10) (Peptides 1, 7 and 8). Following the fourth panning, twenty clones (from each of the last pannings) were:

1. Bst1 fingerprinted to establish the degree of focussing of the panning procedure; and
2. Examined in an indirect ELISA against the original peptide (as described in detail previously). Conditions were:

Recombinant antibody: neat

Phage specific monoclonal: 1 in 2,000

Antimouse Horse Radish Peroxidase 1 in 1,000

100 ml of Peptide applied to well in PBS at 10 ug/ml and incubated overnight at 4° C.

Results

Peptide 1

20 clones selected were identical on Bst1 fingerprinting. Indirect ELISA varied from 0.25–0.30 (control 0.17). Two clones (PAC 1 and PAC 2) selected for animal work.

Peptide 7

16 clones produced 6 types. One type (Type A) was present in 7 out of the 16 clones and was the only type to produce a positive reading in the indirect ELISA (0.276–0.318) (control 0.17). One clone (Clone 3) selected for animal work (PAC 3).

Peptide 8

16 clones produced 10 types. Two of these, A and B were represented by 3 and 5 clones respectively. None of these clones produced a positive ELISA result. Five of the 8 clones produced a positive ELISA result (range 0.235–0.304 control 0.138) and a unique Bst1 fingerprint. One of these (Clone 7) was selected for animal work (PAC 4).

In order to test the efficacy of the selected clones specific to Peptides 1–3 in treating S. oralis and vancomycin-resistant E. faeciun infections, a set of experiments with PAC 1–4 and other controls was performed.

Experiment 1

This experiment was an acute streptococcal infection model using Balb/c mice with an end point of death. Conditions were:

S. oralis dose: $5.7 \times 10^9$

Phage dose: $5 \times 10^8$ pfu/ml

Antibody given first, followed by S.oralis 2 hours later.

TABLE 14

(results of Experiment 1)

| | SURVIVORS | | |
| --- | --- | --- | --- |
| Antibody | No. of mice | 4 hours | 24 hours | 48 hours |
| Control: no antibody M13K07 phage | 15 | 7 | 3 | 1 |
| DEPAGE | 13 | 3 | 3 | 2 |

TABLE 14-continued (results of Experiment 1)

SURVIVORS

| Antibody | No. of mice | 4 hours | 24 hours | 48 hours |
|---|---|---|---|---|
| B3.7 | 13 | 6 | 6 | 6 |
| B3.14 | 8 | 1 | 1 | 1 |
| PAC 1 | 9 | 9 | 2 | 2 |
| PAC 2 | 17 | 8 | 8 | 8 |
| PAC 3 | 15 | 6 | 6 | 6 |
| PAC 4 | 15 | 2 | 2 | 2 |

DEPAGE - antibody against a Candidal specific carboxy-end HSP90 antigen (sequence DEPAGE) which acts as an irrelevant phage and therefore a control.
Fisher exact 2 tailed P value showed statistical significance for B3.7 at 48 hours (P 0.03), PAC 1 at 2 hours (P 0.0095) and PAC 2 at 48 hours (P 0.02). B3.7 is a recombinant antibody specific to the HSP90 stress protein, suggesting that antibodies specific to the HSP90 protein may be used to diagnose and treat S. oralis and possibly other streptococcal and enterococcal infections.

Experiment 2

This was a chronic streptococcal infection model using CD1 mice and a colony count of spleen and kidney was performed at the various end-points. Conditions were:

S.oralis dose $2.5 \times 10^9$
Phage dose $5 \times 10^{10}$ pfu/ml
S.oralis given first, antibody given 24 hours later.
Positive organ count $>10^4$/g/ml
S=Spleen, K=Kidney
S+K=combined spleen and kidney results
5 mice sacrificed on days 4, 7 and 12
Repeat antibody injection at day 10.

TABLE 15

(results of Experiment 2)

|  | Day 4 | | | Day 7 | | | Day 12 | | |
|---|---|---|---|---|---|---|---|---|---|
|  | S | K | S+K | S | K | S+K | S | K | S+K |
| Control:no antibody M13K07 phage | 4 | 4 | 8 | 0 | 0 | 0 | 1 | 0 | 1 |
| B3.14 | 1 | 2 | 3 | 0 | 0 | 0 | 0 | 0 | 0 |
| PAC 2 | 0 | 1 | 1 | 1 | 1 | 2 | 1 | 0 | 1 |
| PAC 3 | 1 | 2 | 3 | 0 | 0 | 0 | 0 | 0 | 0 |

No phage recovered after 24 hours post injection, all mice blood cultures negative.

Fisher exact 2 tailed P value showed statistical significance for PAC 2 (P=0.005) when spleen and kidney results were combined from day 4.

Experiment 3

This was an infection model with CD1 mice using high level vancomycin-resistant E. faecium. Conditions were:

E. faecium dose: $3 \times 10^{10}$/ml
Phage dose: $5 \times 10^{10}$ pfu/ml
E. faecium given first, antibody given 24 hours later.
Positive>$10^4$ g/ml. S=spleen, K=Kidney
S+K=Spleen+Kidney.
Spontaneous deaths cultured at day 2
5 mice sacrificed on day 4
Remaining mice 3 for the M13K07 control and 5 for the PAC 2 antibody, sacrificed at day 7.

TABLE 16

(results of Experiment 3)

|  | Day 2 (spontaneous deaths) | Day 4 (n = 5) | | | Day 7 (n = 3 control) (n = 5 PAC 2) | | |
|---|---|---|---|---|---|---|---|
|  |  | S | K | S+K | S | K | S+K |
| Control no antibody: M13K07 phage | 6[a] | 2 | 5 | 7 | 0 | 0 | 0 |
| PAC 2 | 4[a] | 2 | 3 | 5 | 0 | 0 | 0 |

[a]all spleens and kidneys cultured and positive > $10^4$/gl/ml
Total positive Control: 19/22
PAC: 13/18

This produced by combing the spleen and kidney results obtained from the spontaneous deaths (day 2) with 5 mice (day 4) sacrificed assuming>$10^4$ organisms/g/ml is positive. This suggests PAC2 may have some activity agianst vancomycin-resisitant E.faecium.

Experiment 4

This was an acute streptococcal infection model using Balb/c mice infected with vancomycin-resistant E. faecium. The end-point was death. Coonditions were:

Organism: high level (>256 mg/l) vancomycin-resistant E. faecium
E.faecium dose: $5 \times 10^{10}$/ml
Phage dose: $5 \times 10^{10}$ pfu/ml
Antibody given first, followed by E.faecium 2 hours later.

TABLE 17

(results of experiment 4)

| | | Survivors | | |
|---|---|---|---|---|
| Antibody | No of mice | 4 hours | 24 hours | 48 hours |
| Control no antibody M13K07 phage | 15 | 10 | 5 | 1 |
| PAC 2 | 15 | 12 | 8 | 6 |

Fisher exact 2 tailed P value showed statistical significance for Pac 2 at 48 hours (p 0.02)

TABLE 1

Immunoblot testing of the S.oralis NCTC 7864 antigen against patient sera.

| | Patient Sera | | | | | | | | | | | | | |
|---|---|---|---|---|---|---|---|---|---|---|---|---|---|---|
| | Endocarditis | | | | | | Sequential sera | | | | Controls | | | |
| | S.oralis Endo-carditis n = 2 | | S.gordonii Endo-carditis n = 4 | | S.sanguis Endo-carditis n = 2 | | S.oralis. septicaemia n = 12 | | | | Controls Neutropenic n = 20 | | Controls Non-Neutropenic n = 20 | |
| M.Wt. of S.oralis antigen | | | | | | | Constant Septicaemia | | Inc. × 2 or App. | | | | | |
| band | IgM | IgG | IgM | IgG | IgM | IgG | IgM | IgG | IgM | IgG | IgM | IgG | IgM | IgG |
| 192 | 1 | 1 | 2 | 10 | 1 | 2 | 1 | 3 | 1 | 5 | 4 | 6 | 2 | 1 |
| 185 | | 1 | | 4 | 1 | 1 | | 1 | 1 | 3 | 2 | 3 | 1 | 2 |
| 180 | 2 | 2 | 4 | 13 | 1 | 2 | | 2 | 9 | 10 | 1 | 3 | | 4 |
| 155 | | 1 | | 9 | | 1 | | 4 | | | | 2 | | |
| 140 | 1 | 2 | 2 | 6 | | | 3 | 8 | 1 | 2 | 2 | 8 | 1 | 2 |
| 105 | | 1 | 1 | 5 | | 1 | | 1 | | | 2 | 2 | 1 | 1 |
| 85 | 2 | 2 | 4 | 11 | 1 | 2 | | 8 | 1 | 1 | 3 | 3 | 1 | 1 |
| 76 | | 1 | 1 | 3 | | 1 | 1 | 5 | 2 | 1 | 2 | 2 | | |
| 65 | 1 | | | 3 | | | | | | 1 | | | | |
| 51 | | 1 | 6 | 3 | | 1 | | 11 | 2 | | 1 | 11 | | 6 |
| 46 | | 2 | | 3 | | | | 1 | 1 | | | 1 | | |
| 35 | | 1 | | 1 | | 1 | | | | | | | | |

Inc = Increased × 2
App = Appeared

TABLE 2

Immunoblot testing of the S.gordonii NCTC 7868 antigen against patient sera.

| | Patient Sera | | | | | | | | | | | | | |
|---|---|---|---|---|---|---|---|---|---|---|---|---|---|---|
| | Endocarditis | | | | | | Sequential sera | | | | Controls | | | |
| | S.oralis Endo-carditis n = 2 | | S.gordonii Endo-carditis n = 4 | | S.sanguis Endo-carditis n = 2 | | S.oralis. septicaemia n = 12 | | | | Controls Neutropenic n = 20 | | Controls Non-Neutropenic n = 20 | |
| M.Wt. of S.oralis antigen | | | | | | | Constant Septicaemia | | Inc. × 2 or App. | | | | | |
| band | IgM | IgG | IgM | IgG | IgM | IgG | IgM | IgG | IgM | IgG | IgM | IgG | IgM | IgG |
| 185 | | 2 | 2 | 5 | | | 1 | 7 | | | | | | |
| 180 | | 2 | 12 | 14 | 2 | 2 | | 6 | | | | 5 | 1 | 2 |
| 105 | | 1 | | 1 | | | 2 | 4 | | | 1 | 3 | | 1 |
| 85 | 2 | 1 | 12 | 14 | 1 | 1 | 1 | 10 | | | | | 1 | 1 |
| 80 | | | 5 | 12 | 1 | 1 | 1 | 9 | | | 1 | 11 | | 4 |
| 76 | | | 5 | 7 | 1 | 1 | | | | | 1 | 10 | 1 | 3 |
| 72 | 1 | 1 | 5 | 7 | | 1 | | | | 1 | 1 | 4 | 1 | 1 |
| 70 | | 1 | 4 | 5 | 1 | 2 | | 7 | | | | | | |
| 65 | | | 9 | 13 | 1 | 2 | 1 | 4 | | | | 1 | | 1 |
| 58 | | | 1 | 9 | | | | | | | | | | |
| 56 | | | 2 | 9 | | 1 | | | | | | | | |
| 52 | | | 1 | 8 | | 2 | | | | | | | | |
| 47 | | 2 | 12 | 14 | 1 | 1 | | 10 | | 2 | 1 | 15 | 2 | 2 |
| 40 | | | 5 | 8 | 2 | 1 | | 8 | | 1 | | 1 | | |
| 37 | | | 8 | 8 | 2 | 2 | | | | | | | | |
| 35 | | | 3 | 110 | 1 | 1 | | 2 | | 1 | | | | |
| 33 | | | 2 | 9 | | | | | | | | | | |
| 30 | | | 1 | 11 | 2 | 2 | | | | | | | | |
| 28 | | | 2 | 7 | | 1 | | | | | | | | |

Inc = Increased
App = Appeared

TABLE 3

Immunoblot testing of the S. sanguis NCTC 7863 antigen against patient sera.

| M. Wt. of S. sanguis antigen band | Endocarditis | | | | | | Septicaemia | | | | | |
|---|---|---|---|---|---|---|---|---|---|---|---|---|
| | S. oralis Endocarditis n = 2 | | S. gordonii Endocarditis n = 14 | | S. sanguis Endocarditis n = 2 | | S. oralis Septicaemia n = 9 | | Controls Neutropenic n = 20 | | Controls Non-Neutropenic n = 20 | |
| | IgM | IgG | IgM | IgG | IgM | IgG | IgM | IgG | IgM | IgG | IgM | IgG |
| 120 | | 2 | 4 | 14 | 2 | 2 | | 1 | 3 | 3 | | 4 |
| 85 | | 1 | | 2 | 2 | 2 | | 8 | 3 | 3 | 2 | 4 |
| 83 | | | 2 | 2 | | | | | | | | |
| 81 | | | 2 | 8 | 2 | 2 | | | | | | |
| 75 | 1 | 1 | 4 | 2 | | 2 | 2 | 5 | 3 | 15 | | 8 |
| 59 | 1 | 1 | | 2 | 1 | | | | | | 2 | 2 |
| 57 | 1 | 2 | 2 | 12 | 1 | | | | | | 2 | 2 |
| 55 | 1 | 1 | | | | 2 | | | | 6 | 2 | 12 |
| 50 | | | | | | | | 9 | | | | 2 |
| 47 | | | 2 | | 2 | 2 | | | | 9 | 2 | 6 |
| 42 | 1 | | 6 | | 2 | 2 | | | | 9 | | |
| 40 | | | | | 2 | 2 | | 9 | | | | 2 |
| 37 | | | | | | | | 3 | | | 2 | 2 |
| 35 | | | | | 1 | | | | | | | |
| 32 | | | | | | | | | | | | |
| 25 | | | 6 | | | | | | | | | 2 |

TABLE 4

Full sequence of cloned S.sobrinus gene (SEQ ID NO:22) and corresponding amino acid sequence (SEQ ID NO:23)

```
5'          10                    30                    50
GCTCCTCTTG  TGACATGGTC  ATAGTAACAG  ATAATCTGTT  TAATTTCAAG  CAGATTTAAT 70                    90                    110
AGCCTCCAGG  AAACTTGAAA  TAAAACTGAA  ATAAAACTGA  ATTTTTTATA  AAGCCTAGAT 130                   150                   170
TAAGCAATCG  TTTGCATTGA  CAATCACTAG  ATAAGTGTTA  TTATAGATAG  TATTGTAACG 190                   210                   230
AAACATTTCA  GATGTTACAA  AAATGTAAAT  TGGAGGGAAT  TATAATATGC  AACGAAAAGA
                                                        M    Q  R  K  E 250                   270                   290
GACTTTTGGG  TTTCGCAAAA  GTAAAATCAG  TAGGACCCTT  TGTGGTGCCT  TACTAGGAAC
 T  F  G     F  R  K     S  K  I  S   R  T  L    C  G  A    L  L  G  T 310                   330                   350
TGCTATCTTA  GCGTCTGTAA  CAGGTCAAAA  GGCGCTCGCT  GAAGAAACAA  GTACCACTTC
 A  I  L     A  S  V     T  G  Q  K   A  L  A    E  E  T    S  T  T  S 370                   390                   410
AACTTCGGGG  GTTAATACCG  CAGTCGTTGG  GACGGAGACT  GGGAATCCCG  CCACCAACCT
 T  S  G     V  N  T     A  V  V  G   T  E  T    G  N  P    A  T  N  L 430                   450                   470
GCCTGACAAA  CAGGACAATC  CAAGTTCGCA  AGCCGAGACA  AGTCAGGCCC  AAGCCGGTCA
 P  D  K     Q  D  N     P  S  S  Q   A  E  T    S  Q  A    Q  A  G  Q 490                   510                   530
AAAGACAGGG  GCAATGTCAG  TAGATGTGTC  TACAAGTGAG  CTTGACGAAG  CTGCTAAAAG
 K  T  G     A  M  S     V  D  V  S   T  S  E    L  D  E    A  A  K  S 550                   570                   590
TGCCCAAGAA  GCTGGTGTGA  CCGTTTCGCA  GGATGCTACC  GTCGATAAAG  GGACAGTAGA
 A  Q  E     A  G  V     T  V  S  Q   D  A  T    V  D  K    G  T  V  E 610                   630                   650
AACTTCTGAC  GAAGCTAACC  AAAAAGAAAC  CGAAATCAAG  GATGACTACA  GCAAGCAAGC
 T  S  D     E  A  N     Q  K  E  T   E  I  K    D  D  Y    S  K  Q  A
```

TABLE 4-continued

Full sequence of cloned *S.sobrinus* gene (SEQ ID NO:22) and corresponding amino acid sequence (SEQ ID NO:23)

```
            670                      690                      710
AGCAGACATC  CAAAAGACAA  CAGAAGACTA  CAAGGCAGCT  GTGGCTCGTA  ACCAAGCCGA
  A  D  I     Q  K  T    T  E  D  Y    K  A  A    V  A  R    N  Q  A  E 730                      750                      770
AACAGACCGA  ATCACTCAAG  AAAACGCGGC  TAAGAAGGCC  CAATACGAAC  AAGATTTGGC
  T  D  R    I  T  Q     E  N  A  A    K  K  A    Q  Y  E    Q  D  L  A 790                      810                      830
GGCCAACAAG  GCAGAAGTGG  AACGCATTAC  CAATGAGAAT  GCGCAACGCA  AGGCTGATTA
  A  N  K    A  E  V     E  R  I  T    N  E  N    A  Q  R    K  A  D  Y 850                      870                      890
CGAAGCTAAG  CTGGCTCAAT  ATCAAAAGGA  CCTAGCAGCC  GTTCAACAAG  CTAATAATGA
  E  A  K    L  A  Q     Y  Q  K  D    L  A  A    V  Q  Q   {A  N  N  D
                                                            A1

910                      930                      950
CAGTCAAGCA  GCCTACGCTG  CTGCCAAGGA  AGCCTACGAC  AAAGAATTGG  CTCGGGTTCA
  S  Q  A    A  Y  A     A  A  K  E    A  Y  D    K  E  L    A  R  V  Q 970                      990                      1010
AGCTGCTAAT  GCCGCTGCTA  AGAAAGAATA  CGAAGAGGCT  CTAGCTGCCA  ACACCACTAA
  A  A  N    A  A  A     K  K  E  Y    E  E  A    L  A  A    N  T  T  K 1030                     1050                     1070
GAATGAGCAA  ATCAAGGCAG  AAAACGCCGC  TATCCAGCAA  CGCAATGCCC  AAGCTAAGGC
  N  E  Q    I  K  A     E  N  A  A    I  Q  Q    R  N  A    Q  A  K  A 1090                     1110                     1130
AGATTACGAA  GCCAAGTTGG  CTCAATATGA  AAAAGATTTA  GCCGCAGCCC  AGTCTGGTAA
  D  Y  E    A  K  L     A  Q  Y  E    K  D  L    A  A  A    Q  S} {G  N
                                                                    A2

1150                     1170                     1190
TGCTACAAAT  GAAGCGGACT  ACCAAGCTAA  GAAGGCAGCT  TATGAACAAG  AGTTAGCGCG
  A  T  N    E  A  D     Y  Q  A  K    K  A  A    Y  E  Q    E  L  A  R 1210                     1230                     1250
CGTGCAAGCC  GCTAATGCAG  CTGCCAAGCA  GGCCTACGAA  CAAGCTCTAG  CTGCCAACAC
  V  Q  A    A  N  A     A  A  K  Q    A  Y  E    Q  A  L    A  A  N  T 1270                     1290                     1310
GGCCAAGAAC  GCCCAAATCA  CGGCCGAAAA  TGAGGCTATC  CAGCAGCGCA  ATGCGCAAGC
  A  K  N    A  Q  I     T  A  E  N    E  A  I    Q  Q  R    N  A  Q  A 1330                     1350                     1370
TAAGGCTAAC  TATGAAGCTA  AATTAGCCCA  ATATCAAAAG  GATTTGGCCG  CAGCTCAATC
  K  A  N    Y  E  A     K  L  A  Q    Y  Q  K    D  L  A    A  A  Q  S}

1390                     1410                     1430
TGGTAACGCC  GCTAATGAGG  CAGACTACCA  AGAAAAATTA  GCAGCCTATG  AAAAGGAACT
 {G  N  A    A  N  E     A  D  Y  Q    E  K  L    A  A  Y    E  K  E  L
  A3

1450                     1470                     1490
GGCTCGTGTG  CAAGCAGCCA  ATGCAGCTGC  TAAGCAAGAA  TATGAGCAGA  AAGTTCAGGA
  A  R  V    Q  A  A     N  A  A  A    K  Q  E    Y  E  Q    K  V  Q  E 1510                     1530                     1550
AGCTAATGCT  AAAAATGCCG  AAATTACGGA  AGCCAACCGT  GCTATCCGTG  AACGCAATGC
  A  N  A    K  N  A     E  I  T  E    A  N  R    A  I  R    E  R  N  A 1570                     1590                     1610
CAAGGCCAAG  ACAGACTATG  AACTCAAACT  GTCTAAGTAC  CAAGAAGAGC  TTGCTCAGTA
  K  A  K    T  D  Y     E  L  K  L    S  K  Y    Q  E  E    L  A  Q  Y 1630                     1650                     1670
CAAGAAGGAC  CTAGCGGAAT  ACCCAGCTAA  ACTCCAAGCC  TATCAAGATG  AACAAGCCGC
  K  K} D    L  A  E     Y  P  A  K    L  Q  A    Y  Q  D    E  Q  A  A 1690                     1710                     1730
AATCAAGGCA  GCTCTGGAAG  AGTTGGAAAA  GCACAAGAAT  GAAGATTGGA  ACCTCAGTGA
  I  K  A    A  L  E     E  L  E  K    H  K  N    E  D  W    N  L  S  E
```

TABLE 4-continued

Full sequence of cloned *S.sobrinus* gene (SEQ ID NO:22) and corresponding amino acid sequence (SEQ ID NO:23)

```
            1750                        1770                        1790
GCCCTCAGCC  CAGAGTCTGG  TCTATGACTT  GGAGCCCAAT  GCTCAGATTT  CCCTAGTGAC
  P  S  A     Q  S  L     V  Y  D  L    E  P  N    A  Q  I     S  L  V  T 1810                        1830                        1850
CGATTGGAAG  CTACTGAAAG  CCTCCTCCCT  TGATGAATCC  TTTAGCCACG  ATACTGAACA
  D  W  K     L  L  K     A  S  S  L    D  E  S    F  S  H     D  T  E  Q 1870                        1890                        1910
ATATAACAAA  CACAACCTGC  AGCCAGATAA  TCTAAATATA  ACCTATCTGG  AGCAGGCTGA
  Y  N  K     H  N  L     Q  P  D  N    L  N  I    T  Y  L     E  Q  A  D 1930                        1950                        1970
TGATGTGGCC  TCCTCAGTAG  AGCTCTTTGG  TAATTTCGGT  GATAAGGCTG  GTTGGACAAC
  D  V  A     S  S  V     E  L  F  G    N  F  G    D  K  A     G  W  T  T 1990                        2010                        2030
CACTGTCAGC  AATGGTTCAG  AAGTTAAGTT  TGCCTCTGTC  CTCCTCAAGC  GTGGCCAGAG
  T  V  S     N  G  S     E  V  K  F    A  S  V    L  L  K     R  G  Q  S 2050                        2070                        2090
TGCTACAGCC  ACCTATACCA  ACCTGAAAAA  CTCTTACTAC  AATGGTAAGA  AAATTTCTAA
  A  T  A     T  Y  T     N  L  K  N    S  Y  Y    N  G  K     K  I  S  K 2110                        2130                        2150
GGTGGTCTAC  AAGTATACGG  TTGACCCTGA  CTCCAAGTTT  CAAAATCCTA  CTGGTAACGT
  V  V  Y     K  Y  T     V  D  P  D    S  K  F    Q  N  P     T  G  N  V 2170                        2190                        2210
TTGGTTAGGT  ATCTTTACTG  ACCCAACCCT  AGGGGTCTTT  GCCTCAGCCT  ATACGGGTCA
  W  L  G     I  F  T     D  P  T  L    G  V  F    A  S  A     Y  T  G  Q 2230                        2250                        2270
AAACGAGAAG  GATACCTCTA  TCTTTATCAA  GAATGAATTC  ACCTTCTACG  ATGAAGACGG
  N  E  K     D  T  S     I  F  I  K    N  E  F    T  F  Y     D  E  D  G 2290                        2310                        2330
TAATCCCATC  GACTTTGATA  ATGCCCTCTT  GTCAGTTGCC  TCCCTTAACA  GGGAACACAA
  N  P  I     D  F  D     N  A  L  L    S  V  A    S  L  N     R  E  H  N 2350                        2370                        2390
TTCCATTGAG  ATGGCCAAGG  ACTACAGCGG  TACCTTCGTT  AAGATTTCTG  GCTCATCCAT
  S  I  E     M  A  K     D  Y  S  G    T  F  V    K  I  S     G  S  S  I 2410                        2430                        2450
TGGTGAAAAA  AATGGCATGA  TCTATGCGAC  CGACACCCTC  AACTTTAAAA  AGGGTGAAGG
  G  E  K     N  G  M     I  Y  A  T    D  T  L    N  F  K     K  G  E  G 2470                        2490                        2510
CGGTTCCCTT  CACACCATGT  ACACCAGAGC  AAGTGAGCCT  GGTTCAGGTT  GGGACTCTGC
  G  S  L     H  T  M     Y  T  R  A    S  E  P    G  S  G     W  D  S  A 2530                        2550                        2570
TGATGCTCCT  AATTCTTGGT  ATGGTGCTGG  TGCTGTCAGA  ATGTCCGGCC  CAAACAACTA
  D  A  P     N  S  W     Y  G  A  G    A  V  R    M  S  G     P  N  N  Y 2590                        2610                        2630
CATCACTTTG  GGGGCAACCT  CAGCGACCAA  TGTCCTCAGC  CTAGCTGAAA  TGCCACAGGT
  I  T  L     G  A  T     S  A  T  N    V  L  S    L  A  E     M  P  Q  V 2650                        2670                        2690
ACCTGGTAAA  GATAATACTG  CTGGTAAAAA  ACCAAATATC  TGGTATTCCC  TTAATGGTAA
  P  G  K     D  N  T     A  G  K  K    P  N  I    W  Y  S     L  N  G  K 2710                        2730                        2750
GATTCGGGCA  GTCAATGTCC  CTAAAGTGAC  CAAGGAAAAA  CCAACCCCAC  CAGTTGAGCC
  I  R  A     V  N  V     P  K  V  T    K  E  K    P  T  P     P  V  E  P 2770                        2790                        2810
AACCAAGCCA  GACGAGCCAG  TCTATGAAGT  TGAGAAGGAA  TTGGTAGATC  TGCCAGTTGA
  T  K  P     D  E  P     V  Y  E  V    E  K  E    L  V  D     L  P  V  E 2830                        2850                        2870
ACCAAGCTAC  GAAAAGGAAC  CAACCCCACC  AAGCAAGACT  CCAGACCAAA  ATATCCCAGA
  P  S  Y     E  K  {E     P  T  P  P    S  K  T    P  D  Q     N  I  P  D
              P1
```

TABLE 4-continued

Full sequence of cloned *S.sobrinus* gene (SEQ ID NO:22) and corresponding amino acid sequence (SEQ ID NO:23)

```
             2890                              2910                              2930
CAAACCAGTA  GAGCCTACTT  ATGAGGTTGA  AAAGGAGCTG  GAACCGGCAC  CAGTTGAGCC
 K   P   V   E   P   T   Y   E   V   E   K   E   L   E   P   A   P   V   E   P 2950                              2970                              2990
AAGCTACGAA  AAGGAACCAA  CGCCACCAAG  CAAGACTCCG  GATCAAGCGA  TTCCAGACAA
 S   Y   E   K} {E   P   T   P   P   S   K   T   P   D   Q   A   I   P   D   K
             P2

3010                              3030                              3500
ACCGGTAGAG  CCAACCTATG  AGGTTGAAAA  GGAGTTGGAA  CCAGTACCTG  TAGAAACAAA
 P   V   E   P   T   Y   E__V   E   K   E   L   E   P   V   P   V   E   T   N 3070                              3090                              3110
CTACGAAAAG  GAACCAACCC  CGCCTCAGTC  AACCCCAGAC  CAAGAAGAGC  CCACCAAACC
 Y   E   K} {E   P   T   P   P   Q   S   T   P   D   Q   E   E   P   T   K   P
             P3

3130                              3150                              3170
GGTGGAACCA  AGCTACCAAA  GCTTGCCAAC  CCCACCAGTG  GCACCGACTT  ATGAAAAGGT
 V   E   P   S   Y   Q}  S   L   P   T   P   P   V   A   P   T   Y   E   K   V 3190                              3210                              3230
TCCTGGTCCT  GTCAGTGTGC  CAACGGTTCG  GTACCACTAC  TATAAACTAG  CGGTCCAACC
 P   G   P   V   S   V   P   T   V   R   Y   H   Y   Y   K   L   A   V   Q   P 3250                              3270                              3290
CGGCGTCACC  AAGAAAATCA  AAAACCAGGA  TGACCTGGAT  ATTGACAAGA  CCCTGGTGGC
 G   V   T   K   K   I   K   N   Q   D   D   L   D   I   D   K   T   L   V   A 3310                              3330                              3350
TAAGCAGTCG  ACGGTTAAGT  TCCAATTGAA  GACAGCAGAC  CTGCCAGCCG  GTCGTCCAGA
 K   Q   S   T   V   K   F   Q   L   K   T   A   D   L   P   A   G   R   P   E 3370                              3390                              3410
AACGACCTCC  TTTGTCTTGA  TGGATCCTCT  GCCAAGCGGT  TACCAACTTA  ATCTGGAAGC
 T   T   S   F   V   L   M   D   P   L   P   S   G   Y   Q   L   N   L   E   A 3430                              3450                              3470
TACCAAGGTC  GCCAGCCCAG  GCTTTGAAGC  TAGCTATGAT  GCCATGACCC  ATACGGTAAC
 T   K   V   A   S   P   G   F   E   A   S   Y   D   A   M   T   H   T   V   T 3490                              3510                              3530
CTTCATCGCA  ACCGCTGAGA  CCTTGGCGGC  GCTCAACCAG  GATCTGACCA  AGGCCGTGGC
 F   I   A   T   A   E   T   L   A   A   L   N   Q   D   L   T   K   A   V   A 3550                              3570                              3590
GACTATCTAC  CCAACAGTTG  TGGGACAAGT  CCTCAACGAT  GGCGCTACCT  ACACCAATAA
 T   I   Y   P   T   V   V   G   Q   V   L   N   D   G   A   T   Y   T   N   N 3610                              3630                              3650
CTTCACCCTG  ATGGTCAATG  ATGCTTACGG  TATTAAATCC  AATATCGTTC  GCGTGACCAC
 F   T   L   M   V   N   D   A   Y   G   I   K   S   N   I   V   R   V   T   T 3670                              3690                              3710
ACCAGGGAAA  CCTAACGACC  CAGACAACCC  AAGCAACAAC  TACATCACCC  CGCACAAGGT
 P   G   K   P   N   D   P   D   N   P   S   N   N   Y   I   T   P   H   K   V 3730                              3750                              3770
CAACAAGAAT  GAAAACGGTG  TGGTGATTGA  TGGTAAGTCC  GTCCTAGCTG  GTACCACCAA
 N   K   N   E   N   G   V   V   I   D   G   K   S   V   L   A   G   T   T   N 3790                              3810                              3830
CTACTATGAA  TTGACTTGGG  ACCTGGACCA  ATACAAGGGC  GATAAATCGG  CCAAGGAGAC
 Y   Y   E   L   T   W   D   L   D   Q   Y   K   G   D   K   S   A   K   E   T 3850                              3870                              3890
CATCCAAAAA  GGCTTCTTCT  ATGTGGATGA  CTATCCTGAA  GAAGCGCTGG  ACTTGCGCAC
 I   Q   K   G   F   F   Y   V   D   D   Y   P   E   E   A   L   D   L   R   T 3910                              3930                              3950
CGACCTGATT  AAGCTGACCG  ATGCCAACGG  CAAGGCGGTC  ACTGGTGTCA  GCGTGGCTGA
 D   L   I   K   L   T   D   A   N   G   K   A   V   A   G   V   S   V   A   D 3970                              3990                              4010
CTACGCCAGT  CTGGAGGCCG  CACCAGCAGC  TGTTCAAGAC  ATGCTCAAGA  AGGCCAACAT
 Y   A   S   L   E   A   A   P   A   A   V   Q   D   M   L   K   K   A   N   I
```

TABLE 4-continued

Full sequence of cloned *S.sobrinus* gene (SEQ ID NO:22) and corresponding amino acid sequence (SEQ ID NO:23)

```
        4030                  4050                  4070
TACCCCTAAG GGAGCCTTCC AAGTCTTTAC CGCTGACGAT CCTCAGGCCT TCTACGATGC
  T  P  K    G  A  F    Q  V  F  T    A  D  D    P  Q  A    F  Y  D  A 4090                  4110                  4130
CTATGTGGTT ACCGGAACTG ACCTGACCAT CGTCACTCCA ATGACGGTCA AGGCTGAGAT
  Y  V  V    T  G  T    D  L  T  I    V  T  P    M  T  V    K  A  E  M 4150                  4170                  4190
GGGCAAGATC GGTGGTAGCT ATGAAAACAA GGCCTACCAG ATTGACTTTG GTAATGGCTA
  G  K  I    G  G  S    Y  E  N  K    A  Y  Q    I  D  F    G  N  G  Y 4210                  4230                  4250
TGAATCTAAT ATTGTGATTA ACAATGTGCC GCAAATCAAT CCTGAAAAGG ATGTGACCTT
  E  S  N    I  V  I    N  N  V  P    Q  I  N    P  E  K    D  V  T  L 4270                  4290                  4310
GACCATGGAT CCAGCGGATA GTACCAATGT GGATGGACAG ACCATCGCCC TCAATCAGGT
  T  M  D    P  A  D    S  T  N  V    D  G  Q    T  I  A    L  N  Q  V 4330                  4350                  4370
CTTTAACTAC CGTCTCATCG GTGGTATCAT TCCAGCGGAC CATGCCGAAG AGCTCTTTGA
  F  N  Y    R  L  I    G  G  I  I    P  A  D    H  A  E    E  L  F  E 4390                  4410                  4430
GTACAGCTTT AGCGATGACT ATGACCAAAC TGGAGACCAG TACACGGGCC AATACAAGGC
  Y  S  F    S  D  D    Y  D  Q  T    G  D  Q    Y  T  G    Q  Y  K  A 4450                  4470                  4490
CTTTGCCAAG GTTGACCTGA CCCTCAAGGA TGGTACAATC ATCAAGGCGG GTACTGACTT
  F  A  K    V  D  L    T  L  K  D    G  T  I    I  K  A    G  T  D  L 4510                  4530                  4550
GACTTCATAT ACAGAAGCGC AAGTTGATGA AGCTAATGGC CAAATTGTTG TGACCTTCAA
  T  S  Y    T  E  A    Q  V  D  E    A  N  G    Q  I  V    V  T  F  K 4570                  4590                  4610
GGAAGATTTC TTGCGGTCTG TGTCTGTAGA CTCGGCCTTC CAAGCGGAAG TCTACCTACA
  E  D  F    L  R  S    V  S  V  D    S  A  F    Q  A  E    V  Y  L  Q 4630                  4650                  4670
GATGAAGCGG ATAGCCGTCG GGACCTTTGC CAATACCTAT GTCAATACGG TCAATGGAAT
  M  K  R    I  A  V    G  T  F  A    N  T  Y    V  N  T    V  N  G  I 4690                  4710                  4730
TACCTATAGC TCTAATACGG TAAGGACCAG CACACCAGAG CCGAAGCAGC CAAGTCCAGT
  Y  Y  S    S  N  T    V  R  T  S    T  P  E    P  K  Q    P  S  P  V 4750                  4770                  4790
GGTACCTAAG ACCACTACTA CGGTAGTCTT CCAGCCTCGT CAGGGTCAAG CTTATCAGCC
  V  P  K    T  T  T    T  V  V  F    Q  P  R    Q  G  Q    A  Y  Q  P 4810                  4830                  4850
AGCGCCGCCA GCAGGAGCTC AATTGCCAGC CACAGGGGAT AGTAGCAATG CTTACCTGCC
  A  P  P    A  G  A    Q  L  P  A    T  G  D    S  S  N    A  Y  L  P 4870                  4890                  4910
ACTTTTAGGC CTCGTAAGCC TGACTGCTGG CTTTAGCCTG TTAGGACTGC GCCGGAAGCA
  L  L  G    L  V  S    L  T  A  G    F  S  L    L  G  L    R  R  K  Q 4930                  4950                  4970
GGACTAAAGA ATCCAACAAG AAAAAATGGG AAAGTTTGCC TTTCTCATTT TTTATATTCC
  D  *

4990                  5010                  5030
CAGCTAGCTG AGTAGTCAAG AAGTACTCTT AGAAAACCCT AGAGAACATT AGCTAACTTT 5050                  5070
TCCAAACCGA TAGACGTTTA TTTTAGTCTA AGTATGG
```

TABLE 5

The *S.oralis* DNA Sequence Encoding an Endocarditis - Specific Antigen
Region (SEQ ID NO:2) and corresponding amino acid sequence (SEQ ID NO:1)

| 5' | 10 | | | 30 | | | 50 | |
|---|---|---|---|---|---|---|---|---|
| GAATTCACCT | TCTACGATGA | AATGACCAA | CCAATTAATT | TTGACAATGC | TCTTCTTTCA |
| E F T | F Y D E | N D Q | P I N | F D N A | L L S |

| | 70 | | | 90 | | | 110 | |
|---|---|---|---|---|---|---|---|---|
| GTAGCCTCAC | TTAACCGTGA | GCATAACTCT | ATTGAGATGG | CTAAGGATTA | TAGTGGYACT |
| V A S | L N R E | H N S | I E M | A K D Y | S G T |

| | 130 | | | 150 | | | 170 | |
|---|---|---|---|---|---|---|---|---|
| TTTATTAAAA | TCTCAGGTTC | ATCCATCGGT | GAAAAAAATG | GCATGATTTA | TGCCACAGAA |
| F I K | I S G S | S I G | E K N | G M I Y | A T E |

| | 190 | | | 210 | | | 230 | |
|---|---|---|---|---|---|---|---|---|
| ACCCTGAACT | TTAAACAAGG | ACAGGGTGGA | GCTCGCTGGA | CAATGTATCC | AAATCGTCAG |
| T L N | F K Q G | Q G G | A R W | T M Y P | N R Q |

| | 250 | | | 270 | | | 290 | |
|---|---|---|---|---|---|---|---|---|
| CCAGGTTCAG | GTTGGGATTC | ATCAGATGCA | CCAAACTCTT | GGTACGGTGC | AGGGGCCATT |
| P G S | G W D S | S D A | P N S | W Y G C | G A I |

| | 310 | | | 330 | | | 350 | |
|---|---|---|---|---|---|---|---|---|
| AGTATGTCCG | GTCCTACGAA | TCACGTTACA | GTTGGTGCAA | CATCTGCTAC | CAATGTGATG |
| S M S | G P T N | H V T | V G A | T S A T | N V M |

| | 370 | | | 390 | | | 410 | |
|---|---|---|---|---|---|---|---|---|
| TCCGTAGCAG | AAATGCCTCA | AGTACCTGGA | AGAGACAATA | CTGAAGGTAA | AAGACCAAAC |
| S V A | E M P Q | V P G | R D N | T E G K | R P N |

| | 430 | | | 450 | | | 470 | |
|---|---|---|---|---|---|---|---|---|
| ATCTGGTACT | CACTCAATGG | TAAAATTCGT | GCGGTTGACG | TTCCGAAAAT | TACAAAAGAA |
| I W Y | S L N G | K I R | A V D | V P K I | T K E |

| | 490 | | | 510 | | | 530 | |
|---|---|---|---|---|---|---|---|---|
| AAACCAACTC | CACCGGTAGC | ACCAACTGAA | CCACAAGCTC | CTACCTATGA | AGTGGAGAAA |
| K P T | P P V A | P T E | P Q A | P T Y E | V E K |

| | 550 | | | 570 | | | 590 | |
|---|---|---|---|---|---|---|---|---|
| CCACTGGAAC | CGGCTCCAGT | AGCACCAAGC | TACGAAAATG | AGCCAACTCC | ACCAGTAAAA |
| P L E | P A P V | A P S | Y E N | {E P T P P1 | P V K |

| | 610 | | | 630 | | | 650 | |
|---|---|---|---|---|---|---|---|---|
| ACTCCAGATC | AACCGGAGCC | ATCAAAACCA | GAAGAGCCAA | CATATGAGAC | AGAGAAACCA |
| T P D | Q P E P | S K P | E E P | T Y E T | E K P |

| | 670 | | | 690 | | | 710 | |
|---|---|---|---|---|---|---|---|---|
| TTGGAACCAG | CTCCAGTAGC | ACCAAACTAC | GAAAATGAGC | CAACTCCACC | AGTAAAAACT |
| L E P | A P V A | P N Y | E N}{E P2 | P T P P | V K T |

| | 730 | | | 750 | | | 770 | |
|---|---|---|---|---|---|---|---|---|
| CCAGATCAAC | CAGACCCATC | AAAACCGGAA | GAGCCAAACT | ATGAGACAGA | GAAACCATTG |
| P D Q | P D P S | K P E | E P N | Y E T E | K P L |

| | 790 | | | 810 | | | 830 | |
|---|---|---|---|---|---|---|---|---|
| GAACCAGCTC | CAGTAGCACC | AAGCTATGAA | AATGAGCCAA | CTCCACCGGT | AAAAACTCCA |
| E P A | P V A P | S Y E | N}{E P P3 | T P P V | K T P |

| | 850 | | | 870 | | | 890 | |
|---|---|---|---|---|---|---|---|---|
| GATCAACCAG | AGCCATCAAA | ACCAGAAGAG | CCAAATTATG | ATCCATTGCC | AACTCCGCCG |
| D Q P | E P S K | P E E | P N Y | D} P L P | T P P |

| | 910 | | | 930 | | | 950 | |
|---|---|---|---|---|---|---|---|---|
| CTAGCACCAA | CTCCTAAGCA | GTTGCCAACA | CCACCAGCGG | TGCCAACAGT | TCACTTCCAT |
| L A P | T P K Q | L P T | P P A | V P T V | H F H |

| | 970 | | | 990 | | | 1010 | |
|---|---|---|---|---|---|---|---|---|
| TACAATCGTC | TATTTGCACA | ACCCTCAGATT | AATAAAGAAA | TTAAAAACGA | GGATGGAGTA |
| Y N R | L F A Q | P Q I | N K E | I K N E | D G V |

| | 1030 | | | 1050 | | | 1070 | |
|---|---|---|---|---|---|---|---|---|
| GATATTGATC | GTACTCTAGT | TGCTAAGCAG | TCTGTAGTGA | AGTTTGAGCT | GAAAACAGAA |
| D I D | R T L V | A K Q | S V V | K F E L | K T E |

TABLE 5-continued

The *S.oralis* DNA Sequence Encoding an Endocarditis - Specific Antigen
Region (SEQ ID NO:2) and corresponding amino acid sequence (SEQ ID NO:1)

```
        1090                              1110                            1130
GCTTTAACTG  CTGGTCGTCC  AAAAACAACT  TCGTTTGTAT  TGGTAGATCC  ACTTCCAACT
 A  L  T     A  G  R  P    K  T  T     S  F  V     L  V  D  P    L  P  T 1150                              1170                            1190
GGCTATCAGT  TTGATTTGGA  AGCAACCAAG  GCTGCAAGCA  AAGGTTTTGA  AACAAGCTAT
 G  Y  Q     F  D  L  E   A  T  K     A  A  S     K  G  F  E    T  S  Y 1210                              1230                            1250
GACAAAGCTA  GTCACACTGT  AACCTTTAAG  GCTACTGAGG  AGACCTTAGC  TGCTTTCAAT
 D  K  A     S  H  T  V   T  F  K     A  T  E     E  T  L  A    A  F  N 1270                              1290                            1310
GCTGATTTGA  CAAAATCCTT  TGAGACTCTA  TATCCAACTG  TTGTTGGTCG  TGTCTTGAAT
 A  D  L     T  K  S  F   E  T  L     Y  P  T     V  V  G  R    V  L  N 1330                              1350                            1370
GATGGGGCGA  CTTATACGAA  TAACTTTACA  TTGACAGTCA  ACGATGCTAC  TGGTGTCAAG
 D  G  A     T  Y  T  N   N  F  T     L  T  V     N  D  A  T    G  V  K 1390                              1410                            1430
TCAAACATTG  TTCGTGTAAC  GACTCCAGGT  AAACCAAATG  ATCCTGACAA  TCCAAATAAC
 S  N  I     V  R  V  T   T  P  G     K  P  N     D  P  D  N    P  N  N 1450                              1470                            1490
AACTACATCA  AGCCTTTGAA  AGTTAACAAG  AACAAGCAAG  GTGTGAATAT  TGATGGCAAA
 N  Y  I     K  P  L  K   V  N  K     N  K  Q     G  V  N      D  G  K 1510                              1530                            1550
GAAGTTCTAG  CTGGTTCAAC  GAACTACTAT  GAACTCACAT  GGGATTTGGA  TCAATACAAG
 E  V  L     A  G  S  T   N  Y  Y     E  L  T     W  D  L  D    Q  Y  K 1570                              1590                            1610
GGAGATAAAT  CTTCTAAAGA  AGCGATTCAA  AATGGTTTCT  ACTATGTGGA  TGATTATCCA
 G  D  K     S  S  K  E   A  I  Q     N  G  F     Y  Y  V  D    D  Y  P 1630                              1650                            1670
GAAGAAGCTT  TAACGCTTCA  ACCCAGAATTG  GTTAAGATTC  GTGATCTAGA  GGGCAACCTT
 E  E  A     L  T  L  Q    P  E  L     V  K  I     R  D  L  E    G  N  L 1690                              1710                            1730
GTATCAGGTA  TCAGTGTTCA  ACAGTTTGAT  AGTTTAGAAC  GTGCGCCTAA  GAAGGTTCAA
 V  S  G     I  S  V  Q    Q  F  D     S  L  E     R  A  P  K    K  V  Q 1750                              1770                            1790
GATCTGTTGA  AGAAAGCAAA  CATCACTGTT  AAAGGTGCTT  TCCAACTCTT  CTCAGCTGAT
 D  L  L     K  K  A  N   I  T  V     K  G  A     F  Q  L  F    S  A  D

1810
AATCCAGCTG  AATTC
 N  P  A    E  F
```

This 1.81 kb DNA fragment carried the three tandem repeat proline (P1–3) common to the family of antigen 1/11 proteins important in dental caries. The repeat proline rich refion of this amino acid sequences was bracketed ({ }) as above.

TABLE 6

| Peptide Number | Amino Acid Sequence |
|---|---|
| 1 | YEVEKPLEPAPVAPS (SEQ ID NO:3) |
| 2 | SYENEPTPPVKTPD (SEQ ID NO:4) |
| 3 | KTPDQPEPSKPEEPT (SEQ ID NO:5) |
| 4 | EPAPVAPSYENEPTP (SEQ ID NO:6) |
| 5 | YEVEKELVDLPVEPS (SEQ ID NO:7) |
| 6 | KTPDQNIPDKPVEPT (SEQ ID NO:8) |

TABLE 7

Clinical History of Serum

| | Peptide Number | | | | | | | | | | | |
|---|---|---|---|---|---|---|---|---|---|---|---|---|
| | 1 | | 2 | | 3 | | 4 | | 5 | | 6 | |
| | M | G | M | G | M | G | M | G | M | G | M | G |
| S. mutans endocarditis | 0.341 | 1.506 | 0.331 | 0.381 | 0.338 | 1.365 | 0.445 | 1.225 | 0.261 | 1.491 | 0.241 | 0.869 |
| S. oralis endocarditis | 0.442 | 0.902 | 0.561 | 0.891 | 0.491 | 0.768 | 0.567 | 0.936 | 0.653 | 0.784 | 0.373 | 0.873 |
| S. oralis septicaemia | 0.024 | 0.118 | 0.036 | 0.215 | 0.019 | 0.123 | 0.065 | 0.168 | 0.043 | 0.241 | 0.117 | 0.218 |
| S. lactis endocarditis | 0.306 | 0.589 | 0.319 | 0.528 | 0.309 | 0.492 | 0.377 | 0.415 | 0.337 | 0.421 | 0.244 | 0.449 |
| S. aureus endocarditis | 0.075 | 0.177 | 0.145 | 0.579 | 0.068 | 0.153 | 0.015 | 0.127 | 0.101 | 0.267 | 0.063 | 0.217 |

ELISA readings for peptides 1–6

TABLE 8

Indirect ELISA results for Peptide 1
Concentration of peptide: 200 μl at 10 μg/ml
Primary antibody 1/100

| Patient No. | Sera Date | Mean[a] Blank O.D. | Mean Sample O.D.[b] IgM | Mean Sample O.D.[b] IgG | Standard Deviation IgM | Standard Deviation IgG |
|---|---|---|---|---|---|---|
| *S. mutans* Endocarditis | | | | | | |
| 1 | 16.03.88 | 0.131 | 0.117 | 0.698 | 0.001 | 0.015 |
| 2 | 17.09.87 | 0.193 | 0.012 | 6.742 | 0.003 | 0.0017 |
| *S. oralis* Endocarditis (n = 3) | | | | | | |
| 3 | 23.05.78 | 0.141 | 0.462 | 0.960 | 0.018 | 0.002 |
| 4 | 12.12.81 | 0.197 | 0.447 | 0.902 | 0.023 | 0.031 |
| 5 | 23.02.84 | 0.121 | 0.043 | 0.038 | 0.001 | 0.008 |
|  | 30.08.84 | 0.131 | 0.153 | 0.699 | 0.004 | 0.007 |
| *S. gordonii* Endocarditis (n = 14) | | | | | | |
| 6 | 1.07.86 | 0.131 | 0.422 | 0.936 | 0.001 | 0.002 |
|  | 15.08.86 | 0.131 | 0.339 | 0.855 | 0.003 | 0.004 |
|  | 22.09.86 | 0.131 | 0.228 | 0.81 | 0.010 | 0.005 |
|  | 6.10.96 | 0.131 | 0.173 | 1.06 | 0.003 | 0.002 |
| 7 | 8.01.87 | 0.131 | 0.487 | 0.685 | 0.010 | 0.012 |
| 8 | 18.12.86 | 0.131 | 0.059 | 0.662 | 0.004 | 0.006 |
|  | 21.01.87 | 0.131 | 0.270 | 0.715 | 0.005 | 0.009 |
| 9 | 10.08.86 | 0.131 | 0.43 | 0.41 | 0.007 | 0.004 |
| 10 | 17.07.86 | 0.131 | 0.568 | 0.601 | 0.010 | 0.012 |
| 11 | 14.07.93 | 0.131 | 0.095 | 0.471 | 0.012 | 0.003 |
| 12 | 20.03.93 | 0.158 | 0.164 | 0.404 | 0.001 | 0.03 |
|  | 22.03.93 | 0.158 | 0.168 | 0.475 | 0.003 | 0.03 |
| 13 | 06.05.87 | 0.121 | 0.438 | 0.079 | 0.023 | 0.003 |
|  | 12.08.87 | 0.121 | 0.274 | 0.579 | 0.021 | 0.016 |
| 14 | 7.06.86 | 0.131 | 0.174 | 0.459 | 0.006 | 0.024 |
|  | 9.06.86 | 0.151 | 0.144 | 0.469 | 0.004 | 0.013 |
|  | 16.06.86 | 0.153 | 0.151 | 0.587 | 0.005 | 0.011 |
|  | 19.06.86 | 0.193 | 0.134 | 0.706 | 0.006 | 0.008 |
|  | 23.06.86 | 0.151 | 0.149 | 0.562 | 0.007 | 0.011 |
|  | 26.06.86 | 0.153 | 0.106 | 0.475 | 0.005 | 0.017 |
| 15 | 2.12.57 | 0.012 | 0.301 | 1.391 | 0.006 | 0.011 |
|  | 30.12.87 | 0.131 | 0.217 | 1.083 | 0.005 | 0.007 |
| *S. sanguis* Endocarditis (n = 2) | | | | | | |
| 16 | 21.07.86 | 0.121 | 0.46 | 0.543 | 0.006 | 0.011 |
|  | 7.08.86 | 0.121 | 0.487 | 0.685 | 0.001 | 0.011 |
| 17 | 14.07.93 | 0.121 | 0.416 | 0.401 | 0.049 | 0.022 |
| *S. oralis* Septicaemics (n = 8) | | | | | | |
| 18 | 23.11.88 | 0.133 | 0.046 | 0.112 | 0.017 | 0.001 |
|  | 6.12.88 | 0.131 | 0.024 | 0.118 | 0.001 | 0.004 |
| 19 | 22.08.89 | 0.131 | 0.023 | 0.194 | 0.001 | 0.003 |
|  | 6.09.89 | 0.144 | 0.034 | 0.205 | 0.0016 | 0.001 |
|  | 17.10.89 | 0.121 | 0.006 | 0.042 | 0.003 | 0.004 |
| 20 | 11.03.88 | 0.197 | 0.007 | 0.048 | 0.018 | 0.008 |
|  | 1.04.88 | 0.133 | 0.043 | 0.102 | 0.003 | 0.011 |
|  | 10.05.88 | 0.197 | 0.021 | 0.014 | 0.001 | 0.001 |
| 21 | 27.06.89 | 0.197 | 0.058 | 0.031 | 0.015 | 0.021 |
|  | 1.80.89 | 0.151 | 0.003 | 0.095 | 0.002 | 0.001 |
| 22 | 2.08.88 | 0.144 | 0.017 | 0.082 | 0.001 | 0.014 |
| 23 | 4.04.89 | 0.135 | 0.044 | 0.061 | 0.002 | 0.002 |
| 24 | 22.03.93 | 0.193 | 0.029 | 0.022 | 0.001 | 0.001 |
|  | 22.04.93 | 0.158 | 0.032 | 0.041 | 0.003 | 0.001 |
|  | 26.04.93 | 0.139 | 0.034 | 0.044 | 0.011 | 0.021 |
|  | 27.04.93 | 0.158 | 0.042 | 0.036 | 0.001 | 0.009 |
| 25 | 21.07.93 | 0.139 | 0.089 | 0.027 | 0.003 | 0.009 |
|  | 21.07.93 | 0.139 | 0.113 | 0.031 | 0.009 | 0.005 |
|  | 4.08.93 | 0.139 | 0.129 | 0.032 | 0.001 | 0.008 |
|  | 17.08.93 | 0.139 | 0.095 | 0.103 | 0.003 | 0.019 |
| *E. faecalis* Endocarditis | | | | | | |
| 26 | 25.02.93 | 0.141 | 0.027 | 0.075 | 0.001 | 0.014 |
|  | 25.02.93 | 0.141 | 0.024 | 0.063 | 0.001 | 0.003 |
|  | 29.02.93 | 0.141 | 0.026 | 0.071 | 0.003 | 0.001 |
| 27 | 15.06.93 | 0.147 | 0.085 | 0.248 | 0.003 | 0.007 |
|  | 16.06.93 | 0.147 | 0.071 | 0.275 | 0.002 | 0.013 |
| 28 | 20.01.92 | 0.141 | 0.041 | 0.069 | 0.004 | 0.001 |
| 29 | 24.06.88 | 0.153 | 0.085 | 0.283 | 0.003 | 0.017 |
| 30 | 10.06.86 | 0.135 | 0.054 | 0.361 | 0.003 | 0.012 |
| 31 | 19.11.87 | 0.133 | 0.033 | 0.652 | 0.009 | 0.006 |
| 32 | 29.01.89 | 0.131 | 0.081 | 0.564 | 0.011 | 0.016 |
|  | 13.10.89 | 0.133 | 0.024 | 0.281 | 0.003 | 0.022 |
|  | 16.11.89 | 0.197 | 0.016 | 0.195 | 0.006 | 0.005 |
|  | 8.01.90 | 0.133 | 0.043 | 0.371 | 0.008 | 0.018 |
| 33 | 10.05.88 | 0.197 | 0.096 | 1.079 | 0.003 | 0.018 |
|  | 15.05.88 | 0.131 | 0.088 | 1.011 | 0.003 | 0.018 |
|  | 21.05.88 | 0.131 | 0.048 | 0.531 | 0.002 | 0.015 |
|  | 28.08.88 | 0.131 | 0.156 | 0.674 | 0.003 | 0.013 |
| 34 | 6.11.86 | 0.141 | 0.086 | 0.082 | 0.013 | 0.001 |
| 35 | 12.01.87 | 0.144 | 0.039 | 0.387 | 0.008 | 0.022 |
| 36 | 5.01.87 | 0.135 | 0.011 | 0.559 | 0.001 | 0.015 |
| *E. faecalis* Septicaemics | | | | | | |
| 37 | 30.12.87 | 0.133 | 0.029 | 0.371 | 0.001 | 0.007 |
| 38 | 10.10.85 | 0.193 | 0.018 | 0.175 | 0.004 | 0.025 |
| 39 | 24.08.89 | 0.193 | 0.033 | 0.002 | 0.003 | 0.002 |

TABLE 8-continued

Indirect ELISA results for Peptide 1
Concentration of peptide: 200 μl at 10 μg/ml
Primary antibody 1/100

| Patient No. | Sera Date | Mean[a] Blank O.D. | Mean Sample O.D.[b] IgM | IgG | Standard Deviation IgM | IgG |
|---|---|---|---|---|---|---|
| | 11.10.85 | 0.151 | 0.052 | 0.266 | 0.001 | 0.008 |
| | 11.10.85 | 0.153 | 0.049 | 0.218 | 0.011 | 0.014 |
| 40 | 8.01.88 | 0.135 | 0.041 | 0.286 | 0.019 | 0.001 |
| 41 | 27.11.87 | 0.197 | 0.034 | 0.354 | 0.001 | 0.004 |
| 42 | 20.04.85 | 0.144 | 0.02 | 0.132 | 0.003 | 0.006 |
| 43 | 27.06.88 | 0.144 | 0.034 | 0.152 | 0.013 | 0.011 |

*E. faecium* Septicaemics

| 44 | 19.07.85 | 0.197 | 0.135 | 0.436 | 0.015 | 0.026 |
| 45 | 23.10.85 | 0.144 | 0.029 | 0.269 | 0.011 | 0.008 |
| | 28.11.85 | 0.139 | 0.027 | 0.061 | 0.001 | 0.001 |
| | 2.12.85 | 0.139 | 0.055 | 0.057 | 0.003 | 0.003 |

*S. bovis* Endocarditis

| 46 | 8.07.86 | 0.133 | 0.155 | 0.429 | 0.023 | 0.013 |
| 47 | 22.03.85 | 0.193 | 0.027 | 0.021 | 0.002 | 0.003 |
| | 27.03.85 | 0.151 | 0.012 | 0.153 | 0.003 | 0.019 |
| 48 | 12.03.87 | 0.139 | 0.255 | 0.124 | 0.001 | 0.007 |
| | 6.05.87 | 0.121 | 0.438 | 0.079 | 0.023 | 0.003 |
| | 12.08.87 | 0.121 | 0.274 | 0.141 | 0.021 | 0.016 |
| 49 | 30.10.85 | 0.131 | 0.073 | 0.242 | 0.011 | 0.022 |
| 50 | 8.05.86 | 0.153 | 0.162 | 0.593 | 0.001 | 0.019 |
| 51 | 12.04.85 | 0.153 | 0.203 | 0.823 | 0.004 | 0.015 |
| | 26.04.85 | 0.153 | 0.241 | 1.133 | 0.001 | 0.001 |
| | 30.04.85 | 0.193 | 0.025 | 0.501 | 0.002 | 0.011 |
| 52 | 30.12.87 | 0.144 | 0.063 | 0.197 | 0.003 | 0.003 |
| 53 | 18.07.93 | 0.139 | 0.191 | 0.069 | 0.019 | 0.008 |
| | 18.07.93 | 0.139 | 0.177 | 0.066 | 0.009 | 0.004 |
| | 21.07.93 | 0.139 | 0.108 | 0.035 | 0.011 | 0.006 |
| | 21.07.93 | 0.139 | 0.122 | 0.038 | 0.004 | 0.009 |
| | 24.07.93 | 0.139 | 0.135 | 0.054 | 0.003 | 0.008 |
| | 25.07.93 | 0.139 | 0.141 | 0.073 | 0.013 | 0.015 |
| | 25.07.93 | 0.139 | 0.293 | 0.051 | 0.019 | 0.006 |

*S. agalactiae* Endocarditis

| 54 | 20.06.88 | 0.135 | 0.025 | 0.104 | 0.001 | 0.005 |
| | 22.06.88 | 0.135 | 0.088 | 0.484 | 0.019 | 0.011 |

*S. lactis* Endocarditis

| 55 | 24.03.88 | 0.135 | 0.021 | 0.218 | 0.011 | 0.008 |

*S. pneumoniae* Endocarditis

| 56 | 4.12.87 | 0.133 | 0.095 | 0.492 | 0.011 | 0.019 |
| 57 | 16.07.86 | 0.131 | 0.103 | 0.281 | 0.008 | 0.006 |
| 58 | 7.10.86 | 0.144 | 0.101 | 0.591 | 0.009 | 0.003 |
| 59 | 21.10.86 | 0.131 | 0.033 | 0.569 | 0.011 | 0.008 |

Group G *Streptococcal endocarditis*

| 60 | 29.10.86 | 0.131 | 0.131 | 0.651 | 0.009 | 0.019 |
| 61 | 27.03.85 | 0.197 | 0.111 | 0.789 | 0.017 | 0.015 |

NON NEUTROPENIC CONTROLS

*Staphylococcus aureus* Endocarditis

| 62 | 8.02.88 | 0.149 | 0.087 | 0.077 | 0.029 | 0.018 |
| 63 | 28.02.88 | 0.149 | 0.106 | 0.037 | 0.004 | 0.008 |

Coagulase Negative *Stapylococcus Endocarditis*

| 64 | 30.09.89 | 0.139 | 0.054 | 0.062 | 0.007 | 0.001 |
| 65 | 16.06.89 | 0.153 | 0.051 | 0.215 | 0.013 | 0.007 |
| | 1.07.86 | 0.131 | 0.146 | 0.472 | 0.003 | 0.015 |
| 66 | 24.02.87 | 0.139 | 0.243 | 0.083 | 0.001 | 0.025 |
| | 5.03.87 | 0.121 | 0.387 | 0.098 | 0.008 | 0.006 |
| 67 | 2.01.88 | 0.144 | 0.016 | 0.192 | 0.006 | 0.019 |
| 68 | 10.08.86 | 0.144 | 0.029 | 0.287 | 0.012 | 0.019 |
| | 25.10.86 | 0.139 | 0.067 | 0.071 | 0.008 | 0.006 |
| 69 | 15.02.88 | 0.133 | 0.075 | 0.177 | 0.011 | 0.008 |

Endocarditis due to *Candida albicans*

| 70 | 24.10.86 | 0.147 | 0.244 | 0.159 | 0.004 | 0.003 |

Endocarditis due to *Candida parapsilosis*

| 71 | 1.02.88 | 0.153 | 0.077 | 0.192 | 0.006 | 0.008 |
| | 11.06.88 | 0.139 | 0.121 | 0.165 | 0.005 | 0.006 |
| | 18.06.88 | 0.158 | 0.258 | 0.216 | 0.007 | 0.004 |
| 72 | 8.05.86 | 0.139 | 0.087 | 0.081 | 0.008 | 0.007 |

Endocarditis due to *Escherichia coli*

| 73 | 1.07.88 | 0.135 | 0.038 | 0.358 | 0.003 | 0.018 |
| | 2.07.88 | 0.133 | 0.022 | 0.379 | 0.011 | 0.011 |
| | 5.07.88 | 0.197 | 0.073 | 0.344 | 0.008 | 0.002 |

SLE

| 74 | 13.06.93 | 0.158 | 0.327 | 0.167 | 0.004 | 0.011 |
| | 16.06.93 | 0.147 | 0.322 | 0.245 | 0.008 | 0.022 |
| 75 | 2.05.88 | 0.144 | 0.023 | 0.285 | 0.0091 | 0.004 |
| 76 | 18.04.89 | 0.193 | 0.015 | 0.304 | 0.0041 | 0.003 |

Brain abscess due to *Streptococcus milleri*

| 77 | 17.10.86 | 0.153 | 0.182 | 0.312 | 0.006 | 0.022 |
| | 30.10.86 | 0.151 | 0.342 | 0.353 | 0.011 | 0.001 |
| | 6.11.86 | 0.193 | 0.011 | 0.185 | 0.003 | 0.013 |

NEUTROPENIC CONTROLS

| 78 | 7.08.88 | 0.193 | 0.019 | 0.183 | 0.004 | 0.019 |
| 79 | 11.11.86 | 0.151 | 0.101 | 0.251 | 0.013 | 0.009 |
| 80 | 21.10.86 | 0.149 | 0.101 | 0.078 | 0.015 | 0.018 |
| 81 | 25.07.91 | 0.139 | 0.024 | 0.045 | 0.003 | 0.001 |
| 82 | 9.02.89 | 0.012 | 0.151 | 0.147 | 0.003 | 0.003 |
| 83 | 15.06.93 | 0.151 | 0.021 | 0.177 | 0.004 | 0.009 |
| 84 | 23.06.92 | 0.193 | 0.016 | 0.176 | 0.025 | 0.015 |
| 85 | 19.01.88 | 0.149 | 0.108 | 0.033 | 0.015 | 0.001 |
| 86 | 25.10.88 | 0.193 | 0.007 | 0.035 | 0.005 | 0.004 |
| 87 | 21.03.86 | 0.158 | 0.026 | 0.045 | 0.006 | 0.008 |
| 88 | 18.02.86 | 0.139 | 0.037 | 0.081 | 0.001 | 0.008 |
| 89 | 6.08.91 | 0.144 | 0.034 | 0.421 | 0.005 | 0.014 |
| 90 | 24.04.87 | 0.133 | 0.017 | 0.023 | 0.003 | 0.003 |
| 91 | 12.12.89 | 0.144 | 0.013 | 0.047 | 0.001 | 0.004 |
| 92 | 30.10.86 | 0.139 | 0.076 | 0.125 | 0.009 | 0.014 |
| 93 | 2.07.86 | 0.139 | 0.125 | 0.094 | 0.007 | 0.003 |
| 94 | 5.02.87 | 0.149 | 0.119 | 0.032 | 0.001 | 0.003 |
| 95 | 5.09.98 | 0.135 | 0.017 | 0.021 | 0.004 | 0.003 |
| 96 | 5.08.93 | 0.153 | 0.055 | 0.152 | 0.014 | 0.026 |
| 97 | 19.08.93 | 0.158 | 0.022 | 0.058 | 0.001 | 0.004 |
| | 1.09.93 | 0.158 | 0.044 | 0.088 | 0.009 | 0.006 |
| | 14.09.93 | 0.158 | 0.026 | 0.144 | 0.003 | 0.022 |
| 98 | 3.05.87 | 0.141 | 0.131 | 0.252 | 0.004 | 0.014 |

[a]Mean blank O.D., this value was obtained for each microtitre plate by calculation of the mean O.D. for the six wells containing stain only. This mean blank O.D. was subtracted from the each of the sample O.D. measurements to produce the corrected mean sample O.D. value.

[b]Mean sample O.D., this was the value obtained after subtraction of the mean blank O.D. value from the mean of the three O.D. measurements taken from each of the sample wells.

TABLE 8a

Indirect ELISA results
Concentration of peptides: 200 ml at 10 ug/ml
Primary antibody 1/100
[6]Peptide numbers 1, 7 and 8 as before.

| | Mean Sample Optical Density | | | | | |
|---|---|---|---|---|---|---|
| | IgM | | | IgG | | |
| Patient No | 1[a] | 7[a] | 8[a] | 1[a] | 7[a] | 8[a] |
| *S. mutans* Endocarditis | | | | | | |
| 1 | 0.117 | 0.636 | 0.862 | 0.698 | 0.602 | 0.733 |
| *S. oralis* Endocarditis | | | | | | |
| 4 | 0.447 | 0.584 | 1.236 | 0.902 | 0.433 | 0.678 |
| *S. gordonii* Endocarditis | | | | | | |
| 6 | 0.422 | 0.742 | 1.443 | 0.936 | 0.524 | 1.694 |
| 8 | 0.27 | 0.582 | 0.891 | 0.715 | 0.319 | 1.01 |
| 9 | 0.43 | 1.103 | 0.95 | 0.41 | 0.388 | 0.19 |
| 10 | 0.568 | 0.700 | 0.824 | 0.601 | 0.319 | 0.505 |
| 11 | 0.095 | 0.641 | 1.396 | 0.471 | 0.685 | 0.889 |
| 12 | 0.164 | 0.988 | 1.399 | 0.404 | 0.828 | 0.859 |
| 13 | 0.274 | 1.098 | 1.605 | 0.579 | 0.841 | 0.799 |
| 14 | 0.174 | 0.991 | 1.600 | 0.459 | 0.542 | 0.64 |
| *S. sanguis* Endocarditis | | | | | | |
| 16 | 0.46 | 1.335 | 1.366 | 0.543 | 1.802 | 2.267 |
| 17 | 0.417 | 1.126 | 1.07 | 0.401 | 0.335 | 0.632 |
| *S. oralis* Septicaemias | | | | | | |
| 18 | 0.046 | 0.136 | 0.243 | 0.112 | 0.324 | 0.536 |
| 19 | 0.023 | 0.324 | 0.314 | 0.194 | 0.294 | 0.586 |
| 20 | 0.007 | 0.228 | 0.295 | 0.048 | 0.272 | 0.607 |
| 21 | 0.058 | 0.206 | 0.280 | 0.031 | 0.289 | 0.476 |
| 22 | 0.017 | 0.316 | 0.879 | 0.982 | 0.384 | 0.824 |
| 24 | 0.029 | 0.911 | 1.327 | 0.022 | 0.475 | 0.754 |
| 25 | 0.089 | 0.348 | 0.720 | 0.027 | 0.238 | 0.369 |
| *E. faecalis* Endocarditis | | | | | | |
| 26 | 0.027 | 0.344 | 0.390 | 0.075 | 0.376 | 0.636 |
| 32 | 0.081 | 0.226 | 0.317 | 0.564 | 0.388 | 0.756 |
| 35 | 0.039 | 1.133 | 1.228 | 0.387 | 0.906 | 1.086 |
| 36 | 0.011 | 0.549 | 0.926 | 0.559 | 0.591 | 1.176 |
| *E. faecalis* Septicaemias | | | | | | |
| 38 | 0.018 | 0.784 | 1.344 | 0.175 | 0.39 | 0.796 |
| 39 | 0.033 | 0.590 | 0.78 | 0.002 | 0.432 | 0.87 |
| *E. faecium* Septicaemias | | | | | | |
| 45 | 0.144 | 0.47 | 1.228 | 0.269 | 0.588 | 1.086 |
| *S. oralis* Endocarditis | | | | | | |
| 51 | 0.203 | 1.063 | 1.075 | 0.823 | 0.410 | 0.802 |
| *S. aureus* Endocarditis | | | | | | |
| 62 | 0.087 | 0.333 | 0.266 | 0.077 | 0.435 | 0.401 |
| 63 | 0.106 | 0.356 | 0.805 | 0.037 | 0.484 | 0.646 |
| Coagulase negative Staphylococcus endocarditis | | | | | | |
| 64 | 0.054 | 0.596 | 0.879 | 0.062 | 0.612 | 0.829 |
| 68 | 0.029 | 1.502 | 1.205 | 0.287 | 1.446 | 1.521 |
| SLE | | | | | | |
| 74 | 0.327 | 0.697 | 1.509 | 0.167 | 0.542 | 1.839 |
| Brain abscess *S. milleri* | | | | | | |
| 77 | 0.182 | 1.421 | 2.162 | 0.312 | 0.500 | 0.781 |
| Neutropenic Controls | | | | | | |
| 78 | 0.193 | 0.570 | 0.551 | 0.183 | 0.804 | 0.428 |
| 79 | 0.151 | 0.579 | 0.491 | 0.251 | 0.726 | 0.428 |
| 80 | 0.149 | 0.744 | 0.628 | 0.078 | 0.525 | 0.512 |
| 81 | 0.139 | 0.422 | 0.414 | 0.045 | 0.530 | 0.412 |
| 82 | 0.012 | 0.406 | 0.382 | 0.147 | 0.931 | 0.809 |
| 83 | 0.151 | 0.328 | 0.394 | 0.177 | 0.233 | 0.396 |
| 84 | 0.193 | 0.601 | 0.533 | 0.176 | 0.950 | 0.683 |
| 85 | 0.149 | 0.581 | 0.34 | 0.033 | 0.372 | 0.60 |
| 86 | 0.193 | 0.456 | 0.325 | 0.035 | 0.616 | 0.313 |
| 87 | 0.158 | 0.610 | 0.597 | 0.045 | 0.542 | 0.377 |
| 88 | 0.139 | 0.559 | 0.475 | 0.081 | 0.682 | 0.497 |
| 89 | 0.144 | 0.628 | 0.130 | 0.421 | 0.477 | 0.166 |
| 90 | 0.133 | 0.142 | 0.182 | 0.023 | 0.280 | 0.730 |
| 91 | 0.144 | 0.394 | 0.305 | 0.047 | 0.636 | 0.317 |
| 92 | 0.139 | 0.403 | 0.323 | 0.125 | 0.616 | 0.588 |
| 93 | 0.139 | 1.021 | 0.23 | 0.094 | 0.858 | 0.57 |
| 94 | 0.149 | 0.42 | 0.47 | 0.032 | 0.53 | 0.432 |
| 95 | 0.135 | 0.463 | 0.436 | 0.021 | 0.711 | 0.674 |
| 96 | 0.153 | 0.568 | 0.539 | 0.152 | 0.760 | 0.587 |
| 97 | 0.158 | 0.743 | 0.650 | 0.058 | 0.914 | 0.535 |
| 98 | 0.141 | 0.366 | 0.384 | 0.252 | 0.528 | 0.366 |

TABLE 9

| | IgG ≥ 0.6 | IgM ≥ 0.4 | IgM ≥ 0.4 and IgG ≥ 0.6 |
|---|---|---|---|
| *S. mutans* endocarditis | 100% | 0% | 100% |
| *S. oralis* endocarditis | 100% | 66% | 100% |
| *S. gordonii* endocardits | 60% | 50% | 80% |
| *S. sanguis* endocarditis | 50% | 100% | 100% |
| *S. oralis* septicaemias | 0% | 0% | 0% |
| *E. faecalis* endocarditis | 18% | 0% | 18% |
| *E. faecalis* septicaemia | 0% | 0% | 0% |
| *E. faecium* septicaemia | 0% | 0% | 0% |
| *S. bovis* endocardits | 12.5% | 12.5% | 25% |
| *S. agalactiae* endocarditis | 0% | 0% | 0% |
| *S. lactis* endocarditis | 0% | 0% | 0% |
| *S. pneumoniae* endocarditis | 0% | 0% | 0% |
| Group G streptococcal endocarditis | 100% | 0% | 100% |
| *Staphylococcus aureus* endocardits | 0% | 0% | 0% |
| Coagulase Negative endocarditis | 0% | 0% | 0% |
| *Candida albicans* endocarditis | 0% | 0% | 0% |
| *Candida parapsilosis* endocarditis | 0% | 0% | 0% |
| *E. coli* endocarditis | 0% | 0% | 0% |
| SLE | 0% | 0% | 0% |
| *S. milleri* | 0% | 0% | 0% |
| Neutropenic controls | 0% | 0% | 0% |

TABLE 10

| Epitope Number | Epitope Sequence | Negative Control n = 3 O.D. | S.D | Viridans Endocarditis n = 8 O.D. | S.D. | S. oralis Septicaemia n = 5 O.D. | S.D. | S. mutans Endocarditis n = 2 O.D. | S.D. | E. faecalis Endocarditis n = 3 O.D. | S.D. |
|---|---|---|---|---|---|---|---|---|---|---|---|
| 61 | NFKQGQG | 0.400 | 0.027 | 1.039 | 0.353 | 0.429 | 0.200 | 0.833 | 0.125 | 0.588 | 0.054 |
| 62 | (SEQ ID | 0.388 | 0.034 | 0.972 | 0.347 | 0.419 | 0.230 | 0.808 | 0.122 | 0.508 | 0.027 |
| 63 | NO:18) | 0.444 | 0.058 | 0.992 | 0.329 | 0.430 | 0.215 | 0.888 | 0.195 | 0.540 | 0.013 |
| 74 | RQPG | 0.341 | 0.019 | 0.902 | 0.319 | 0.322 | 0.211 | 0.839 | 0.004 | 0.407 | 0.120 |
| 75 | (SEQ ID | 0.283 | 0.033 | 1.038 | 0.470 | 0.351 | 0.180 | 0.891 | 0.011 | 0.450 | 0.119 |
| 76 | NO:14) | 0.282 | 0.034 | 1.053 | 0.474 | 0.455 | 0.180 | 0.917 | 0.029 | 0.493 | 0.140 |
| 77 |  | 0.350 | 0.045 | 0.981 | 0.358 | 0.309 | 0.070 | 1.041 | 0.043 | 0.472 | 0.130 |
| 78 |  | 0.280 | 0.023 | 0.918 | 0.425 | 0.307 | 0.080 | 1.142 | 0.405 | 0.423 | 0.096 |
| 79 |  | 0.282 | 0.015 | 0.781 | 0.312 | 0.271 | 0.091 | 1.005 | 0.418 | 0.373 | 0.084 |
| 90 | SWYGAG | 0.308 | 0.054 | 0.852 | 0.318 | 0.287 | 0.070 | 1.027 | 0.192 | 0.378 | 0.088 |
| 91 | (SEQ ID | 0.316 | 0.069 | 0.924 | 0.340 | 0.328 | 0.080 | 1.064 | 0.138 | 0.428 | 0.136 |
| 92 | NO:15) | 0.344 | 0.076 | 0.917 | 0.429 | 0.298 | 0.060 | 0.914 | 0.033 | 0.377 | 0.115 |
| 93 |  | 0.306 | 0.007 | 0.957 | 0.378 | 0.444 | 0.140 | 1.083 | 0.225 | 0.483 | 0.131 |
| 144 | GKIRAV | 0.306 | 0.072 | 0.824 | 0.318 | 0.348 | 0.180 | 0.779 | 0.129 | 0.389 | 0.115 |
| 145 | (SEQ ID | 0.384 | 0.071 | 1.028 | 0.309 | 0.437 | 0.210 | 0.971 | 0.199 | 0.515 | 0.120 |
| 148 | NO:16) | 0.303 | 0.042 | 0.852 | 0.261 | 0.348 | 0.150 | 0.881 | 0.240 | 0.438 | 0.115 |
| 147 |  | 0.395 | 0.035 | 0.933 | 0.285 | 0.397 | 0.180 | 0.944 | 0.258 | 0.483 | 0.131 |
| 320 | RLFAQPQ | 0.392 | 0.031 | 1.147 | 0.657 | 0.491 | 0.180 | 1.010 | 0.151 | 0.494 | 0.115 |
| 321 | (SEQ ID | 0.453 | 0.049 | 1.209 | 0.417 | 0.548 | 0.230 | 1.284 | 0.300 | 0.649 | 0.171 |
| 322 | NO:17) | 0.467 | 0.124 | 1.145 | 0.356 | 0.531 | 0.190 | 1.289 | 0.346 | 0.593 | 0.116 |
| 359 | AGRPK | 0.395 | 0.043 | 0.921 | 0.295 | 0.401 | 0.200 | 0.749 | 0.177 | 0.480 | 0.040 |
| 360 | (SEQ ID | 0.492 | 0.065 | 1.049 | 0.374 | 0.428 | 0.240 | 0.775 | 0.030 | 0.491 | 0.062 |
| 361 | NO:18) | 0.407 | 0.032 | 0.907 | 0.318 | 0.382 | 0.190 | 0.657 | 0.094 | 0.0462 | 0.067 |
| 362 |  | 0.430 | 0.008 | 1.054 | 0.325 | 0.423 | 0.230 | 0.753 | 0.091 | 0.525 | 0.082 |
| 363 |  | 0.421 | 0.042 | 0.946 | 0.279 | 0.391 | 0.021 | 0.665 | 0.088 | 0.477 | 0.083 |
| 376 | PTGYQFD | 0.277 | 0.035 | 0.791 | 0.479 | 0.428 | 0.080 | 0.762 | 0.190 | 0.339 | 0.095 |
| 377 | (SEQ ID | 0.415 | 0.039 | 1.045 | 0.427 | 0.359 | 0.140 | 1.548 | 0.728 | 0.487 | 0.155 |
| 378 | NO:19) | 0.351 | 0.062 | 0.802 | 0.290 | 0.291 | 0.140 | 1.274 | 0.793 | 0.380 | 0.151 |
| 426 | YPTVV | 0.309 | 0.081 | 0.852 | 0.391 | 0.269 | 0.100 | 1.275 | 0.617 | 0.410 | 0.147 |
| 427 | (SEQ ID | 0.215 | 0.084 | 0.473 | 0.161 | 0.225 | 0.050 | 0.525 | 0.117 | 0.289 | 0.030 |
| 428 | NO:20) | 0.325 | 0.013 | 1.170 | 0.457 | 0.450 | 0.180 | 1.143 | 0.125 | 0.561 | 0.194 |
| 429 |  | 0.339 | 0.046 | 0.964 | 0.336 | 0.413 | 0.150 | 1.050 | 0.179 | 0.488 | 0.165 |
| 430 |  | 0.349 | 0.088 | 0.976 | 0.328 | 0.465 | 0.140 | 1.002 | 0.198 | 0.458 | 0.139 |
| 577 | LLKKA | 0.279 | 0.042 | 0.863 | 0.302 | 0.353 | 0.190 | 0.681 | 0.142 | 0.466 | 0.081 |
| 578 | (SEQ ID | 0.349 | 0.019 | 0.907 | 0.260 | 0.410 | 0.210 | 0.808 | 0.270 | 0.557 | 0.103 |
| 579 | NO:21) | 0.351 | 0.051 | 0.937 | 0.254 | 0.415 | 0.210 | 0.882 | 0.221 | 0.549 | 0.098 |
| 580 |  | 0.395 | 0.077 | 1.035 | 0.267 | 0.423 | 0.210 | 0.898 | 0.183 | 0.587 | 0.124 |
| 581 |  | 0.331 | 0.029 | 0.847 | 0.261 | 0.581 | 0.150 | 0.843 | 0.153 | 0.482 | 0.141 |

TABLE 11

| Peptide Number | Viridans Endocarditis n = 8 | S. oralis Septicaemia n = 5 | S. mutans Endocarditis n = 2 | E. faecalis Endocarditis n = 2 |
|---|---|---|---|---|
| 61 | 7/8 | 1/5 | 2/2 | 0/2 |
| 62 | 5/8 | 1/5 | 2/2 | 0/2 |
| 63 | 5/8 | 1/5 | 2/2 | 0/2 |
| 74 | 6/8 | 0/5 | 2/2 | 0/2 |
| 75 | 7/8 | 0/5 | 2/2 | 0/2 |
| 76 | 7/8 | 0/5 | 2/2 | 0/2 |
| 77 | 6/8 | 0/5 | 2/2 | 0/2 |
| 78 | 6/8 | 0/5 | 2/2 | 0/2 |
| 79 | 4/8 | 0/5 | 2/2 | 0/2 |
| 90 | 5/8 | 0/5 | 2/2 | 0/2 |
| 91 | 5/8 | 0/5 | 2/2 | 0/2 |
| 92 | 5/8 | 0/5 | 2/2 | 0/2 |
| 93 | 5/8 | 0/5 | 2/2 | 0/2 |
| 14 | 6/8 | 0/5 | 1/2 | 0/2 |
| 145 | 7/8 | 1/5 | 2/2 | 0/2 |
| 146 | 6/8 | 0/5 | 2/2 | 0/2 |
| 147 | 6/8 | 0/5 | 2/2 | 0/2 |
| 320 | 7/8 | 1/5 | 2/2 | 0/2 |
| 321 | 8/8 | 1/5 | 2/2 | 1/2 |
| 322 | 7/8 | 1/5 | 2/2 | 0/2 |
| 359 | 6/8 | 1/5 | 1/2 | 0/2 |
| 360 | 7/8 | 1/5 | 2/2 | 0/2 |
| 361 | 5/8 | 1/5 | 1/2 | 0/2 |
| 362 | 7/8 | 1/5 | 1/2 | 0/2 |
| 263 | 6/8 | 1/5 | 1/2 | 0/2 |
| 376 | 4/8 | 0/5 | 1/2 | 0/2 |
| 377 | 6/8 | 0/5 | 2/2 | 0/2 |
| 378 | 4/8 | 0/5 | 2/2 | 0/2 |
| 426 | 4/8 | 0/5 | 2/2 | 0/2 |
| 427 | 1/8 | 0/5 | 0/2 | 0/2 |
| 428 | 7/8 | 1/5 | 2/2 | 0/2 |
| 429 | 7/8 | 0/5 | 2/2 | 0/2 |
| 430 | 5/8 | 0/5 | 2/2 | 0/2 |
| 577 | 5/8 | 0/5 | 1/2 | 0/2 |
| 578 | 6/8 | 1/5 | 1/2 | 0/2 |
| 579 | 6/8 | 1/5 | 2/2 | 0/2 |
| 580 | 8/8 | 1/5 | 2/2 | 0/2 |
| 581 | 5/8 | 0/5 | 2/2 | 0/2 |

Positive is > 0.700

We claim:

1. A purified bacterial protein expressed during infection due to streptococci and isolated from human sera wherein said bacterial protein comprises at least the sequence of formula (I) (SEQ ID NO:1):

```
NH—          10                            30
EFTFYDENDQ  PINFDNALLS  VASLNREHNS

50
IEMAKDYSGT  FIKISGSSIG  EKNGMIYATE 70                              90
TLNFKQGQGG  ARWTMYPNRQ  PGSGWDSSDA

110
PNSWYGAGAI  SMSGPTNHVT  VGATSATNVM 130                             150
SVAEMPQVPG  RDNTEGKRPN  IWYSLNGKIR

170
AVDVPKITKE  KPTPPVAPTE  PQAPTYEVEK 190                             210
PLEPAPVAPS  YENEPTPPVK  TPDQPEPSKP

230
EEPTYEYEKP  LEPAPVAPNY  ENEPTPPVKT 250                             270
PDQPDPSKPE  EPNYETEKPL  EPAPVAPSYE

290
NEPTPPVKTP  DQPEPSKPEE  PNYDPLPTPP 310                             330
LAPTPKQLPT  PPAVPTVHFH  YNRLFAQPQI

350
NKEIKNEDGV  DIDRTLVAKQ  SVVKFELKTE 370                             390
ALTAGRPKTT  SFVLVDPLPT  GYQFDLEATK

410
AASKGFETSY  DKASHTVTFK  ATEETLAAFN 430                             450
ADLTKSFETL  YPTVVGRVLN  DGATYTNNFT

470
LTVNDATGVK  SNIVRVTTPG  KPNDPDNPNN 490                             510
NYIKPLKVNK  NKQGVNIDGK  EVLAGSTNYY

530
ELTWDLDQYK  GDKSSKEAIQ  NGFYYVDDYP 550                             570
EEALTLQPEL  VKIRDLEGNL  VSGISVQQFD

590
SLERAPKKVQ  DLLKKANITV  KGAFQLFSAD

610
NPAEF
``` or an immunogenic fragment thereof capable of eliciting an antibody response.

2. A bacterial protein or fragment according to claim 1 wherein the protein is obtained from any one of the group of *Streptococcus oralis, Streptococcus sobrinus, Streptococcus gordonii, Streptococcus sanguis, Streptococcus mutans, Streptococcus mitis, Streptococcus mitior, Streptococcus parasanguis,* and *Streptococcus bovis.*

3. A bacterial protein or fragment according to claim 1 which is produced recombinantly.

4. A composition for use in a method of diagnosis or treatment of a human or animal comprising the protein, or fragment, of claim 1 together with a pharmaceutically acceptable carrier, diluent or excipient.

5. An immunogenic fragment consisting of the sequence of any one of the group consisting of YEVEKPLEPAPVAPS (SEQ ID NO:3), SYENEPTPPVKPTD (SEQ ID NO:4), KTPDQPEPSKPEEPT (SEQ ID NO:5), EPAPVAPSY-ENEPTP (SEQ ID NO:6), YEVEKELVDLPVEPS (SEQ ID NO:7), KTPDQNIPDKPVEPT (SEQ ID NO:8), TMYPN-RQPGSGWDSS (SEQ ID NO:9), and WYSLNGKIRAVD-VPK (SEQ ID NO:10).

6. The immunogenic fragment according to claim 5 which is obtained from a bacterial protein which is involved in binding to heart valves.

7. The immunogenic fragment according to claim 5 which has been obtained from one of the group consisting of *Streptococcus oralis, Streptococcus sobrinus, Streptococcus gordonii, Streptococcus sanguis, Streptococcus mutans, Streptococcus mitis, Streptococcus mitior, Streptococcus parasanguis,* and *Streptococcus bovis.*

8. The immunogenic fragment according to claim 5 which is produced recombinantly.

9. A purified bacterial protein expressed during infection due to streptococci and isolated from human sera, wherein said bacterial protein comprises at least the sequence of formula (I) (SEQ ID NO:1):

| NH— | 10 EFTFYDANDQ | | PINFDNALLS | 30 VASLNREHNS | IEMAKDYSGT | 50 FIKISGSSIG | EKNGMIYATE |
|---|---|---|---|---|---|---|---|
| | 70 TLNFKQGQGG | | ARWTMYPNRQ | 90 PGSGWDSSDA | PNSWYGAGAI | 110 SMSGPTNHVT | VGATSATNVM |
| | 130 SVAEMPQVPG | | RDNTEGKRPN | 150 IWYSLNGKIR | AVDVPKITKE | 170 KPTPPVAPTE | PQAPTYEVEK |
| | 190 PLEPAPVAPS | | YENEPTPPVK | 210 TPDQPEPSKP | EEPTYETEKP | 230 LEPAPVAPNY | ENEPTPPVKT |
| | 250 PDQPDPSKPE | | EPNYETEKPL | 270 EPAPVAPSYE | NEPTPPVKTP | 290 DQPEPSKPEE | PNYDPLPTPP |
| | 310 LAPTPKQLPT | | PPAVPTVHFH | 330 YNRLFAQPQI | NKEIKNEDGV | 350 DIDRTLVAKQ | SVVKFELKTE |
| | 370 ALTAGRPKTT | | SFVLVDPLPT | 390 GYQFDLEATK | AASKGFETSY | 410 DKASHTVTFK | ATEETLAAFN |
| | 430 ADLTKSFETL | | YPTVVGRVLN | 450 DGATYTNNFT | LTVNDATGVK | 470 SNIVRVTTPG | KPNDPDNPNN |
| | 490 NYIKPLKVNK | | NKQGVNIDGK | 510 EVLAGSTNYY | ELTWDLDQYK | 530 GDKSSKEAIQ | NGFYYVDDYP |
| | 550 EEALTLQPEL | | VKIRDLEGNL | 570 VSGISVQQFD | SLERAPKKVQ | 590 DLLKKANITV | KGAFQLFSAD |
| | 610 NPAEF. | | | | | | |

10. A immunogenic fragment comprising the sequence TMYPNRQPGSGWDSS (SEQ ID NO:9) wherein said immunogenic fragment is caplable of eliciting an antibody response.

11. The immunogenic fragment according to claim 10 which is obtained from a bacterial protein which is involved in binding to heart valves.

12. The immunogenic fragment according to claim 10 which has been obtained from one of the group consisting of *Streptococcus oralis, Streptococcus sobrinus, Streptococcus gordonii, Streptococcus sanguis, Streptococcus mutans, Streptococcus mitis, Streptococcus mitior, Streptococcus parasanguis*, and *Streptococcus bovis*.

13. The immunogenic fragment according to claim 10 which is produced recombinantly.

* * * * *